(12) United States Patent
Dutta et al.

(10) Patent No.: US 12,106,829 B2
(45) Date of Patent: *Oct. 1, 2024

(54) ARTIFICIAL INTELLIGENCE-BASED MANY-TO-MANY BASE CALLING

(71) Applicant: Illumina, Inc., San Diego, CA (US)

(72) Inventors: Anindita Dutta, San Francisco, CA (US); Gery Vessere, San Francisco, CA (US); Dorna KashefHaghighi, Menlo Park, CA (US); Kishore Jaganathan, San Francisco, CA (US); Amirali Kia, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/352,029

(22) Filed: Jul. 13, 2023

(65) Prior Publication Data
US 2024/0055078 A1    Feb. 15, 2024

Related U.S. Application Data

(63) Continuation of application No. 17/180,542, filed on Feb. 19, 2021, now Pat. No. 11,749,380.
(Continued)

(51) Int. Cl.
*G06N 3/08* (2023.01)
*G16B 30/20* (2019.01)
(Continued)

(52) U.S. Cl.
CPC .............. *G16B 40/10* (2019.02); *G06N 3/08* (2013.01); *G16B 30/20* (2019.02); *C12Q 1/6869* (2013.01)

(58) Field of Classification Search
CPC ........ G16B 40/10; G16B 30/20; G16B 40/20; G16B 30/00; G06N 3/08; G06N 3/045;
(Continued)

(56) References Cited

U.S. PATENT DOCUMENTS 5,641,658 A    6/1997 Adams et al.
6,090,592 A    7/2000 Adams et al.
(Continued)

FOREIGN PATENT DOCUMENTS

CA    2894317 A1    12/2016
CA    3104851 A1    11/2020
(Continued)

OTHER PUBLICATIONS 3.3.9.11.Watershed and random walker for segmentation, Scipy lecture notes, 2 pages. (retrieved on Jun. 8, 2021] Retrieved from the internet <URL: http:scipy-lectures.org/packages/scikit-image/auto_examples/plot_segmentations.html>.
(Continued)

*Primary Examiner* — Charlotte M Baker
(74) *Attorney, Agent, or Firm* — Keller Preece PLLC

(57) ABSTRACT

The technology disclosed relates to artificial intelligence-based base calling. The technology disclosed relates to accessing a progression of per-cycle analyte channel sets generated for sequencing cycles of a sequencing run, processing, through a neural network-based base caller (NNBC), windows of per-cycle analyte channel sets in the progression for the windows of sequencing cycles of the sequencing run such that the NNBC processes a subject window of per-cycle analyte channel sets in the progression for the subject window of sequencing cycles of the sequencing run and generates provisional base call predictions for three or more sequencing cycles in the subject window of sequencing cycles, from multiple windows in which a particular sequencing cycle appeared at different positions, using the NNBC to generate provisional base call predictions for the particular sequencing cycle, and determining a base call for the particular sequencing cycle based on the plurality of base call predictions.

20 Claims, 16 Drawing Sheets

Related U.S. Application Data

(60) Provisional application No. 62/979,414, filed on Feb. 20, 2020.

(51) Int. Cl.
    *G16B 40/10* (2019.01)
    *C12Q 1/6869* (2018.01)

(58) Field of Classification Search
    CPC ........ G06N 3/044; G06N 3/084; G06N 20/00; C12Q 1/6869
    USPC .......................................................... 382/156
    See application file for complete search history.

(56) References Cited

U.S. PATENT DOCUMENTS

| | | |
|---|---|---|
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin |
| 7,405,281 B2 | 7/2008 | Xu et al. |
| 7,427,673 B2 | 9/2008 | Balasubramanian et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 8,182,993 B2 | 5/2012 | Tomaney et al. |
| 8,241,573 B2 | 8/2012 | Banerjee et al. |
| 8,392,126 B2 | 3/2013 | Mann |
| 8,401,258 B2 | 3/2013 | Hargrove et al. |
| 8,407,012 B2 | 3/2013 | Erlich et al. |
| 8,594,439 B2 | 11/2013 | Staelin et al. |
| 8,725,425 B2 | 5/2014 | Heiner et al. |
| 8,795,971 B2 | 8/2014 | Kersey et al. |
| 8,965,076 B2 | 2/2015 | Garcia et al. |
| 9,279,154 B2 | 3/2016 | Previte et al. |
| 9,453,258 B2 | 9/2016 | Kain et al. |
| 9,708,656 B2 | 7/2017 | Turner et al. |
| 10,023,911 B2 | 7/2018 | Tomaney et al. |
| 10,068,054 B2 | 9/2018 | Van Rooyen et al. |
| 10,152,776 B2 | 12/2018 | Langlois et al. |
| 10,168,438 B2 | 1/2019 | Dennis et al. |
| 10,241,075 B2 | 3/2019 | Davey et al. |
| 10,354,747 B1 | 7/2019 | DePristo et al. |
| 10,423,861 B2 | 9/2019 | Gao et al. |
| 10,527,549 B2 | 1/2020 | Rebetez et al. |
| 10,540,591 B2 | 1/2020 | Gao et al. |
| 10,619,195 B2 | 4/2020 | Lamb et al. |
| 10,648,027 B2 | 5/2020 | Mannion et al. |
| 10,711,299 B2 | 7/2020 | Rothberg et al. |
| 10,713,794 B1 | 7/2020 | He et al. |
| 10,740,880 B2 | 8/2020 | Paik et al. |
| 10,740,883 B2 | 8/2020 | Zerfass et al. |
| 10,755,810 B2 | 8/2020 | Buckler et al. |
| 10,963,673 B2 | 3/2021 | Schaumberg et al. |
| 11,138,496 B2 | 10/2021 | Seth |
| 11,210,554 B2 | 12/2021 | Dutta et al. |
| 11,347,965 B2 | 5/2022 | Dutta et al. |
| 2002/0055100 A1 | 5/2002 | Kawashima et al. |
| 2003/0062485 A1 | 4/2003 | Fernandez et al. |
| 2004/0002090 A1 | 1/2004 | Mayer et al. |
| 2004/0096853 A1 | 5/2004 | Mayer |
| 2006/0014151 A1 | 1/2006 | Ogura et al. |
| 2006/0040297 A1 | 2/2006 | Leamon et al. |
| 2006/0064248 A1 | 3/2006 | Saidi et al. |
| 2006/0188901 A1 | 8/2006 | Barnes et al. |
| 2006/0240439 A1 | 10/2006 | Smith et al. |
| 2006/0269130 A1 | 11/2006 | Maroy et al. |
| 2007/0128624 A1 | 6/2007 | Gormley et al. |
| 2007/0166705 A1 | 7/2007 | Milton et al. |
| 2008/0009420 A1 | 1/2008 | Schroth et al. |
| 2008/0234136 A1 | 9/2008 | Drmanac et al. |
| 2008/0242560 A1 | 10/2008 | Gunderson et al. |
| 2009/0081775 A1 | 3/2009 | Hodneland et al. |
| 2010/0046830 A1 | 2/2010 | Wang et al. |
| 2010/0111370 A1 | 5/2010 | Black et al. |
| 2010/0157086 A1 | 6/2010 | Segale et al. |
| 2011/0059865 A1 | 3/2011 | Smith et al. |
| 2011/0065607 A1 | 3/2011 | Kersey et al. |
| 2011/0281736 A1 | 11/2011 | Ormanac et al. |
| 2011/0286628 A1 | 11/2011 | Goncalves et al. |
| 2011/0295902 A1 | 12/2011 | Mande et al. |
| 2012/0015825 A1 | 1/2012 | Zhong et al. |
| 2012/0020537 A1 | 1/2012 | Garcia et al. |
| 2013/0059740 A1 | 3/2013 | Ormanac et al. |
| 2013/0079232 A1 | 3/2013 | Kain et al. |
| 2013/0124100 A1 | 5/2013 | Drmanac et al. |
| 2013/0188866 A1 | 7/2013 | Obrador et al. |
| 2013/0250407 A1 | 9/2013 | Schaffer et al. |
| 2014/0051588 A9 | 2/2014 | Ormanac et al. |
| 2014/0152801 A1 | 6/2014 | Fine et al. |
| 2015/0079596 A1 | 3/2015 | Eltoukhy et al. |
| 2015/0117784 A1 | 4/2015 | Lin et al. |
| 2015/0169824 A1 | 6/2015 | Kermani et al. |
| 2016/0042511 A1 | 2/2016 | Chukka et al. |
| 2016/0078272 A1 | 3/2016 | Hammoud |
| 2016/0110498 A1 | 4/2016 | Brauand et al. |
| 2016/0196479 A1 | 7/2016 | Chertok et al. |
| 2016/0350914 A1 | 12/2016 | Champlin et al. |
| 2016/0356715 A1 | 12/2016 | Zhong et al. |
| 2016/0357903 A1 | 12/2016 | Shendure et al. |
| 2016/0371431 A1 | 12/2016 | Haque et al. |
| 2017/0044601 A1 | 2/2017 | Crogorac et al. |
| 2017/0098032 A1 | 4/2017 | Desai et al. |
| 2017/0116520 A1 | 4/2017 | Min et al. |
| 2017/0161545 A1 | 6/2017 | Champlin et al. |
| 2017/0169313 A1 | 6/2017 | Choi et al. |
| 2017/0249421 A1 | 8/2017 | Eberle et al. |
| 2017/0249744 A1 | 8/2017 | Wang et al. |
| 2017/0362634 A1 | 12/2017 | Iota et al. |
| 2018/0075279 A1 | 3/2018 | Gertych et al. |
| 2018/0107927 A1 | 4/2018 | Frey |
| 2018/0114337 A1 | 4/2018 | Li et al. |
| 2018/0189613 A1 | 7/2018 | Wolf et al. |
| 2018/0195953 A1 | 7/2018 | Langlois et al. |
| 2018/0201992 A1 | 7/2018 | Wu et al. |
| 2018/0211001 A1 | 7/2018 | Gopalan et al. |
| 2018/0274023 A1 | 9/2018 | Belitz et al. |
| 2018/0305751 A1 | 10/2018 | Vermaas et al. |
| 2018/0322327 A1 | 11/2018 | Smith et al. |
| 2018/0330824 A1 | 11/2018 | Athey |
| 2018/0334711 A1 | 11/2018 | Kelley et al. |
| 2018/0334712 A1 | 11/2018 | Singer et al. |
| 2018/0340234 A1 | 11/2018 | Scafe et al. |
| 2019/0034586 A1 | 1/2019 | Pirrotte et al. |
| 2019/0080450 A1 | 3/2019 | Arar et al. |
| 2019/0107642 A1 | 4/2019 | Farhadi Nia et al. |
| 2019/0114544 A1 | 4/2019 | Sundaram et al. |
| 2019/0156915 A1 | 5/2019 | Zhang et al. |
| 2019/0164010 A1 | 5/2019 | Ma et al. |
| 2019/0170680 A1 | 6/2019 | Sikora et al. |
| 2019/0180153 A1 | 6/2019 | Buckler et al. |
| 2019/0213473 A1 | 7/2019 | Dutta et al. |
| 2019/0237160 A1* | 8/2019 | Rothberg ............... G16B 30/10 |
| 2019/0237163 A1 | 8/2019 | Wang et al. |
| 2019/0244348 A1 | 8/2019 | Buckler et al. |
| 2019/0266491 A1 | 8/2019 | Gao et al. |
| 2019/0272638 A1 | 9/2019 | Mouton et al. |
| 2019/0332118 A1 | 10/2019 | Wang et al. |
| 2019/0392578 A1 | 12/2019 | Chukka et al. |
| 2020/0027002 A1 | 1/2020 | Hickson et al. |
| 2020/0054306 A1 | 2/2020 | Mehanian et al. |
| 2020/0057838 A1 | 2/2020 | Yekhanin et al. |
| 2020/0065675 A1 | 2/2020 | Sundaram et al. |
| 2020/0176082 A1 | 6/2020 | Massingham |
| 2020/0193597 A1 | 6/2020 | Fan et al. |
| 2020/0226368 A1 | 7/2020 | Bakalo et al. |
| 2020/0256856 A1 | 8/2020 | Chou et al. |
| 2020/0302223 A1 | 9/2020 | Dutta et al. |
| 2020/0302224 A1 | 9/2020 | Jaganathan et al. |
| 2020/0302297 A1 | 9/2020 | Jaganathan et al. |
| 2020/0302603 A1 | 9/2020 | Barnes et al. |
| 2020/0320294 A1 | 10/2020 | Mangal et al. |
| 2020/0327377 A1 | 10/2020 | Jaganathan et al. |

(56) References Cited

U.S. PATENT DOCUMENTS

| | | |
|---|---|---|
| 2020/0342955 A1 | 10/2020 | Guo et al. |
| 2020/0364565 A1 | 11/2020 | Kostem |
| 2020/0388029 A1 | 12/2020 | Saltz et al. |
| 2021/0027462 A1 | 1/2021 | Bredno et al. |
| 2021/0056287 A1 | 2/2021 | Schaumburg et al. |
| 2021/0072391 A1 | 3/2021 | Li et al. |
| 2021/0089827 A1 | 3/2021 | Kumagai et al. |
| 2021/0115490 A1 | 4/2021 | Embree et al. |
| 2021/0264266 A1 | 8/2021 | Dutta et al. |
| 2021/0264267 A1 | 8/2021 | Dutta et al. |
| 2021/0265009 A1 | 8/2021 | Jaganathan et al. |
| 2021/0265015 A1 | 8/2021 | Parnaby et al. |
| 2021/0265016 A1 | 8/2021 | Vessere et al. |
| 2021/0265018 A1 | 8/2021 | Dutta et al. |
| 2021/0390278 A1 | 12/2021 | Vanleeuwen et al. |
| 2022/0067489 A1 | 3/2022 | Kashefhaghighi et al. |
| 2022/0147760 A1 | 5/2022 | Dutta et al. |

FOREIGN PATENT DOCUMENTS

| | | |
|---|---|---|
| CN | 110245685 A | 9/2019 |
| EP | 3130681 A1 | 2/2017 |
| EP | 3373238 A1 | 9/2018 |
| JP | 2007199397 A | 8/2007 |
| WO | 9106678 A1 | 5/1991 |
| WO | 2004018497 A2 | 3/2004 |
| WO | 2005065814 A1 | 7/2005 |
| WO | 2006064199 A1 | 6/2006 |
| WO | 2007010251 A2 | 1/2007 |
| WO | 2007123744 A2 | 11/2007 |
| WO | 2008154317 A1 | 12/2008 |
| WO | 2012058096 A1 | 5/2012 |
| WO | 2014142921 A1 | 9/2014 |
| WO | 2015084985 A2 | 6/2015 |
| WO | 2016145516 A1 | 9/2016 |
| WO | 2016201564 A1 | 12/2016 |
| WO | 2017184997 A1 | 10/2017 |
| WO | 2018129314 A1 | 7/2018 |
| WO | 2018165099 A1 | 9/2018 |
| WO | 2018203084 A1 | 11/2018 |
| WO | 2019027767 A1 | 2/2019 |
| WO | 2019028047 A1 | 2/2019 |
| WO | 2019055856 A1 | 3/2019 |
| WO | 2019079182 A1 | 4/2019 |
| WO | 2019079202 A1 | 4/2019 |
| WO | 2019090251 A2 | 5/2019 |
| WO | 2019136284 A1 | 7/2019 |
| WO | 2019136388 A1 | 7/2019 |
| WO | 2019140402 A1 | 7/2019 |
| WO | 2019147904 A1 | 8/2019 |
| WO | 2020014280 A1 | 1/2020 |
| WO | 2020123552 A1 | 6/2020 |
| WO | 2020191387 A1 | 9/2020 |
| WO | 2020191389 A1 | 9/2020 |
| WO | 2020191390 A1 | 9/2020 |
| WO | 2020191391 A1 | 9/2020 |
| WO | 2020205296 A1 | 10/2020 |
| WO | 2020232409 A1 | 11/2020 |
| WO | 2020232410 A1 | 11/2020 |

OTHER PUBLICATIONS

Adam, "Deep learning, 3D technology to improve structure modeling for protein interactions, create better drugs", dated Jan. 9, 2020, 4 pages.
Adriana Romero et al., FitNets: Hints for Thin Deep Nets, published Mar. 27, 2015, 13 pages. (ILLM 1017-3).
Adzhubei, I. A. et al. A method and server for predicting damaging missense mutations. Nat. Methods 7, 248-249 (2010).
Aggarwal, Neural Networks and Deep Learning: A Textbook, Springer, dated Aug. 26, 2018, 512 pages.
Ahmed, SIGNET: A Neural Network Architecture for Predicting Protein-Protein Interactions, The University of Western Ontario, dated May 7, 2017, 84 pages.
Alberts, Bruce, et al., "Molecular biology of the cell", Sixth Edition, 2015, 3 pages.
Albrecht et al., Deep learning for single molecule science, Nanotechnology, dated Sep. 18, 2017, 11 pages.
Albrecht et al., Deep learning for single-molecule science, Nanotechnology (28), dated 2017, 423001, 11 pages. TILLM. 1008-21).
Alipanahi, et al., "Predicting the Sequence Specificities of DNA and RNA Binding Proteins by Deep Learning", Aug. 2015, 9 pgs.
Amidi et al.. "EnzNet: enzyme classification using 3D convolutional neural networks on spatial representation", dated Jul. 25, 2017, 18 pages.
Angermueller, Christof, et al., Deep learning for computational biology, Molecular Systems Biology, dated Jun. 6, 2016, 16 pages.
Angermueller, et al., "Accurate Prediction of Single Cell DNA Methylation States Using Deep Learning", Apr. 1, 2017. 13 pgs.
Anonymous, "Transferable end-to-end learning for protein interface prediction", dated 2019, 12 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].
Arik et al., Deep Voice: Real-time Neural Text-to-Speech, 2017.
Aritake et al., "Single-molecule localization by voxel-wise regression using convolutional neural network", dated Nov. 3, 2020, 11 pages.
Arpali et al., High-throughput screening of large volumes of whole blood using structured illumination and fluorescent on-chip imaging, Lab on a Chip, United Kingdom, Royal Society of Chemistry, Sep. 12, 2012, vol. 12, pp. 4968-4971.
Assem, Predicting periodic and chaotic signals using Wavenets, Master of Science thesis, Delft University of Technology, Aug. 18, 2017, pp. 3-38.
Assfalg et al,. "3DString, A Feature String Kernel for 3D Object Classification on Voxelized Data", dated Nov. 6, 2006. 10 pages.
Asthana, S., Schmidt, S., & Sunyaev, S. A limited role for balancing selection. Trends Genet. 21, 30-32 (2005).
Badrinarayanan et. al., SegNet: A Deep Convolutional Encoder-Decoder Architecture for Image Segmentation, dated Oct. 10, 2016, 14 pages.
Baek et al., LncRNAnet: long non-coding RNA identification using deep learning, Bioinformatics, vol. 43 (22), 2018, pp. 3889-3897, 9 pages.
Bahar, Protein Actions Principles and Modeling, Chapter 7, 2017 pp. 165-166.
Bamshad, M. J. et al. Exome sequencing as a tool for Mendelian disease gene discovery. Nat. Rev. Genet. 12, 745-755 (2011).
Bazykin, G. A. et al. Extensive parallelism in protein evolution. Biol. Direct 2, 20, 13 pages (2007).
Belanovic, Library of Parameterized Hardware Modules for Floating-Point Arithmetic with an Example Application, Northeastern University, Boston, MA, May 2002, 83 pages.
Bell, C. J. et al. Comprehensive carrier testing for severe childhood recessive diseases by next generation sequencing Sci. Transl. Med. 3, Jan. 12, 2011, 28 pages.
Bentley et. al., Accurate Whole Human Genome Sequencing using Reversible Terminator Chemistry, Nature, Nov. 2008, 21 pages.
Bhande, Anup What is underfitting and overfitting in machine learning and how to deal with it, Mar. 11, 2018, 10 pages.
Bi, Yingtao, et al. "Tree-based position weight matrix approach to model transcription factor binding site profiles." PloS one6.9 (2011) e24210.
Bowen, Nanotechnology for a Genomic Revolution, Illumina, dated Dec. 14, 2016, 40 pages.
Boza et. al., Deep Recurrent Neural Networks for Base Calling in MinION Nanopore Reads, dated Mar. 30, 2016, 12 pages.
Boza et. al., DeepNano: Deep recurrent neural networks for base calling in MinION nanopore reads, PLOS ONE, dated Jun. 5, 2017, 13 pages.
Brandon, E. P., Idzerda, R. L. & Mcknight, G. S. Targeting the mouse genome—a compendium of knockouts (Part II). Curr. Biol. 5, 758-765 (1995).

(56) References Cited

OTHER PUBLICATIONS

Bravo et al., Model-Based Quality Assessment and Base-Calling for Second-Generation Sequencing Data, Biometrics, 2009, 10 pages.
Brookes, Anthony J., "The essence of SNPs", 1999, p. 177-186.
Cacho et al., A comparison of Base Calling Algorithms for Illumina Sequencing Technology, dated Oct. 5, 2015, Briefings in Bioinformatics 2016 (17), 786-795.
Cacho, Base-Calling of High-throughput Sequencing Data Using a Random Effects Mixture Model, UC Riverside, Dec. 2016, 102 pages.
Carter et al., "Cancer-specific high-throughput annotation of somatic mutations—computational prediction of driver missense mutations," Cancer research 69, No. 16 (2009) p. 6660-6667.
Carter, H., Douville, C., Stenson, P. D., Cooper, D. N., & Karchin, R. Identifying Mendelian disease genes with the variant effect scoring tool. BMC Genom, (2013), 13 pages.
Chang, Chia-Yun, et al. "Oversampling to overcome overfitting—exploring the relationship between data set composition, molecular descriptors, and predictive modeling methods." Journal of chemical information and modeling 53.4 (2013) 958-971.
Chen et al., Rethinking atrous convolution for semantic image segmentation, 2017.
Chen, Kathleen M, et. al., "Selene—a PyTorch based deep learning library for sequence level data", Oct. 10, 2018, 15 pages.
Chimpanzee Sequencing Analysis Consortium. Initial sequence of the chimpanzee genome and comparison with the human genome. Nature 437, 69-87 (2005).
Ching, et al. "Opportunities and Obstacles for Deep Learning in Biology and Medicine", May 26, 2017, 47 pgs.
Ching, et al., "Opportunities and Obstacles for Deep Learning in Biology and Medicine", Jan. 19, 2018, 123 pgs.
Choi, Y,. Sims, G. E,. Murphy, S,. Miler, .J R,. & Chan, A. P. Predicting the functional effect of amino acid substitutions and indels. PLoS One 7, e46688 (2012).
Chollet, Xception: Deep Learning with Depthwise Separable Convolutions, in Proc. of CVPR, 2017. 8 pages.
Chun, S. & Fay, J. C. Identification of deleterious mutations within three human genomes. Genome Res. 19, 1553-1561 (2009).
Das et. al., Model-based sequential base calling for Illumina sequencing, IEEE, 2010, 4 pages.
Dash et al., Artificial Intelligence and Evolutionary Computations in Engineering Systems, Advances in Intelligent Systems and Computing, vol. 1056, Springer2020, 781 pages.
Datta et. al., Statistical Analyses of Next Generation Sequence Data: A Partial Overview, Journal of Proteomics and Bioinformatics, vol. 3, Issue 6, 2010, 8 pages.
Davydov, E. V. et al. Identifying a high fraction of the human genome to be under selective constraint using GERP++ PLoS Comput. Biol. 6, Dec. 2, 2010, 13 pages.
dbSNP rs2241788 [Retrieved on Mar. 13, 2019], Retrieved from the Internetswww.ncbi.nlm.nih.gov/snp/rs2241788> 5 pages.
De Ligt, .J et al. Diagnostic exome sequencing in persons with severe intellectual disability. N. Engl. .J Med. 367. 1921-1929 (2012).
De Manuel, M. et al. Chimpanzee genomic diversity reveals ancient admixture with bonobos. Science 354, 477-481 (2016).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Deepa J, Development of Fully Automated Image Analysis Method for High Density cDNA and array CGH Microarray based genomic studies, Cochin University of Scienceand Technology, Mar. 2013, 232 pages.
Despois, Julien, "Memorizing is not learning! 6 tricks to prevent overfittingin machine learning", Mar. 20, 2018, 17 pages.
Dias et al., "Artificial intelligence in clinical and genomic diagnostics", dated 2019, 12 pages.
Dong. C. et al. Comparison and integration of deleteriousness prediction methods for nonsynonymous SNV s in whole exome sequencing studies. Hum. Mol. Genet. 24, 2125-2137 (2015).
Duggirala, Ravindranath, et.al., "Genome Mapping and Genomics in Human and Non Human Primate", 2015, 306 pgs.
Dunbrack, Roland,L. Re Question about your Paper titled "The Role of Balanced Training and Testing Data Sets for Binary Classifiers in Bioinformatics", Message to Sikander Mohammed Khan, Feb. 3, 2019, E-mailm, 3 pgs.
Epi, K.C. et al. De novo mutations in epileptic encephalopathies. Nature 501, 217-221 (2013).
Erlich et al., Alta-Cyclic: a self-optimizing base-caller for next generation sequencing, Nature Methods, Aug. 2008, 7 pages.
Estrada, A. et al. Impending extinction crisis of the world's primates—why primates matter. Sc. Adv. 3, e1600946 (2017), 17 pages.
EuroEPINOMICS-RES Consortium, Epilepsy Phenome/Genome Project, Epi4K Consortium. De novo mutations in 46 synaptic transmission genes including DM1 cause epileptic encephalopathies. Am. J. Hum. Genet. 95, 360-370 2014).
Evans et. al., Estimating Change-Points in Biological Sequences via the Cross-Entropy Method,dated Sep. 20, 2010, 17 pages.
Famiglietti, M. .L et al. Genetic variations and diseases in UniProtKB Swiss-Prot—the ins and outs of expert manual curation. Human. Mutat. 35, 927-935 (2014).
Forghani et al., Convolutional Neural Network Based Approach to In Silica Non-Anticipating Prediction of Antigenic Distance for Influenza Virus, Viruses, published Sep. 12, 2020, vol. 12, 20 pages.
Fritzilas, An Overview of Illumina's Sequencing Technology and its Applications, University of Primorska, dated Mar. 4, 2011, 47 pages.
Gao et al., Deep Learning in Protein Structural Modeling and Design, Patterns—CelPress, dated Dec. 11, 2020, 23 pages.
Gao, Tingting, et al. "Identifying translation initiation sites in prokaryotes using support vector machine." Journal of Theoretical biology 262.4 (2010) 644-649. (Year 2010).
Geeks for Geeks, "Underfitting and Overfilling in Machine Learning", [retrieved on Aug. 26, 2019]. Retrieved from the Internet <www.geeksforgeeks.org/underfitting-and-overfitting-in-machine--leaming/>, 2 pages.
Genomes Project Consortium.et al. A global reference for human genetic variation. Nature 526, 68-74 (2015).
Gilissen, C. et al. Genome sequencing identifies major causes of severe intellectual disability. Nature 511, 344-347 (2014).
Goodfellow et al., Convolutional Networks, Deep Learning, MIT Press, 2016.
Grantham, R. Amino acid difference formula to help explain protein evolution. Science 185, 862-864 (1974).
Grimm, D. G. The evaluation of tools used to predict the impact of missense variants is hindered by two types of circularity. Human. Mutat. 36, 513-523 (2015).
Grob, C, et al. "Predicting, variant deleteriousnes in non human species Appylnig the CAD approach in mouse",. 2018, 11 pages.
Gu, et al., "Recent Advances in Convolutional Neural Networks", Jan. 5, 2017, 37 pgs.
Gulko, B., Hubisz, M. J., Gronau, I., & Siepel, A. Amethod for calculating probabilities of fitness consequences for point mutations across the human genome. Nat. Genet. 47, 276-283 (2015).
Hacteria Wiki, HiSeq2000—Next Level Hacking—Hackteria Wiki, retrieved on Apr. 12, 2021, retrieved from the internet URL: https://www.hackteria.org/wiki/HiSeq2000_-_Next_Level_Hacking ,] 42 pages.
Han, Deconvolutions in Convolutional Neural Networks, Postech Computer Vision Lab, 2015, 20 pages.
Harpak, A., Bhaskar, A., & Pritchard, J. K. Mutation rate variation is a primary determinant of the distribution of allele frequencies in humans. PLoS Genet. Dec. 15, 2016, 22pgs.
He et. al., Deep Residual Learning for Image Recognition, 2015.
He et. al., Deep Residual Learning for Image Recognition, in Proc.of CVPR, 2016.
He, K, Zhang, X., Ren, S., & Sun, J. Identity mappings in deep residual networks in 14th European Conference on Computer

(56) References Cited

OTHER PUBLICATIONS

Vision—ECCV 2016. ECCV 2016. Lecture Notes in Computer Science, vol. 9908; 630 6,15 (Springer, Cham. Switzerland; 2016).
Hedegaard, An introduction to "NextGeneration" DNA Sequencing, dated Nov. 26, 2017, 63 pages.
Hefferman, R. et al. Improving prediction of secondary structure, local backbone angles, and solvent accessible surface area of proteins by iterative deep learning. Sci. Rep. 5, 11476 (2015) 1 pages.
Henikoff, S. & Henikoff, .J G. Amino acid substitution matrices from protein blocks. Proc. Natl. Acad. Sci. USA 89, 10915-10919 (1992).
Horaitis, O., Talbot, C. C. Jr., Phommarinh, M,. Phillips, K. M,. & Cotton, R. G. A database of locus-specific databases. Nat. Genet. 39, 425 (2007).
Howard et al., Mobilenets: Efficient Convolutional Neural Networks for Mobile Vision Applications, 2017.
Huang et al., Densely Connected Convolutional Networks, 2017.
Huang et al., Speed/accuracy trade-offs for modern convolutional detectors, 2016.
Illumina, "Indexed Sequencing Overview Guide", Document No. 15057455, .v 5, Mar. 2019 (ILLM 1015-1).
Illumina, An Introduction ot Next-Generation Sequencing Technology, 2017, 16 pages.
Illumina, Calculating Percent Passing Filter for Patterned and Nonpatterned Flow Cells, 2017, 2 pages.
Illumina, HCS 1.4/RTA .1 12 Theory of Operation, 2010, 32 pages.
Illumina, Illumina's Genotyping Data Normalization Methods, 2006, 6 pages.
Illumina, Low-diversity sequencing on the Illumina HiSeq Platform, 2014, 2 pages.
Illumina, Optimizing Cluster Density on Illumina Sequencing Systems, 2016, 12 pages.
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm].
Illumina, Quality Scores for Next-Generation Sequencing—Assessing sequencing accuracy using Phred quality scoring 2011, 2 pages.
Illumina, Reducing Whole-Genome Data Storage Footprint, Illumina Whitepaper, 2010-2014, 4 pages.
Illumina, RTA Theory of Operation, 2009, 8 pages.
Illumina, Two-Channel SBS Sequencing Technology, 2016, 2 pages.
Illumina, Understanding Illumina Quality Scores, dated Apr. 23, 2014, 2 pages.
Ioannidis, Nilah M., et al., REVEL—An Ensemble Method for Predicting the Pathogenicity of Rare Missense Variants, Oct. 3, 2016, 9 pages.
Ioffe et al., Batch Normalization Accelerating Deep Network Training by Reducing Internal Covariate Shift, 2015.
Ionita-Laza, ,.I McCalum, K,. Xu, B,. & Buxbaum, J. D. A spectral approach integrating functional genomic annotations or coding and noncoding variants. Nat. Genet. 48, 214-220 (2016).
Iossifov, .I et al. The contribution of de novo coding mutations to autism spectrum disorder. Nature 515, 216-221 (2014).
Iossifov, I. et al. De novo gene disruptions in children on the autistic spectrum. Neuron 74, 285-299 (2012).
Iqbal et al., Comprehensive characterization of amino acid positions in protein structures reveals molecular effects of missense variants, and supplemental information, PNAS, vol. 117, No. 45, dated Nov. 10, 2020, 35 bages.
Jagadeesh, K. A. et al. M-CAP eliminates a majority of variants of uncertain significance in clinical exomes at high sensitivity. Nat. Genet. 48, 1581-1586 (2016).
Jaganathan, K. et. al., "Predicting splicing from primary sequence with deep learning", Cell 176, 535-548, (2019).
Jain, S., White, M., Radivojac, P. Recovering true classifier performance in positive-unlabeled learning. in Proceedings Thirty-First AAAI Conference on Artificial Intelligence.2066-2072 (AAAI Press, San Francisco; 2017).
James Le, How to do Semantic Segmentation using Deep Learning, dated May 3, 2018, 17 pages, retrieved on 21 | Puly 2021. Retrieved from [URL: https://medium.com/nanonets/how-to-do-image-segmentation-using-deep-learning-C673cc5862ef].
Jiminez et al., DeepSite—protein binding site predictor using 3D CNNs, dated Oct. 1, 2017, 7 pages.
Jing et al., Learning from protein structure with geometric vector perceptrons, Arxiv: 2009: 0141 1v2, dated Dec. 31, 2020, 18 pages.
Joosten, R. P. et al. A series of PDB related databases for everyday needs. Nucleic Acids Res. 39, 411-419 (2011).
Jordan. An overview of semantic image segmentation, dated May 21, 2018, 28 pages retrieved on Jul. 21, 2021 Retrieved from the internet [URL: https://www jeremyjordan.me/semantic-segmentation/ ].
Kabsch, W,. & Sander, C. Dictionary of protein secondary structure—pattern recognition of hydrogen-bonded and geometrical features. Biopolymers 22, 2577-2637 (1983).
Kao et. al., Algorithms for Next-Generation High-Throughput Sequencing Technologies, University of California, Berkeley, 2011, 106 pages.
Kao et al., BayesCall: A model-based base-calling algorithm for high-throughput short-read sequencing, Genome Research (19), p. 1884-1895, dated 2009.
Kao et al., naiveBayesCall: An Efficient Model-Based Base-Calling Algorithm for High-Throughput Sequencing, Journal of Computational Biology, dated Mar. 2011, 16 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
Kent, W. J. et al. The human genome browser at UCSC. Genome Res. 12, 996-1006 (2002).
Kingma et al., Adam: A method for Stochastic Optimization, ICLR 2015, dated Jul. 23, 2015.
Kircher et al. Improved-base-calling-for-the-Illumina-Genome-Analyzer-using-machine-learning-strategies_14 August 2009_10 pages (ILLM1020-3 WO).
Kircher et al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/1.
Kircher et al., Improved base-calling for the Illumina Genome Analyzer using Machine Learning Strategies, Genome Biology, published Aug. 14, 2009, 9 pages.
Kircher, Improving data quality of the Illumina Genome Analyzer platform, Max Planck Institute for Evolutionary Anthropology, dated Oct. 24, 2009, 46 pages.
Kircher, Martin, et al. "A general framework for estimating the relative pathogenicity of human genetic variants." Nature genetics 46.3 (2014): 310. (Year:2014).
Kircher, Understanding and Improving high-throughput sequencing data production and analysis, Leipzig University, 2011, 216 pages.
Klein, J,. Salta, Y,. O'HUigin, C,. & Takahata, N. The molecular descent of the major histocompatibility complex. Annu. Rev. Immunol. 11,269-295 (1993).
Korhonen, Janne H.,et al. "Fast motif matching revisited—high-order PWMs, SNPs and indels." Bioinformatics 33.4 {2016) 514-521.
Kriseman et. al., BING: Biomedical informatics pipeline for Next Generation Sequencing, Journal of Biomedical Informatics, vol. 43, 2010, p. 428-434, 7 pages.
Krishnakumar et al., Systematic and stochastic influences on the performance of the MinION nanopore sequencer across a range of nucleotide bias, Scientific Reports, published Feb. 16, 2018, 13 pages.
Krizhevsky, Alex, et al., ImageNet Classification with Deep Convolutional Neural Networks, 2012, 9 Pages.

(56) References Cited

OTHER PUBLICATIONS

Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.

Lanchantin, Deep Motif Dashboard: Visualizing and Understating Genomic Sequences Using Deep Neural Networks, Oct. 18, 2016, 11 pages.

Landrum, M. J. et al. ClinVar—public archive of interpretations of clinically relevant variants. Nucleic Acids Res. 44, 0802-868 2016).

Lavin et al., Fast Algorithms for Convolutional Neural Networks, dated Nov. 10, 2015, 9 pages.

Lecun, Y., Botlou, L., Bengio, Y., & Haffner, P. Gradient based learning applied to document recognition. Proc. EIE 36, 2278-2324 (1998).

Ledergerber et.al., Base-calling for next-generation sequencing platforms, Briefings in Bioinformatics vol. 12, No. 5, pp. 489 497, dated Jan. 18, 2011, 9 pages.

Lee et. al., Fast Object Localization Using a CNN Feature Map Based Multi-Scale Search, dated Apr. 12, 2016, 16 pages.

Leffler, E. M. et al. Multiple instances of ancient balancing selection shared between humans and chimpanzees. Science 339, 12 pages (2013).

Leffler, E. M. et al. Revisiting an old riddle: what determines genetic diversity levels within species?PLoS Biol. 10,=1001388(2012),pages.

Lek, M. et al. Analysis of protein-coding genetic variation in 60,706 humans. Nature 536, 285-291 (2016).

Lelieveld, S. H. et al. Meta-analysis of 2, 104 trios provides support for 10 new genes for intellectual disability. Nat. Neurosci. 19, 1194-1196 (2016).

Leung, et al., "Deep learning of the tissue regulated splicing code", 2014, 9 pgs.

Leung, et al., "Inference of the Human Polyadenylation Code", Apr. 27, 2017, 13 pgs.

Leung, et. al., "Machine Learning in Genomic Medicine", Jan. 1, 2016, 22 pgs.

Li et. al., "DeepAtom: A Framework for Protein-Ligand Binding Affinity Prediction", dated 2019, 8 pages.

Li et. al., "Predicting changes in protein thermostability upon mutation with deep 3D convolutional neural networks", dated Feb. 28, 2020, 21 pages.

Li et. al., CS231 Lecture 13 Segmentation and Attention, Stanford University, dated Feb. 24, 2016, 133 pages.

Li et. al., DeepSimulator: a deep simulator for Nanopore sequencing, Bioinformatics 34(17), 2018, p. 2899-2908, 10 pages.

Li, "Machine Learning Methods for Medical and Biological Image Computing", dated Summer 2016, 113 pages.

Li, B. et al. Automated inference of molecular mechanisms of disease from amino acid substitutions. Bioinformatics 25, 2744-2750 (2009).

Li, et. al., "FoldingZero—Protein Folding from Scratch in Hydrophobic Polar Model", Dec. 3, 2018, 10 pages.

Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.

Li, W. H., Wu, C. .I & Luo, C. C. Nonrandomness of point mutation as reflected in nucleotide substitutions in pseudogenes and its evolutionary implications. J. Molec. Evol. 21, 58-71 (1984).

Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.

Libbrecht, et. al., "Machine learning in genetics and genomics", Jan. 2, 2017, 30 pgs.

Lieschke, J. G. & Currie, P. D. Animal models of human disease—zebrafish swim into view. Nat. Rev. Genet. 8, 353-367 (2007).

Lin et. al., Network in Network, in Proc. of ICLR, 2014.

Linder, Modeling the intronic regulation of Alternative Splicing using Deep Convolutional Neural Nets, KTH Institute of Technology, dated Jun. 14, 2015, 53 pages.

Liu et. al., A Uniform Architecture Design for Accelerating 2D and 3D CNNs on FPGAs, published Jan. 7, 2019, 19 pages.

Liu, X,. Jian, .X & Boerwinkle, E. dbNSFP—a lightweight database of human nonsynonymous SNPs and their junctional predictions. Human. Mutat. 32, 894-899 (2011).

Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).

Locke, D. P. et al. Comparative and demographic analysis of orangutan genomes. Nature 469, 529-533 (2011).

Long et. al., Fully Convolutional Networks for Semantic Segmentation, IEEE Transactions on Pattern Analysis and Machine Intelligence, vol. 39, Issue 4, Apr. 1, 2017, 12 pages.

Lu, Q. et al. A statistical framework to predict functional non-coding regions in the human genome through integrated analysis of annotation data. Sci. Rep. 5, 10576 (2015), 13 pgs.

Lui et. al., 3D Stacked Many Core Architecture for Biological Sequence Analysis Problems, 2017, Int J Parallel Prog, 45:1420-1460.

Luna et al., A"Deep-Learning Approach toward Rational Molecular Docking Protocol Selection", dated May 27, 2020, 12 pages.

Luna, "Machine Learning in structural biology and chemoinformatics", dated 2019, 106 pages.

Luo et. al., A multi-task convolutional deep neural network for variant calling in single molecule sequencing, Nature Communications (10), No. 1, dated Mar. 1, 2019.

Luo et. al., G-softmax: Improving Intra-class Compactness and Inter-class Separability of Features, dated Apr. 8, 2019, 15 pages.

Luo et. al., Skyhawk: An Artificial Neural Network-based discriminator for reviewing clinically significant genomic variants, dated Jan. 28, 2019, 8 pages.

Lutteropp, Error-Profile-Aware Correction of Next Generation Sequencing Reads, Karlsruhe Institute of Technology, dated Mar. 31, 2017, 96 pages.

MacArthur, D. G. et al. Guidelines for investigating causality of sequence variants in human disease. Nature 508, 469 476 (2014).

Mallick, S. et al. The Simons Genome Diversity Project—300 genomes from 142 diverse populations. Nature 538. 201-206 (2016).

Martin-Navarro, Antonio, et al. "Machine learning classifier for identification of damaging missense mutations exclusive to human mitochondrial DNA-encoded polypeptides." BMC bioinformatics 18.1 (2017) p. 158.

Massingham, Base Calling: methods, problems and alternatives, EMBL Advanced Course in Analysis of Short Read Sequencing Data, Jun. 8, 2009-Jun. 10, 2009, 84 pages.

Min, et. al., "Deep Learning in Bioinformatics", Jul. 25, 2016, 19 pgs.

Min, et. al., "Deep Learning in Bioinformatics", Jun. 19, 2016, 46 pgs.

MiSEQ: Imaging and Base Calling Script, retrieved on [Jun. 14, 2021], Retrieved from the internet <URL: https://support.Illumina.com/content/dam/illuminasupport/courses/MiSe_maging_and_Base_Calling/story_content/external_files/ ViSeq%201maging%20and%20Base%20Calling%20Script.pdf>.

MISEQ: Imaging and Base Calling: Illumina, Inc. Online Training Course, colored version, retrieved on Oct. 11, 2020. Retrieved from <URL: https://support.illumina.com/training. html >, 9 pages.

MiSEQ: Imaging and Base Calling: Illumina, Inc. Online Training Course, dated Jan. 1, 2013 [retrieved on Jul. 13, 2020], Retrieved from<URL: https://support.illumina.com/training.html >, 13 pages.

Misiunas et. al., QuipuNet: convolutional neural network for single-molecule nanopore sensing, dated May 30, 2018, 7 pages.

Mitra et. al., Strategies for Achieving High Sequencing Accuracy for Low Diversity Samples and Avoiding Sample Bleeding Using Illumina Platform, PLOS One, published Apr. 10, 2015, 21 pages.

Morrone et al., "Combining docking pose rank and structure with deep learning improves protein-ligand binding mode prediction", dated Oct. 7, 2019, 13 pages.

(56) References Cited

OTHER PUBLICATIONS

Nakamura, K. et al. Clinical spectrum of SCN2A mutations expanding to Ohtahara syndrome. Neurology 81, 992-998 (2013).
Neale, B. M.et al. Patterns and rates of exonic de novo mutations in autism spectrum disorders. Nature 485,242-245 (2012).
Ng, P. C., & Henikoff, S. Predicting deleterious amino acid substitutions. Genome Res. 11, 863-874 (2001).
Nolowski, High-quality, high-throughput measurement of protein-DNA binding using HiTS-FLIP, Ludwig Maxmilian University, 2016, 251 pages.
O'Roak, B. J. et al. Sporadic autism exomes reveal a highly interconnected protein network of de novo mutations. Nature 485, 246-250 (2012).
Ohta, .T Slightly deleterious mutant substitutions in evolution. Nature 246, 96-98 (1973).
Oord, Dieleman et. al., WAVENET: A Generative Model for Raw Audio, 2016.
Pakhrin et al., Deep learning based advances in protein structure prediction, International Journal of Molecular sciences, published May 24, 2021, 30 pages.
Park, et. al., "Deep Learning for Regulatory Genomics", Aug. 2015, 2 pgs.
Payandeh, J., Scheuer, T., Zheng, N.& Catterall, W. A. The crystal structure of a voltage-gated sodium channel. Nature 475, 353-358 (2011).
Pei et al., A Topological Measurement for Weighted Protein Interaction Network, IEEE Computational Systems Bioinformatics Conference dated 2005, 11 pages.
Pejaver et al., Inferring the molecular and phenotypic impact of amino acid variants with MutPred2—with Supplementary Information, Nature Communications, dated 2020, 59 pages.
Peresini et. al., Nanopore Base Calling on the Edge, dated Nov. 9, 2020, 15 pages.
Pfeiffer et. al., Systematic evaluation of error rates and causes in short samples in next-generation sequencing, Scientific Reports, published Jul. 19, 2018, 14 pages.
Piqueras, Autoregressive Model Based on a Deep Convolutional Neural Network for Audio Generation, Tampere University of Technology, 2016.
Prabhakar et. al., Plasticine: A Reconfigurable Architecture for Parallel Patterns, ISCA '17, Jun. 24-28, 2017, Toronto, ON, Canada.
Prado-Martinez, J. et al. Great ape genome diversity and population history. Nature 499, 471-475 (2013).
Pu et. al., "DeepDrug3D: Classification of ligand-binding pockets in proteins with a convolutional neural network", dated Feb. 4, 2019, 23 pages.
Puckelwartz et al., Supercomputing for the parallelization of whole genome analysis, Bioinformatics, dated Feb. 12, 2014, pp. 1508-1513, 6 pages.
Qin et. al., FD-MobileNet: Improved MobileNet with a Fast Downsampling Strategy, 2018.
Quang Daniel, et. al.,. "DANN—a deep learning approach for annotating the pathogenicity of genetic variants", Oct. 2, 2014, 3 pages.
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages ILLM 1008-17).
Rang et. al., From squiggle to basepair: computational approaches for improving nanopore sequencing read accuracy. Genome Biology 2018, (19), 30.
Raschka et. al., "Machine Learning and AI-based approaches for bioactive ligand discovery and GPCR-ligand recognition", dated Jun. 6, 2020, 33 pages.
Ratkovic, Deep Learning Model for Base Calling of MinION Nanopore Reads, dated Jun. 2017, 48 pages.
Rauch, A. et al. Range of genetic mutations associated with severe non-syndromic sporadic intellectual disability—an exome sequencing study. Lancet 380, 1674-1682 (2012).
Rehm, H. .L Evolving health care through personal genomics. Nat. Rev. Genet. 18, 259-267 (2017).
Rehm, H. L. et al. ClinGen—the Clinical Genome Resource. N. Engl. J. Med.372, 2235-2242 (2015).
Reich, D. E. & Lander, E. S. On the allelic spectrum of human disease. Trends Genet. 17, 502-510 (2001).
Renaud et. al., freelbis: an efficient base caller with calibrated quality scores for Illumina sequencers, dated Mar. 6, 2013, 2 pages.
Rentzsch, et. al., "CADD—predicting the deleteriousness of variants throughout the human genome", Oct. 1, 2018, 9 pages.
Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].
Reva, B,. Antipin, Y,. & Sander, C. Predicting the functional impact of protein mutations—application to cancer genomics. Nucleic Acids Res. 39, e118 (2011), 14 pgs.
Rhesus Macaque Genome Sequencing Analysis Consortium. Evolutionary and biomedical insights from the rhesus macaque genome. Science 316, 222-234 (2007).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Rivera et. al., "A Deep Learning Approach to Protein Structure Prediction", dated Apr. 24, 2019, 22 pages.
Robinson et al., Computational Exome and Genome Analysis—Chapter 3 Illumina Technology, dated 2018, 25 pages.
Rodriguez-Ezpeleta, Bioinformatics for High Throughput Sequencing, Springer, 2012, 266 pages.
Ronneberger et. al., U-net : Convolutional networks for biomedical image segmentation, in International Conference on Medical Image computing and computer assisted intervention, May 18, 2015, 8 pages.
Samocha, K. E. et al. A framework for the interpretation of de novo mutation in human disease. Nat. Genet. 46, 944-950 (2014).
Sanders, S. J. et al. De novo mutations revealed by whole-exome sequencing are strongly associated with autism. Nature 485, 237-241 (2012).
Sandler et. al., MobileNetV2: Inverted Residuals and Linear Bottlenecks, 2018.
Schilling, The Effect of Batch Normalization on Deep Convolutional Neural Networks, KTH Royal Institute of Technology, 2016, 113 pages.
Schrago, C. G., & Russo, C. A. Timing the origin of New World monkeys. Mol. Biol. Evol. 20, 1620-1625 (2003).
Schwarz, J. M., Rodelsperger, C., Schuelke, M. & Seelow, D. MutationTaster evaluates disease-causing potential of sequence alterations Nat. Methods 7, 575-576 (210).
Scikit-image/peak.py at master, Github, retrieved on Jun. 8, 2021, 10 pages, Retrieved from the internet <URL: https:/ / github.com/scikit-image/scikit-image/blob/main/skimage/feature/peak.py>.
Shamaiah et al., Base calling error rates in next-generation DNA sequencing, IEEE Statistical Signal Processing Workshop, 2012, 4 pages.
Sheikh et. al., Chapter 5 Base-Calling for Bioinformaticians, 2012, 17 pages.
Shen et. al., ParticleCall: A particle filter for base calling in next-generation sequencing systems, BMC Bioinformatics, 2012, 10 pages.
Shen, H. et al. Structure of a eukaryotic voltage-gated sodium channel at near-atomic resolution. Science 355. eaal4326 (2017), 19 pages.
Sherry, S. T. et al. dbSNP—the NCBI database of genetic variation. Nucleic Acids Res. 29, 308-211 (2001).
Shevchenko, Keras weighted categorical_ crossentropy, Github, [retrieved on Jun. 12, 2021], Retrieved from the internet <URL: https://gist.github.com/skeeet/cad06d584548f45eece1d428cfa98b >, 2 pages.
Shihab, H. A. et al. An integrative approach to predicting the functional effects of non-coding and coding sequence variation. Bioinformatics 31, 1536-1543 (2015).

(56) References Cited

OTHER PUBLICATIONS

Shihab, H. A. et al. Predicting the functional, molecular, and phenotypic consequences of amino acid substitutions using hidden Markov models. Human. Mutat. 34, 57-65 (2013).

Sifre et.al., Rotation, Scaling and Deformation Invariant Scattering for Texture Discrimination, in Proc. of CVPR, 2013.

Sifre, Rigid-motion Scattering for Image Classification, Ph.D. thesis, 2014.

Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-dOa11fe0a7aa ].

Sittig, .L J. et al. Genetic background limits generalizability of genotype-phenotype relationships. Neuron 91, 1253-1259 (2016).

Smedley. D. et al. A whole-genome analysis framework for effective identification of pathogenic regulatory variants in mendelian disease. Am. .J Hum. Genet. 9, 595-606 (2016).

Smith et. al., Barcoding and demultiplexing Oxford nanopore native RNA sequencing reads with deep residual earning, bioRxiv, dated Dec. 5, 2019, 18 pages.

Snuverink, Deep Learning for Pixelwise Classification of Hyperspectral Images, Master of Science Thesis, Delft University of Technology, Nov. 23, 2017, 128 pages.

Srivastava et. al., Highway Networks, 2015.

Stenson, P. D. et al. The Human Gene Mutation Database—building a comprehensive mutation repository for clinical and molecular genetics, diagnostic testing and personalized genomic medicine. Hum. Genet. 133, 1-9 (2014).

Stoiber et. al., BasecRAWller: Streaming Nanopore Basecalling Directly from Raw Signal, dated May 1, 2017, 15 pages.

Sundaram, et. al., "Predicting the clinical impact of human mutation with deep neural networks", Aug. 2018, 15 pgs.

Sze et. al., Efficient Processing of Deep Neural Networks: A Tutorial and Survey, Cornell University Library, dated Mar. 27, 2017, 21 pages.

Szegedy et. al., Going Deeper with Convolutions, 2014.

Takahata, N. Allelic genealogy and human evolution. Mol. Biol. Evol. 10, 2-22 (1993).

Tegfalk, Application of Machine Learning techniques to perform base-calling in next-generation DNA sequencing, KTH Royal Institute of Technology, dated 2020, 53 pages.

Teng et. al,. Chiron: translating nanopore raw signal directly into nucleotide sequence using deep learning, dated Aug. 23, 2017, 10 pages.

Teng et. al., Chiron: translating nanopore raw signal directly into nucleotide sequence using deep learning, SigaScience, 7, 2018, 9 pages.

Thakur et. al., A Survey of Image Segmentation Techniques, International Journal of Research in Computer Applications and Robotics, vol. 2, Issue 4, Apr. 2014, p. 158-165.

Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/.

Thoma, A Survey of Semantic Segmentation, dated May 11, 2016, 16 pages.

Torng, Wen, et al., "3D deep convolutional neural networks for amino acid environment similarity analysis", 2017 23 pages.

Townley, Illumina Primary and Secondary Analysis, Illumina UK, 2010, 33 pages.

Townshend et. al., "End-to-End Learning on 3D Protein Structure for Interface Prediction", dated 2019, 10 pages.

Tutorial Image Segmentation, BoofCV, 6 pages, retrieved on Jul. 23, 2021. Retrieved from [URL: https://boofcv.org/index.php?title=Tutorial_Image_Segmentation].

Tyner, C. et al. The UCSC Genome Browser database—2017 update. Nucleic Acids Res. 45, D626-D634 (2017).

UniProtKB P04217 A1BG Human [retrieved on Mar. 13, 2019 from (www.uniprot.org/uniprot/P04217), 12 pages.

Varela, "Ligvoxel: A Deep Learning Pharmacore-Field Predictor", dated Mar. 19, 2019, 5 pages.

Vissers, .L E., Gilissen, C., & Veltman, J. A. Genetic studies in intellectual disability and related disorders. Nat. Rev. Genet. 17, 9-18 (2016).

Vlzur, Watershed.py, Github, 3 pages. [retrieved on Jun. 8, 2021] Retrieved from the internet <URL: https://github.com/ zur/watershed/blob/master/Watershed.py>.

Wallach et. al., AtomNet: A Deep Convolutional Neural Network for Bioactivity Prediction in Structure-based Drug Discovery, dated Oct. 10, 2015, 11 pages.

Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.

Wang et al., Achieving Accurate and Fast Base-calling by a Block model of the Illumina Sequencing Data, Science Direct, vol. 48, No. 28, dated Jan. 1, 2015, pp. 1462-1465, 4 pages.

Wang et. al., An adaptive decorrelation method removes Illumina DNA base-calling errors caused by crosstalk between adjacent clusters—with Supplemental Materials, Scientific Reports, published Feb. 20, 2017, 17 pages.

Wang et. al., An adaptive decorrelation method removes Illumina DNA base-calling errors caused by crosstalk between adjacent clusters, Scientific Reports, published Feb. 20, 2017, 11 pages.

Wang et. al., Deep Neural Network Approximation for Custom Hardware: Where We've Been, Where We're Going, Cornell University, dated Jan. 21, 2019, 37 pages.

Wang et al., DeepDNA: a hybrid convolutional and recurrent neural network for compressing human mitochondrial genomes, IEEE International Conference on Bioinformatics and Biomedicine,2018, 5 pages.

Wang, S., Peng, J., Ma, J. & Xu, J. Protein secondary structure prediction using deep convolutional neural fields. Sci Rep. 6, 10962-10962 (2016).

Wei et al. The Role of Balanced Training and Testing Data Sets for Binary Classifiers in Bioinformatics dated Jul. 9, 2013 12 pages.

Wei, et. al., "Prediction of phenotypes of missense mutations in human proteins from biological assemblies", Feb. 2013, 28 pages.

Whiffin, N. et al. Using high-resolution variant frequencies to empower clinical genome interpretation. Genet. Med. 19, 1151-1158(2017).

Whiteford et. al., Swift: Primary data analysis for the Illumina Solexa sequencing platform, Bioinformatics, vol. 25, No. 17, 2009, pp. 2194-2199, 7 pages.

Wick et. al., Performance of neural network basecalling tools for Oxford Nanopore sequencing, Genome Biology, 2019, 10 pages.

Wick et. al., Performance of neural network basecalling tools for Oxford Nanopore sequencing, dated Feb. 7, 2019, 14 pages.

Wolterink et. al., Dilated Convolutional Neural Networks for Cardiovascular MR Segmentation in Congenital Heart Disease, 2017.

Wong, Sebastien C., et al. "Understanding data augmentation for classification—when to warp? " 2016 international conference on digital image computing—techniques and applications (DICTA). IEEE, 2016.

Wordvintsev. et. al., Image Segmentation with Watershed Algorithm, Revision 43532856, 2013, 6 pages. [retrieved Jun. 8, 2021] Retrieved from the Internet <URL: https://opencv-python-tutroals.readthedocs.io/en/latest/py_tutorials/py_imgproc/py_watershed/py_watershed.html>.

Worley, K. C. et al. The common marmoset genome provides insight into primate biology and devolution. Nat. Genet. 46, 850-857 (2014).

Wu et. al., FPGA-Accelerated 3rd Generation DNA Sequencing, in IEEE Transactions on Biomedical Circuits and Systems, vol. 14, Issue 1, Feb. 2020, p. 65-74.

Wu et. al., FPGA-Based DNA Basecalling Hardware Acceleration, in Proc. IEEE 61st Int. Midwest Symp. Circuits Syst., Aug. 2018, pp. 1098-1101.

Wu, Introduction to Convolutional Neural Networks, Nanjing University, 2017.

Xie et. al., Aggregated Residual Transformations for Deep Neural Networks, in Proc. of CVPR, 2017.

(56) References Cited

OTHER PUBLICATIONS

Xie et. al., Microscopy cell counting and detection with fully convolutional regression networks, Computer methods in biomechanics and biomedical engineering, Imaging and Visualization, 6(3), pp. 283-292, 2018.

Xie, Y,. et. al., Beyond classification: structured regression for robust cell detection using convolutional neural network International conference on medical image computing and computer assisted intervention, Oct. 2015, 12 pages.

Xiong, et. al., "The human splicing code reveals new insights into the genetic determinants of disease", Jan. 9, 2015. 20 pgs.

Ye et al., BlindCal: ultra-fast base-calling of high-throughput sequencing data by blind deconvolution, Bioinformatics, vol. 30, No. 9, dated Jan. 9, 2014, pp. 1214-1219, 6 pages.

Yu et. al., Multi-Scale Context Aggregation by Dilated Convolutions, 2016.

Yue et. al., Deep Learning for Genomics: A Concise Overview, dated May 8, 2018, 40 pages.

Yue, et. al., "Deep Learning for Genomics—A Concise Overview from internet", May 8, 2018, 40 pgs.

Yuen, et. al., "Genome wide characteristics of de novo mutations in autism", Jun. 1, 2016, 10 pgs.

Zeng et. al., Causalcall: Nanopore Basecalling Using a Temporal Convolutional Network, dated Jan. 20, 2020, 11 pages.

Zhang et. al., "Template-based prediction of protein structure with deep learning", dated Jun. 2, 2020, 16 pages.

Zhang et. al., Estimating Phred scores of Illumina base calls by logistic regression and sparse modeling, BioMed Central Bioinformatics, 2017, 14 pages.

Zhang et. al., Nanopore basecalling from a perspective of instance segmentation, BMC Bioinformatics, 2020, 9 pages.

Zhang et. al., ShuffleNet: An Extremely Efficient Convolutional Neural Network for Mobile Devices, 2017.

Zhang, Jun, and Bin Liu. "PSFM-DBT—identifying DNA-binding proteins by combing position specific frequency matrix and distance-bigram transformation." International journal of molecular sciences 18.9 (2017) 1856.

Zhao et. al., Object detection with Deep Learning: A Review, dated Jul. 15, 2018, 22 pages.

Zhou et. al., Incorporating Side-Channel Information into Convolutional Neural Networks for Robotic Tasks, 2017, 7 pages.

Zhu, X. Need, A. C., Petrovski, S.& Goldstein, D. B. One gene, many neuropsychiatric disorders: lessons from Vendelian diseases. Nat. Neurosci. 17, 773-781, (2014).

Zou, et al, "A primer on deep learning in genomics", Nov. 26, 2018, 7 pages.

\* cited by examiner

ARTIFICIAL INTELLIGENCE-BASED MANY-TO-MANY BASE CALLING

PRIORITY APPLICATION

This application is a continuation of U.S. patent application Ser. No. 17/180,542, entitled "Artificial Intelligence-Based Many-To-Many Base Calling," which claims priority to and benefit of U.S. Provisional Patent Application No. 62/979,414, titled "ARTIFICIAL INTELLIGENCE-BASED MANY-TO-MANY BASE CALLING," filed 20 Feb. 2020. The priority application is hereby incorporated by reference for all purposes as if fully set forth herein.

INCORPORATIONS

The following are incorporated by reference as if fully set forth herein:

U.S. Provisional Patent Application No. 62/979,384, titled "ARTIFICIAL INTELLIGENCE-BASED BASE CALLING OF INDEX SEQUENCES," filed 20 Feb. 2020;

U.S. Provisional Patent Application No. 62/979,385, titled "KNOWLEDGE DISTILLATION-BASED COMPRESSION OF ARTIFICIAL INTELLIGENCE-BASED BASE CALLER," filed 20 Feb. 2020;

U.S. Provisional Patent Application No. 63/072,032, titled "DETECTING AND FILTERING CLUSTERS BASED ON ARTIFICIAL INTELLIGENCE-PREDICTED BASE CALLS," filed 28 Aug. 2020;

U.S. Provisional Patent Application No. 62/979,412, titled "MULTI-CYCLE CLUSTER BASED REAL TIME ANALYSIS SYSTEM," filed 20 Feb. 2020;

U.S. Provisional Patent Application No. 62/979,411, titled "DATA COMPRESSION FOR ARTIFICIAL INTELLIGENCE-BASED BASE CALLING," filed 20 Feb. 2020;

U.S. Provisional Patent Application No. 62/979,399, titled "SQUEEZING LAYER FOR ARTIFICIAL INTELLIGENCE-BASED BASE CALLING," filed 20 Feb. 2020;

U.S. Nonprovisional patent application Ser. No. 16/825,987, titled "TRAINING DATA GENERATION FOR ARTIFICIAL INTELLIGENCE-BASED SEQUENCING," filed 20 Mar. 2020;

U.S. Nonprovisional patent application Ser. No. 16/825,991 titled "ARTIFICIAL INTELLIGENCE-BASED GENERATION OF SEQUENCING METADATA," filed 20 Mar. 2020;

U.S. Nonprovisional patent application Ser. No. 16/826,126, titled "ARTIFICIAL INTELLIGENCE-BASED BASE CALLING," filed 20 Mar. 2020;

U.S. Nonprovisional patent application Ser. No. 16/826,134, titled "ARTIFICIAL INTELLIGENCE-BASED QUALITY SCORING," filed 20 Mar. 2020; and U.S. Nonprovisional patent application Ser. No. 16/826,168, titled "ARTIFICIAL INTELLIGENCE-BASED SEQUENCING," filed 21 Mar. 2020.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying deoxyribonucleic acid (DNA) because it can capture sequence motifs, which are short, recurring local patterns in DNA that are presumed to have significant biological functions. A hallmark of convolutional neural networks is the use of convolution filters.

Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, an opportunity arises to use a principled deep learning-based framework for template generation and base calling.

In the era of high-throughput technology, amassing the highest yield of interpretable data at the lowest cost per effort remains a significant challenge. Cluster-based methods of nucleic acid sequencing, such as those that utilize bridge amplification for cluster formation, have made a valuable contribution toward the goal of increasing the throughput of nucleic acid sequencing. These cluster-based methods rely on sequencing a dense population of nucleic acids immobilized on a solid support, and typically involve the use of image analysis software to deconvolve optical signals generated in the course of simultaneously sequencing multiple clusters situated at distinct locations on a solid support.

However, such solid-phase nucleic acid cluster-based sequencing technologies still face considerable obstacles that limit the amount of throughput that can be achieved. For example, in cluster-based sequencing methods, determining the nucleic acid sequences of two or more clusters that are physically too close to one another to be resolved spatially, or that in fact physically overlap on the solid support, can pose an obstacle. For example, current image analysis software can require valuable time and computational resources for determining from which of two overlapping clusters an optical signal has emanated. As a consequence, compromises are inevitable for a variety of detection platforms with respect to the quantity and/or quality of nucleic acid sequence information that can be obtained.

High density nucleic acid cluster-based genomics methods extend to other areas of genome analysis as well. For example, nucleic acid cluster-based genomics can be used in sequencing applications, diagnostics and screening, gene expression analysis, epigenetic analysis, genetic analysis of polymorphisms, and the like. Each of these nucleic acid cluster-based genomics technologies, too, is limited when there is an inability to resolve data generated from closely proximate or spatially overlapping nucleic acid clusters.

Clearly there remains a need for increasing the quality and quantity of nucleic acid sequencing data that can be obtained rapidly and cost-effectively for a wide variety of uses, including for genomics (e.g., for genome characterization of any and all animal, plant, microbial or other biological species or populations), pharmacogenomics, transcriptomics, diagnostics, prognostics, biomedical risk assessment, clinical and research genetics, personalized medicine, drug efficacy and drug interactions assessments, veterinary medicine, agriculture, evolutionary and biodiversity studies, aquaculture, forestry, oceanography, ecological and environmental management, and other purposes.

The technology disclosed provides neural network-based methods and systems that address these and similar needs, including increasing the level of throughput in high-throughput nucleic acid sequencing technologies, and offers other related advantages.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which.

DETAILED DESCRIPTION

Figure 1A:
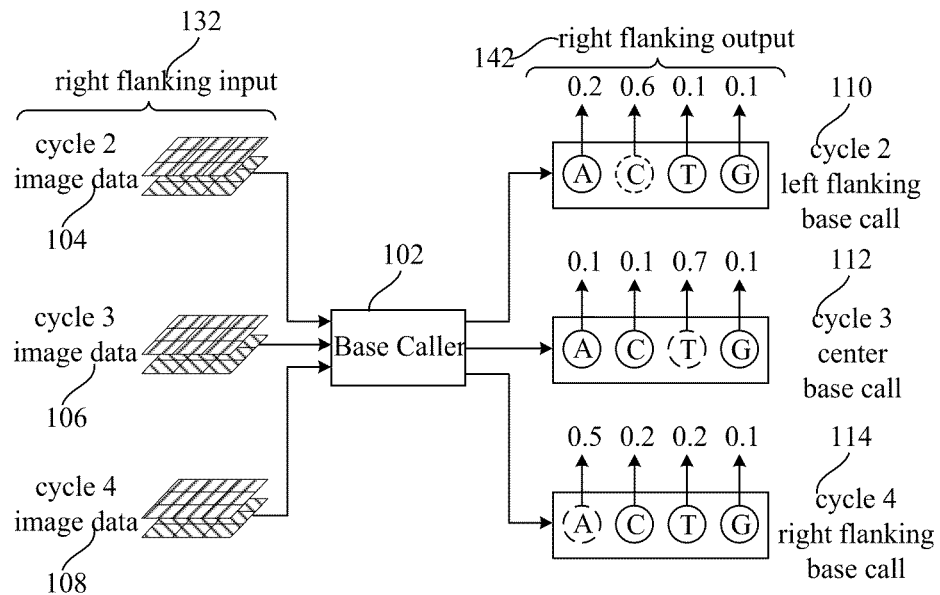
FIGS. 1A, 1B, and 1C show the disclosed many-to-many base calling.

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

Sequencing Images

Base calling is the process of determining the nucleotide composition of a sequence. Base calling involves analyzing image data, i.e., sequencing images, produced during a sequencing run (or sequencing reaction) carried out by a sequencing instrument such as Illumina's iSeq, HiSeqX, HiSeq 3000, HiSeq 4000, HiSeq 2500, NovaSeq 6000, NextSeq 550, NextSeq 1000, NextSeq 2000, NextSeqDx, MiSeq, and MiSeqDx.

The following discussion outlines how the sequencing images are generated and what they depict, in accordance with one implementation.

Base calling decodes the intensity data encoded in the sequencing images into nucleotide sequences. In one implementation, the Illumina sequencing platforms employ cyclic reversible termination (CRT) chemistry for base calling. The process relies on growing nascent strands complementary to template strands with fluorescently-labeled nucleotides, while tracking the emitted signal of each newly added nucleotide. The fluorescently-labeled nucleotides have a 3' removable block that anchors a fluorophore signal of the nucleotide type.

Sequencing occurs in repetitive cycles, each comprising three steps: (a) extension of a nascent strand by adding the fluorescently-labeled nucleotide; (b) excitation of the fluorophore using one or more lasers of an optical system of the sequencing instrument and imaging through different filters of the optical system, yielding the sequencing images; and (c) cleavage of the fluorophore and removal of the 3' block in preparation for the next sequencing cycle. Incorporation and imaging cycles are repeated up to a designated number of sequencing cycles, defining the read length. Using this approach, each cycle interrogates a new position along the template strands.

The tremendous power of the Illumina sequencers stems from their ability to simultaneously execute and sense millions or even billions of clusters (also called "analytes") undergoing CRT reactions. A cluster comprises approximately one thousand identical copies of a template strand, though clusters vary in size and shape. The clusters are grown from the template strand, prior to the sequencing run, by bridge amplification or exclusion amplification of the input library. The purpose of the amplification and cluster growth is to increase the intensity of the emitted signal since the imaging device cannot reliably sense fluorophore signal of a single strand. However, the physical distance of the strands within a cluster is small, so the imaging device perceives the cluster of strands as a single spot.

Sequencing occurs in a flow cell (or biosensor)—a small glass slide that holds the input strands. The flow cell is connected to the optical system, which comprises microscopic imaging, excitation lasers, and fluorescence filters. The flow cell comprises multiple chambers called lanes. The lanes are physically separated from each other and may contain different tagged sequencing libraries, distinguishable without sample cross contamination. In some implementations, the flow cell comprises a patterned surface. A "patterned surface" refers to an arrangement of different regions in or on an exposed layer of a solid support.

The imaging device of the sequencing instrument (e.g., a solid-state imager such as a charge-coupled device (CCD) or a complementary metal-oxide-semiconductor (CMOS) sensor) takes snapshots at multiple locations along the lanes in a series of non-overlapping regions called tiles. For example, there can be sixty four or ninety six tiles per lane. A tile holds hundreds of thousands to millions of clusters.

The output of the sequencing run is the sequencing images. Sequencing images depict intensity emissions of the clusters and their surrounding background using a grid (or array) of pixelated units (e.g., pixels, superpixels, subpixels). The intensity emissions are stored as intensity values of the pixelated units. The sequencing images have dimensions w×h of the grid of pixelated units, where w (width) and h (height) are any numbers ranging from 1 and 100,000 (e.g., 115×115, 200×200, 1800×2000, 2200×25000, 2800×3600, 4000×400). In some implementations, w and h are the same. In other implementations, w and h are different. The sequencing images depict intensity emissions generated as a result of nucleotide incorporation in the nucleotide sequences during the sequencing run. The intensity emissions are from associated clusters and their surrounding background.

Neural Network-Based Base Calling

The following discussion focuses on a neural network-based base caller 102 described herein. First, the input to the neural network-based base caller 102 is described, in accordance with one implementation. Then, examples of the structure and form of the neural network-based base caller 102 are provided. Finally, the output of the neural network-based base caller 102 is described, in accordance with one implementation.

A data flow logic provides the sequencing images to the neural network-based base caller 102 for base calling. The neural network-based base caller 102 accesses the sequencing images on a patch-by-patch basis (or a tile-by-tile basis). Each of the patches is a sub-grid (or sub-array) of pixelated units in the grid of pixelated units that forms the sequencing images. The patches have dimensions q×r of the sub-grid of pixelated units, where q (width) and r (height) are any numbers ranging from 1 and 10000 (e.g., 3×3, 5×5, 7×7, 10×10, 15×15, 25×25, 64×64, 78×78, 115×115). In some implementations, q and r are the same. In other implementations, q and r are different. In some implementations, the patches extracted from a sequencing image are of the same size. In other implementations, the patches are of different sizes. In some implementations, the patches can have overlapping pixelated units (e.g., on the edges).

Sequencing produces m sequencing images per sequencing cycle for corresponding m image channels. That is, each of the sequencing images has one or more image (or intensity) channels (analogous to the red, green, blue (RGB)

channels of a color image). In one implementation, each image channel corresponds to one of a plurality of filter wavelength bands. In another implementation, each image channel corresponds to one of a plurality of imaging events at a sequencing cycle. In yet another implementation, each image channel corresponds to a combination of illumination with a specific laser and imaging through a specific optical filter. The image patches are tiled (or accessed) from each of the m image channels for a particular sequencing cycle. In different implementations such as 4-, 2-, and 1-channel chemistries, m is 4 or 2. In other implementations, m is 1, 3, or greater than 4.

Consider, for example, that a sequencing run is implemented using two different image channels: a blue channel and a green channel. Then, at each sequencing cycle, the sequencing run produces a blue image and a green image. This way, for a series of k sequencing cycles of the sequencing run, a sequence of k pairs of blue and green images is produced as output and stored as the sequencing images. Accordingly, a sequence of k pairs of blue and green image patches is generated for the patch-level processing by the neural network-based base caller 102.

The input image data to the neural network-based base caller 102 for a single iteration of base calling (or a single instance of forward pass or a single forward traversal) comprises data for a sliding window of multiple sequencing cycles. The sliding window can include, for example, a current sequencing cycle, one or more preceding sequencing cycles, and one or more successive sequencing cycles.

In one implementation, the input image data comprises data for three sequencing cycles, such that data for a current (time t) sequencing cycle to be base called is accompanied with (i) data for a left flanking/context/previous/preceding/prior (time t−1) sequencing cycle and (ii) data for a right flanking/context/next/successive/subsequent (time t+1) sequencing cycle.

In another implementation, the input image data comprises data for five sequencing cycles, such that data for a current (time t) sequencing cycle to be base called is accompanied with (i) data for a first left flanking/context/previous/preceding/prior (time t−1) sequencing cycle, (ii) data for a second left flanking/context/previous/preceding/prior (time t−2) sequencing cycle, (iii) data for a first right flanking/context/next/successive/subsequent (time t+1), and (iv) data for a second right flanking/context/next/successive/subsequent (time t+2) sequencing cycle.

In yet another implementation, the input image data comprises data for seven sequencing cycles, such that data for a current (time t) sequencing cycle to be base called is accompanied with (i) data for a first left flanking/context/previous/preceding/prior (time t−1) sequencing cycle, (ii) data for a second left flanking/context/previous/preceding/prior (time t−2) sequencing cycle, (iii) data for a third left flanking/context/previous/preceding/prior (time t−3) sequencing cycle, (iv) data for a first right flanking/context/next/successive/subsequent (time t+1), (v) data for a second right flanking/context/next/successive/subsequent (time t+2) sequencing cycle, and (vi) data for a third right flanking/context/next/successive/subsequent (time t+3) sequencing cycle. In other implementations, the input image data comprises data for a single sequencing cycle. In yet other implementations, the input image data comprises data for 10, 15, 20, 30, 58, 75, 92, 130, 168, 175, 209, 225, 230, 275, 318, 325, 330, 525, or 625 sequencing cycles.

The neural network-based base caller 102 processes the image patches through its convolution layers and produces an alternative representation, according to one implementation. The alternative representation is then used by an output layer (e.g., a softmax layer) for generating a base call for either just the current (time t) sequencing cycle or each of the sequencing cycles, i.e., the current (time t) sequencing cycle, the first and second preceding (time t−1, time t−2) sequencing cycles, and the first and second succeeding (time t+1, time t+2) sequencing cycles. The resulting base calls form the sequencing reads.

In one implementation, the neural network-based base caller 102 outputs a base call for a single target cluster for a particular sequencing cycle. In another implementation, the neural network-based base caller 102 outputs a base call for each target cluster in a plurality of target clusters for the particular sequencing cycle. In yet another implementation, the neural network-based base caller 102 outputs a base call for each target cluster in a plurality of target clusters for each sequencing cycle in a plurality of sequencing cycles, thereby producing a base call sequence for each target cluster.

In one implementation, the neural network-based base caller 102 is a multilayer perceptron (MLP). In another implementation, the neural network-based base caller 102 is a feedforward neural network. In yet another implementation, the neural network-based base caller 102 is a fully-connected neural network. In a further implementation, the neural network-based base caller 102 is a fully convolution neural network. In yet further implementation, the neural network-based base caller 102 is a semantic segmentation neural network. In yet another further implementation, the neural network-based base caller 102 is a generative adversarial network (GAN).

In one implementation, the neural network-based base caller 102 is a convolution neural network (CNN) with a plurality of convolution layers. In another implementation, the neural network-based base caller 102 is a recurrent neural network (RNN) such as a long short-term memory network (LSTM), bi-directional LSTM (Bi-LSTM), or a gated recurrent unit (GRU). In yet another implementation, the neural network-based base caller 102 includes both a CNN and an RNN.

In yet other implementations, the neural network-based base caller 102 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The neural network-based base caller 102 can use one or more loss functions such as logistic regression/log loss, multi-class cross-entropy/softmax loss, binary cross-entropy loss, mean-squared error loss, L1 loss, L2 loss, smooth L1 loss, and Huber loss. The neural network-based base caller 102 can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The neural network-based base caller 102 can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The neural network-based base caller 102 is trained using backpropagation-based gradient update techniques. Example gradient descent techniques that can be used for training the neural network-based base caller 102 include stochastic gradient descent, batch gradient descent, and mini-batch gradient descent. Some examples of gradient descent optimization algorithms that can be used to train the neural network-based base caller 102 are Momentum, Nesterov accelerated gradient, Adagrad, Adadelta, RMSprop, Adam, AdaMax, Nadam, and AMSGrad.

In one implementation, the neural network-based base caller 102 uses a specialized architecture to segregate processing of data for different sequencing cycles. The motivation for using the specialized architecture is described first. As discussed above, the neural network-based base caller 102 processes image patches for a current sequencing cycle, one or more preceding sequencing cycles, and one or more successive sequencing cycles. Data for additional sequencing cycles provides sequence-specific context. The neural network-based base caller 102 learns the sequence-specific context during training and base calls them. Furthermore, data for pre and post sequencing cycles provides second order contribution of pre-phasing and phasing signals to the current sequencing cycle.

However, images captured at different sequencing cycles and in different image channels are misaligned and have residual registration error with respect to each other. To account for this misalignment, the specialized architecture comprises spatial convolution layers that do not mix information between sequencing cycles and only mix information within a sequencing cycle.

Spatial convolution layers (or spatial logic) use so-called "segregated convolutions" that operationalize the segregation by independently processing data for each of a plurality of sequencing cycles through a "dedicated, non-shared" sequence of convolutions. The segregated convolutions convolve over data and resulting feature maps of only a given sequencing cycle, i.e., intra-cycle, without convolving over data and resulting feature maps of any other sequencing cycle.

Consider, for example, that the input image data comprises (i) current image patch for a current (time t) sequencing cycle to be base called, (ii) previous image patch for a previous (time t−1) sequencing cycle, and (iii) next image patch for a next (time t+1) sequencing cycle. The specialized architecture then initiates three separate convolution pipelines, namely, a current convolution pipeline, a previous convolution pipeline, and a next convolution pipeline. The current data processing pipeline receives as input the current image patch for the current (time t) sequencing cycle and independently processes it through a plurality of spatial convolution layers to produce a so-called "current spatially convolved representation" as the output of a final spatial convolution layer. The previous convolution pipeline receives as input the previous image patch for the previous (time t−1) sequencing cycle and independently processes it through the plurality of spatial convolution layers to produce a so-called "previous spatially convolved representation" as the output of the final spatial convolution layer. The next convolution pipeline receives as input the next image patch for the next (time t+1) sequencing cycle and independently processes it through the plurality of spatial convolution layers to produce a so-called "next spatially convolved representation" as the output of the final spatial convolution layer.

In some implementations, the current, previous, and next convolution pipelines are executed in parallel. In some implementations, the spatial convolution layers are part of a spatial convolution network (or subnetwork) within the specialized architecture.

The neural network-based base caller 102 further comprises temporal convolution layers (or temporal logic) that mix information between sequencing cycles, i.e., inter-cycles. The temporal convolution layers receive their inputs from the spatial convolution network and operate on the spatially convolved representations produced by the final spatial convolution layer for the respective data processing pipelines.

The inter-cycle operability freedom of the temporal convolution layers emanates from the fact that the misalignment property, which exists in the image data fed as input to the spatial convolution network, is purged out from the spatially convolved representations by the stack, or cascade, of segregated convolutions performed by the sequence of spatial convolution layers.

Temporal convolution layers use so-called "combinatory convolutions" that groupwise convolve over input channels in successive inputs on a sliding window basis. In one implementation, the successive inputs are successive outputs produced by a previous spatial convolution layer or a previous temporal convolution layer.

In some implementations, the temporal convolution layers are part of a temporal convolution network (or subnetwork) within the specialized architecture. The temporal convolution network receives its inputs from the spatial convolution network. In one implementation, a first temporal convolution layer of the temporal convolution network groupwise combines the spatially convolved representations between the sequencing cycles. In another implementation, subsequent temporal convolution layers of the temporal convolution network combine successive outputs of previous temporal convolution layers. The output of the final temporal convolution layer is fed to an output layer that produces an output. The output is used to base call one or more clusters at one or more sequencing cycles.

The data flow logic provides per-cycle cluster data to the neural network-based base caller 102. The per-cycle cluster data is for a plurality of clusters and for a first subset of sequencing cycles of a sequencing run. Consider, for example, that the sequencing run has 150 sequencing cycles. The first subset of sequencing cycles can then include any subset of the 150 sequencing cycles, for example, the first 5, 10, 15, 25, 35, 40, 50, or 100 sequencing cycles of the 150-cycle sequencing run. Also, each sequencing cycle produces sequencing images that depict intensity emissions of clusters in the plurality of clusters. This way, the per-cycle cluster data for the plurality of clusters and for the first subset of sequencing cycles of the sequencing run includes sequencing images only for the first 5, 10, 15, 25, 35, 40, 50, or 100 sequencing cycles of the 150-cycle sequencing run and does not include sequencing images for the remainder sequencing cycles of the 150-cycle sequencing run.

The neural network-based base caller 102 base calls each cluster in the plurality of clusters at each sequencing cycle in the first subset of sequencing cycles. To do so, the neural network-based base caller 102 processes the per-cycle cluster data and generates intermediate representations of the per-cycle cluster data. Then, the neural network-based base caller 102 processes the intermediate representations though an output layer and produces a per-cluster, per-cycle probability quadruple for each cluster and for each sequencing cycle. Examples of the output layer include a softmax function, a log-softmax function, an ensemble output average function, a multi-layer perceptron uncertainty function, a Bayes Gaussian distribution function, and a cluster intensity function. The per-cluster, per-cycle probability quadruples are stored as the probability quadruples and referred to herein as "base-wise likelihoods" because there are four nucleotide bases A, C, T, and G.

Softmax function is a preferred function for multi-class classification. The softmax function calculates the probabilities of each target class over all possible target classes. The output range of the softmax function is between zero and one and the sum of all the probabilities is equal to one. The softmax function computes the exponential of the given input value and the sum of exponential values of all the input values. The ratio of the exponential of the input value and the sum of exponential values is the output of the softmax function, referred to herein as "exponential normalization."

Formally, training a so-called softmax classifier is regression to a class probability, rather than a true classifier as it does not return the class but rather a confidence prediction of each class's probability. The softmax function takes a class of values and converts them to probabilities that sum to one. The softmax function squashes a n-dimensional vector of arbitrary real values to n-dimensional vector of real values within the range zero to one. Thus, using the softmax function ensures that the output is a valid, exponentially normalized probability mass function (nonnegative and summing to one).

Intuitively, the softmax function is a "soft" version of the maximum function. The term "soft" derives from the fact that the softmax function is continuous and differentiable. Instead of selecting one maximal element, it breaks the vector into parts of a whole with the maximal input element getting a proportionally larger value, and the other getting a less proportion of the value. The property of outputting a probability distribution makes the softmax function suitable for probabilistic interpretation in classification tasks.

Let us consider z as a vector of inputs to the softmax layer. The softmax layer units are the number of nodes in the softmax layer and therefore, the length of the z vector is the number of units in the softmax layer (if we have ten output units, then there are ten z elements).

For an n-dimensional vector $Z=[z_1, z_2, \ldots z_n]$, the softmax function uses exponential normalization (exp) to produce another n-dimensional vector p(Z) with normalized values in the range [0, 1] and that add to unity:

$$Z = \begin{bmatrix} z_1 \\ z_2 \\ \vdots \\ z_n \end{bmatrix} \text{ and, } p(Z) \to \begin{bmatrix} p_1 \\ p_2 \\ \vdots \\ p_n \end{bmatrix}$$

$$p_j = \frac{\exp^{z_j}}{\sum_{k=1}^{n} \exp^{z_k}} \forall j \in 1, 2, \ldots, n$$

For example, a softmax function is applied to three classes as $$z \mapsto \textit{soft}\max\left(\left[z; \frac{z}{10}; -2z\right]\right).$$

Note that the three outputs always sum to one. They thus define a discrete probability mass function.

A particular per-cluster, per-cycle probability quadruple identifies probabilities of a base incorporated in a particular cluster at a particular sequencing cycle being A, C, T, and G. When the output layer of the neural network-based base caller 102 uses a softmax function, the probabilities in the per-cluster, per-cycle probability quadruple are exponentially normalized classification scores that sum to unity.

In one implementation, the method includes processing the convolved representation through the output layer to produce likelihoods of a base incorporated in the target analyte at the current sequencing cycle being A, C, T, and G, and classifying the base as A, C, T, or G based on the likelihoods. In one implementation, the likelihoods are exponentially normalized scores produced by a softmax layer.

In one implementation, the method includes deriving, from the output, an output pair for the target analyte that identifies a class label of a base incorporated in the target analyte at the current sequencing cycle being A, C, T, or G, and base calling the target analyte based on the class label. In one implementation, a class label of 1, 0 identifies an A base, a class label of 0, 1 identifies a C base, a class label of 1, 1 identifies a T base, and a class label of 0, 0 identifies a G base. In another implementation, a class label of 1, 1 identifies an A base, a class label of 0, 1 identifies a C base, a class label of 0.5, 0.5 identifies a T base, and a class label of 0, 0 identifies a G base. In yet another implementation, a class label of 1, 0 identifies an A base, a class label of 0, 1 identifies a C base, a class label of 0.5, 0.5 identifies a T base, and a class label of 0, 0 identifies a G base. In yet further implementation, a class label of 1, 2 identifies an A base, a class label of 0, 1 identifies a C base, a class label of 1, 1 identifies a T base, and a class label of 0, 0 identifies a G base. In one implementation, the method includes deriving, from the output, a class label for the target analyte that identifies a base incorporated in the target analyte at the current sequencing cycle being A, C, T, or G, and base calling the target analyte based on the class label. In one implementation, a class label of 0.33 identifies an A base, a class label of 0.66 identifies a C base, a class label of 1 identifies a T base, and a class label of 0 identifies a G base. In another implementation, a class label of 0.50 identifies an A base, a class label of 0.75 identifies a C base, a class label of 1 identifies a T base, and a class label of 0.25 identifies a G base. In one implementation, the method includes deriving, from the output, a single output value, comparing the single output value against class value ranges corresponding to bases A, C, T, and G, based on the comparing, assigning the single output value to a particular class value range, and base calling the target analyte based on the assigning. In one implementation, the single output value is derived using a sigmoid function, and the single output value ranges from 0 to 1. In another implementation, a class value range of 0-0.25 represents an A base, a class value range of 0.25-0.50 represents a C base, a class value range of 0.50-0.75 represents a T base, and a class value range of 0.75-1 represents a G base.

Additional details about the neural network-based base caller 102 can be found in U.S. Provisional Patent Application No. 62/821,766, titled "ARTIFICIAL INTELLIGENCE-BASED SEQUENCING,", filed on Mar. 21, 2019, which is incorporated herein by reference.

Many-to-Many Base Calling

The technology disclosed causes the neural network-based base caller 102 to generate, for a given window of input, base calls not only for the center sequencing cycle but also for the flanking sequencing cycles, in accordance with one implementation. That is, in one implementation, the technology disclosed simultaneously generates base calls for cycle N, cycle N+1, cycle N−1, cycle N+2, cycle N−2, and so on for a given input window. That is, a single forward propagation/traversal/base calling iteration of the neural network-based base caller 102 generates base calls for multiple sequencing cycles in the input window of sequencing cycles, which is referred to herein as "many-to-many base calling."

The technology disclosed then uses the disclosed many-to-many base calling to generate multiple base calls for a same target sequencing cycle that appeared across multiple sliding windows of inputs. For example, the target sequencing cycle can appear at different positions in the multiple sliding windows of inputs (e.g., starting at position N+2 in the first sliding window, progressing to position N+1 in the second sliding window, and finishing at position N in the third sliding window).

Base calling the target sequencing cycle multiple times produces multiple candidates of the correct base call for the target sequencing cycle. The technology disclosed then evaluates the multiple candidates of the correct base call as an aggregate and determines a final base call for the target sequencing cycle. The final base call for the target sequencing cycle can be selected using aggregate-analysis techniques like averaging, consensus, and weighted consensus.

Figure 1B:
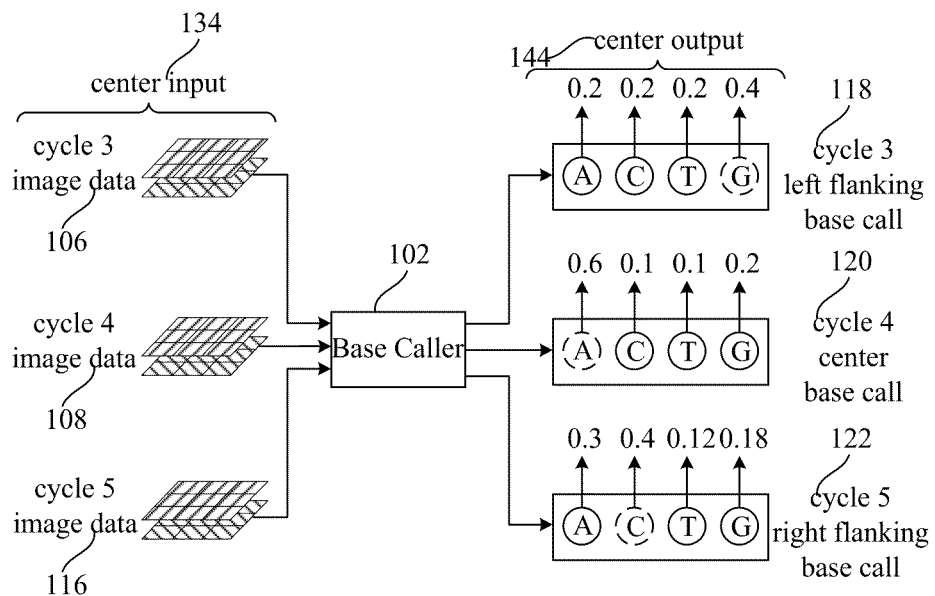
Figure 1C:
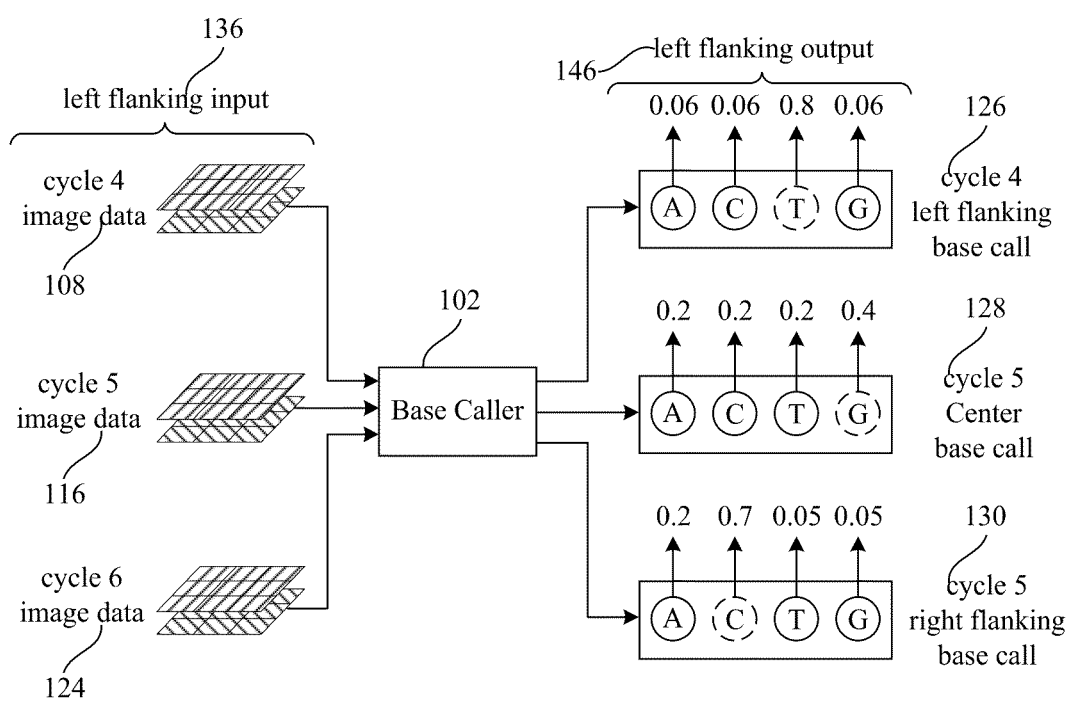

FIGS. 1A, 1B, and 1C show the disclosed many-to-many base calling 100. The neural network-based base caller 102 (i.e., the base caller 102) processes at least right flanking, center, and left flanking inputs, and produces at least right flanking, center, and left flanking outputs, in accordance with one implementation of the technology disclosed.

The many-to-many base calling 100 is configured to provide data for n number of sequencing cycles as input to the base caller 102 and generate base calls for any number of cycles in the n number of cycles in one iteration of base calling (i.e., one forward pass instance). A target sequencing cycle 108 can be base called n number of times and can appear/occur/fall at various positions in the n number of times of the base calling iterations.

The target sequencing cycle 108 can be the center sequencing cycle (FIG. 1B) in some base calling iterations. In other iterations, the target sequencing cycle 108 can be the right flanking/context sequencing cycle (FIG. 1A) adjacent to the center sequencing cycle or can be the left flanking/context sequencing cycle adjacent (FIG. 1C) to the center sequencing cycle. The right or left offset from the center sequencing cycle can also vary. That is, the target sequencing cycle 108 in the n number of times of the base calling iterations can fall either at the center position, immediately to the right of the center position, immediately to the left of the center position, at any offset to the right of the center position, at any offset to the left of the center position, or at any other position in the n number of times of the base calling iterations. The base calling iterations for the target sequencing cycle can have inputs of varying lengths of sequencing cycles sand also multiple base calling outputs for various lengths of sequencing cycles in a given input window of sequencing cycles.

In one implementation, the technology disclosed includes accessing a progression of per-cycle analyte channel sets generated for sequencing cycles of a sequencing run, processing, through the neural network-based base caller 102, windows of per-cycle analyte channel sets in the progression for the windows of sequencing cycles of the sequencing run such that the neural network-based base caller processes 102 a subject window of per-cycle analyte channel sets in the progression for the subject window of sequencing cycles of the sequencing run and generates provisional base call predictions for three or more sequencing cycles in the subject window of sequencing cycles, from multiple windows in which a particular sequencing cycle appeared at different positions, using the neural network-based base caller 102 to generate provisional base call predictions for the particular sequencing cycle, and determining a base call for the particular sequencing cycle based on the provisional base call predictions.

In one implementation, the technology disclosed includes accessing a series of per-cycle analyte channel sets generated for sequencing cycles of a sequencing run, processing, through the neural network-based base caller 102, windows of per-cycle analyte channel sets in the series for the windows of sequencing cycles of the sequencing run such that the neural network-based base caller 102 processes a subject window of per-cycle analyte channel sets in the series for the subject window of sequencing cycles of the sequencing run and generates base call predictions for two or more sequencing cycles in the subject window of sequencing cycles, and processing, through the neural network-based base caller 102, a plurality of the windows of per-cycle analyte channel sets in the series for the plurality of the windows of sequencing cycles of the sequencing run and generating an output for each window in the plurality of the windows.

Each window in the plurality of the windows can include a particular per-cycle analyte channel set for a particular sequencing cycle of the sequencing run. The output for each window in the plurality of the windows includes (i) a base call prediction for the particular sequencing cycle and (ii) one or more additional base call predictions for one or more additional sequencing cycles of the sequencing run, thereby generating a plurality of base call predictions for the particular sequencing cycle across the plurality of the windows (for example, generated in parallel or simultaneously by an output layer). Finally, the technology disclosed includes determining a base call for the particular sequencing cycle based on the plurality of base call predictions.

The right flanking input 132 comprises current image data 108 for a current sequencing cycle (e.g., cycle 4) of a sequencing run, supplemented with previous image data 104 and 106 for one or more previous sequencing cycles (e.g., cycles 2 and 3) preceding the current sequencing cycle. The right flanking output 142 comprises a right flanking base call prediction 114 for the current sequencing cycle and base call predictions 110 and 112 for the previous sequencing cycles.

The center input 134 comprises the current image data 108, supplemented with the previous image data 106 (e.g., cycle 3) and successive image data 116 for one or more successive sequencing cycles (e.g., cycle 5) succeeding the current sequencing cycle. The center output 144 comprises a center base call prediction 120 for the current sequencing cycle and base call predictions 118 and 122 for the previous sequencing cycles and the successive sequencing cycles.

The left flanking input 136 comprises the current image data 108, supplemented with the successive image data 116 and 124. The left flanking output 146 comprises a left flanking base call prediction 126 for the current sequencing cycle and base call predictions 128 and 130 for the successive sequencing cycles (e.g., cycles 5 and 6).

Figure 1D:
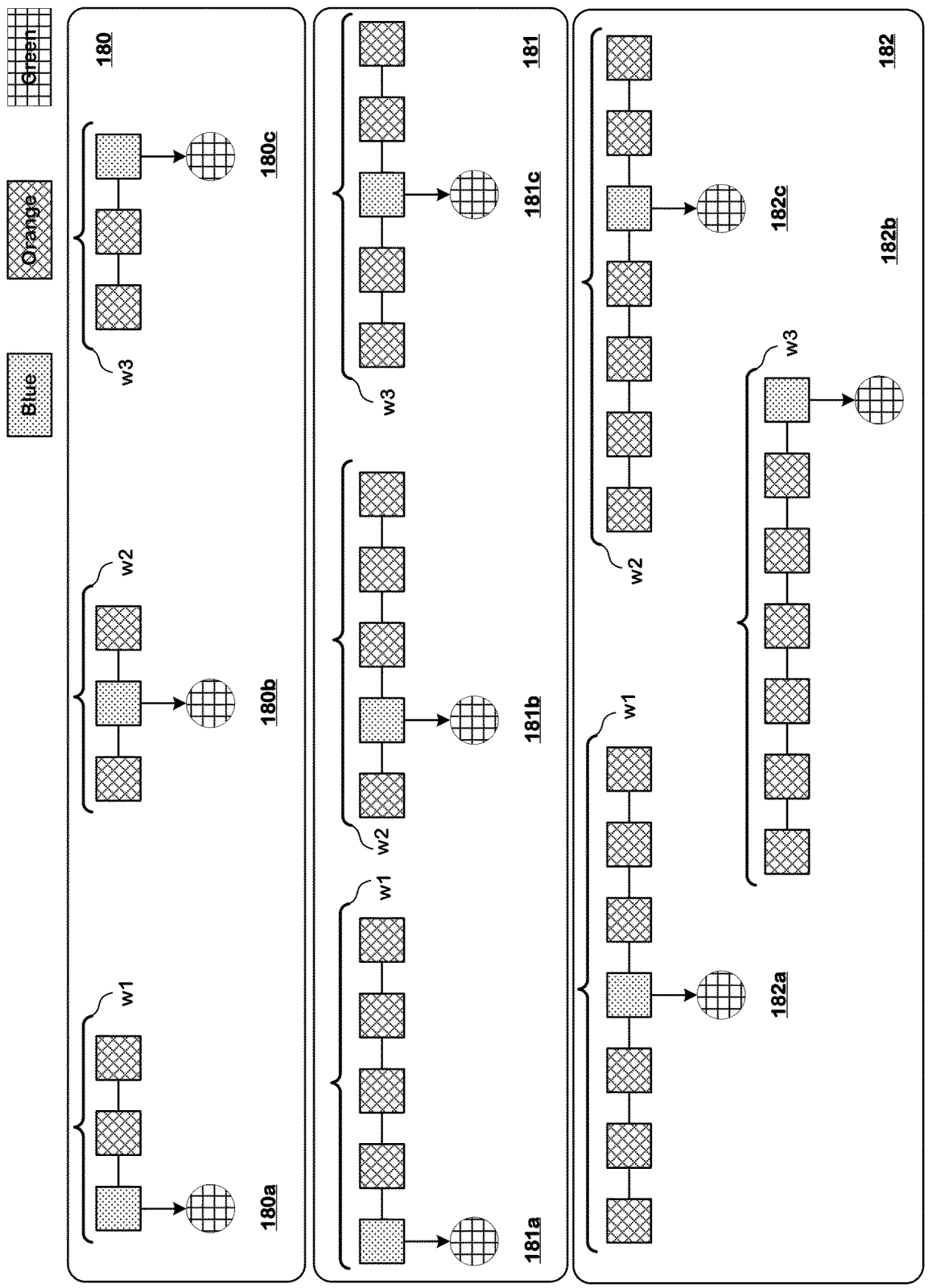
FIGS. 1D and 1E illustrate different examples of the disclosed many-to-many base calling.
Figure 1E:
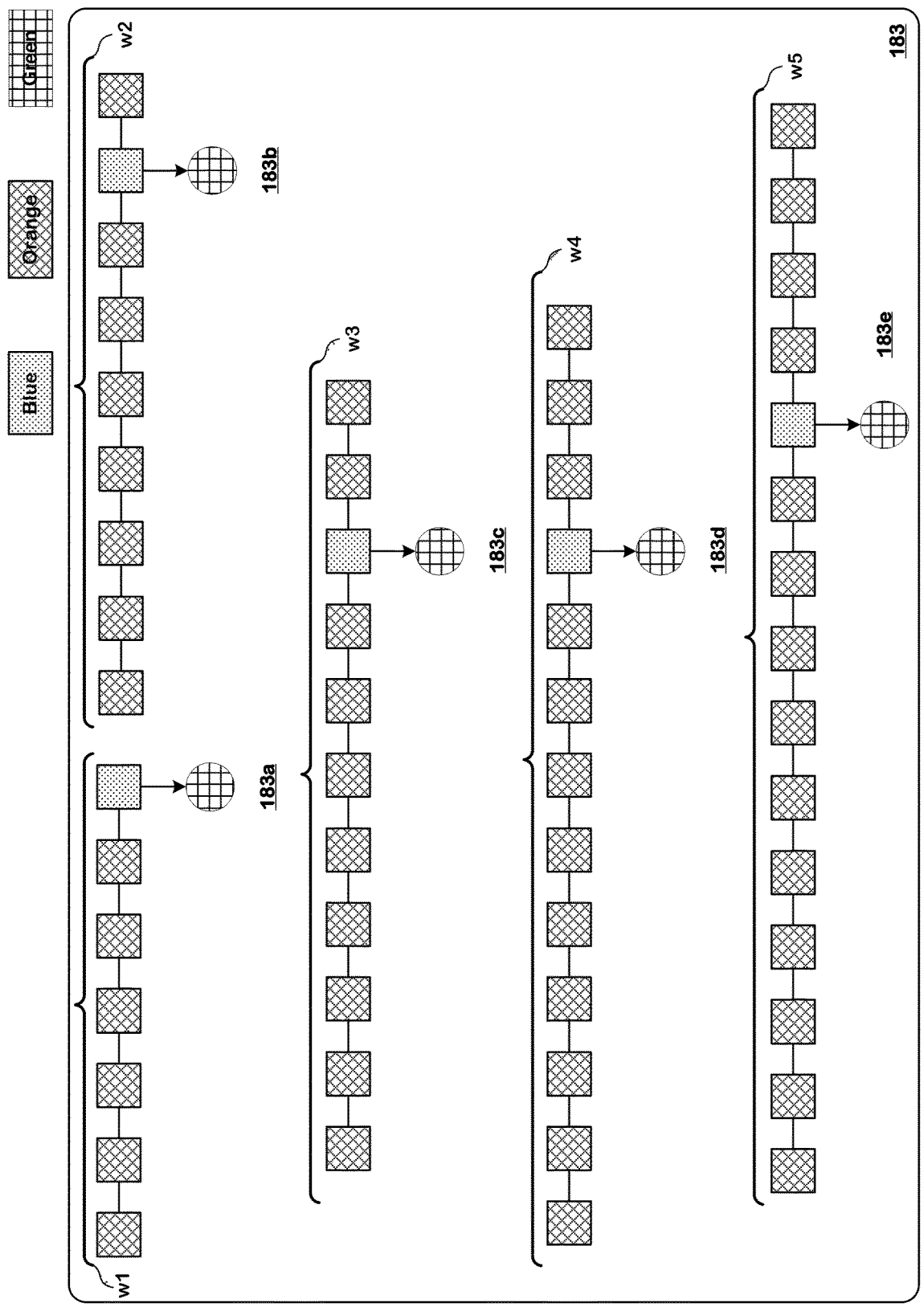

FIGS. 1D and 1E illustrate different examples of the disclosed many-to-many base calling. In FIGS. 1D and 1E, the blue box represents the particular or target sequencing cycle (or data therefor). The particular sequencing cycle is also considered a current sequencing cycle is various implementations of the technology disclosed. The orange boxes represent sequencing cycles (or data therefor) different than the particular sequencing cycle. The green circles represent one or more base calls generated for the particular sequencing cycle. The base calls can be generated by any base caller, such as Illumina's Real-Time Analysis (RTA) software or the disclosed neural network-based base caller 102. The data for the sequencing cycles can be images or some other type of input data, such as current readings, voltage changes, pH scale data, and so on.

Turning to FIG. 1D, the first many-to-many base calling example 180 shows three base calling iterations 180a, 180b, and 180c and corresponding three input windows/groups of sequencing cycles w1, w2, and w3 (or data therefore). In one implementation, the base calling iterations produce base calls for each sequencing cycle in the corresponding input window of sequencing cycles. In another implementation, the base calling iterations produce base calls for only some of the sequencing cycles in the corresponding input window of sequencing cycles (e.g., only the particular sequencing cycle). Also, the particular sequencing cycle can appear at different positions in the input windows/groups of sequencing cycles w1, w2, and w3. In other implementations (not shown), two or more input windows/groups of sequencing cycles can have the particular sequencing cycle at a same position. Furthermore, the input windows/groups of sequencing cycles w1, w2, and w3 have the particular sequencing cycle as at least one overlapping cycle, and also have one or more non-overlapping cycles. That is, orange boxes at different positions in different input windows/group of sequencing cycles represent different non-overlapping cycles. Finally, the three base calling iterations 180a, 180b, and 180c generate three base calls (i.e., the three green circles) for the particular sequencing cycle, which can be considered provisional base calls and subsequently analyzed as an aggregate to make a final base call for the particular sequencing cycle. Different examples of analysis are described later in FIGS. 2, 3, and 4.

The second and third examples of many-to-many base calling 181 and 182 illustrate that the particular sequencing cycle can be at any position in the input windows/group of sequencing cycles and have any number of right and left flanking cycles or no flanking cycles at all (e.g., the third window (w3) in the third many-to-many base calling example 182. The three base calling iterations 181a, 181b, and 181c generate three base calls (i.e., the three green circles) for the particular sequencing cycle, which can be considered provisional base calls and subsequently analyzed as an aggregate to make a final base call for the particular sequencing cycle. Different examples of analysis are described later in FIGS. 2, 3, and 4. The three base calling iterations 182a, 182b, and 182c generate three base calls (i.e., the three green circles) for the particular sequencing cycle, which can be considered provisional base calls and subsequently analyzed as an aggregate to make a final base call for the particular sequencing cycle. Different examples of analysis are described later in FIGS. 2, 3, and 4.

FIG. 1E illustrates a many-to-many base calling example 183 with five base calling iterations 183a-e, each of which generates a base call prediction for the particular sequencing cycles by processing five respective windows/sets/groups of input data in which data for the particular sequencing cycle occurs at different positions. The five base calling iterations 183a-e generate five base calls (i.e., the five green circles) for the particular sequencing cycle, which can be considered provisional base calls and subsequently analyzed as an aggregate to make a final base call for the particular sequencing cycle. Different examples of analysis are described later in FIGS. 2, 3, and 4.

Figure 2:
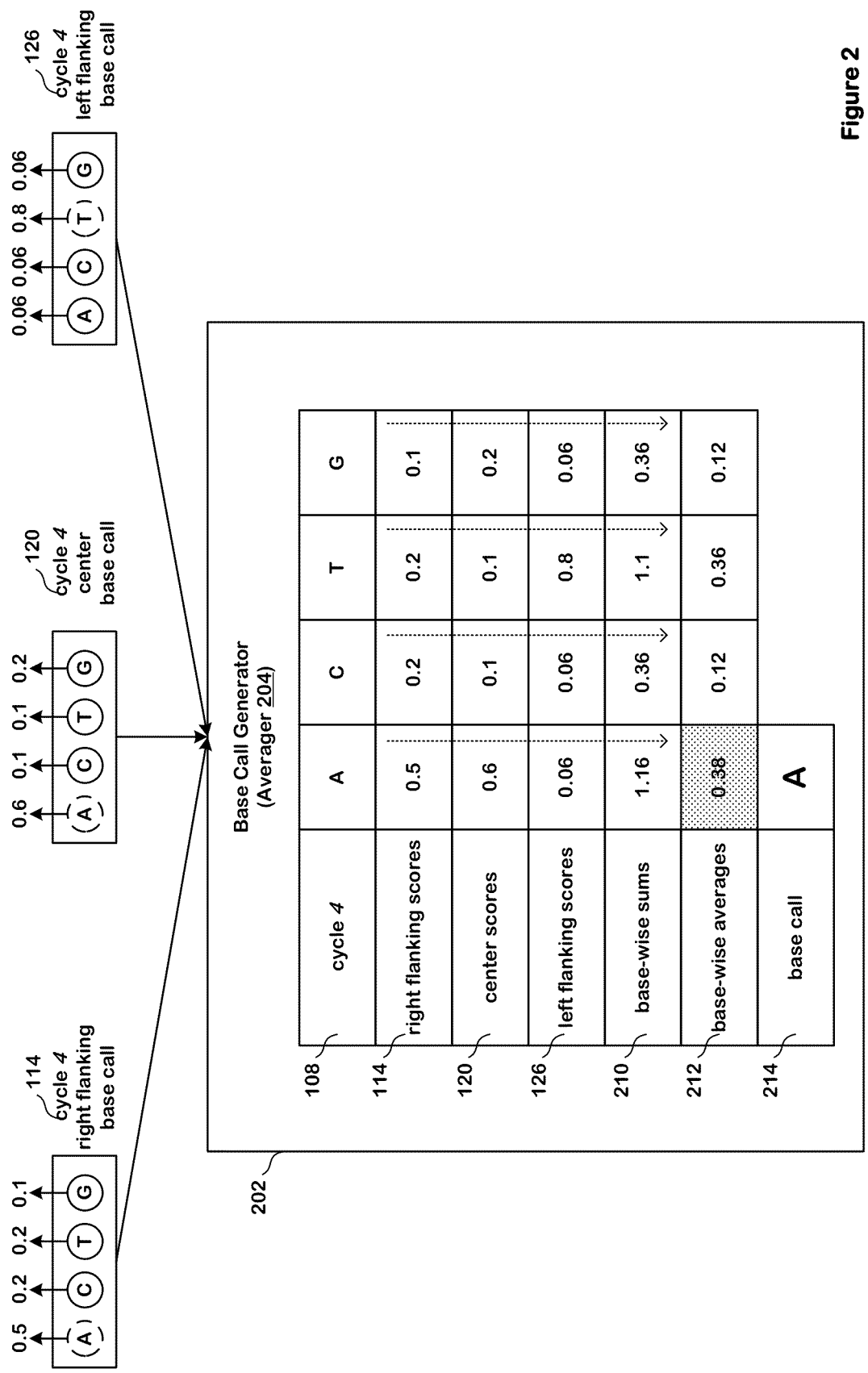
FIGS. 2, 3, and 4 show different implementations of a base call generator.
Figure 3:
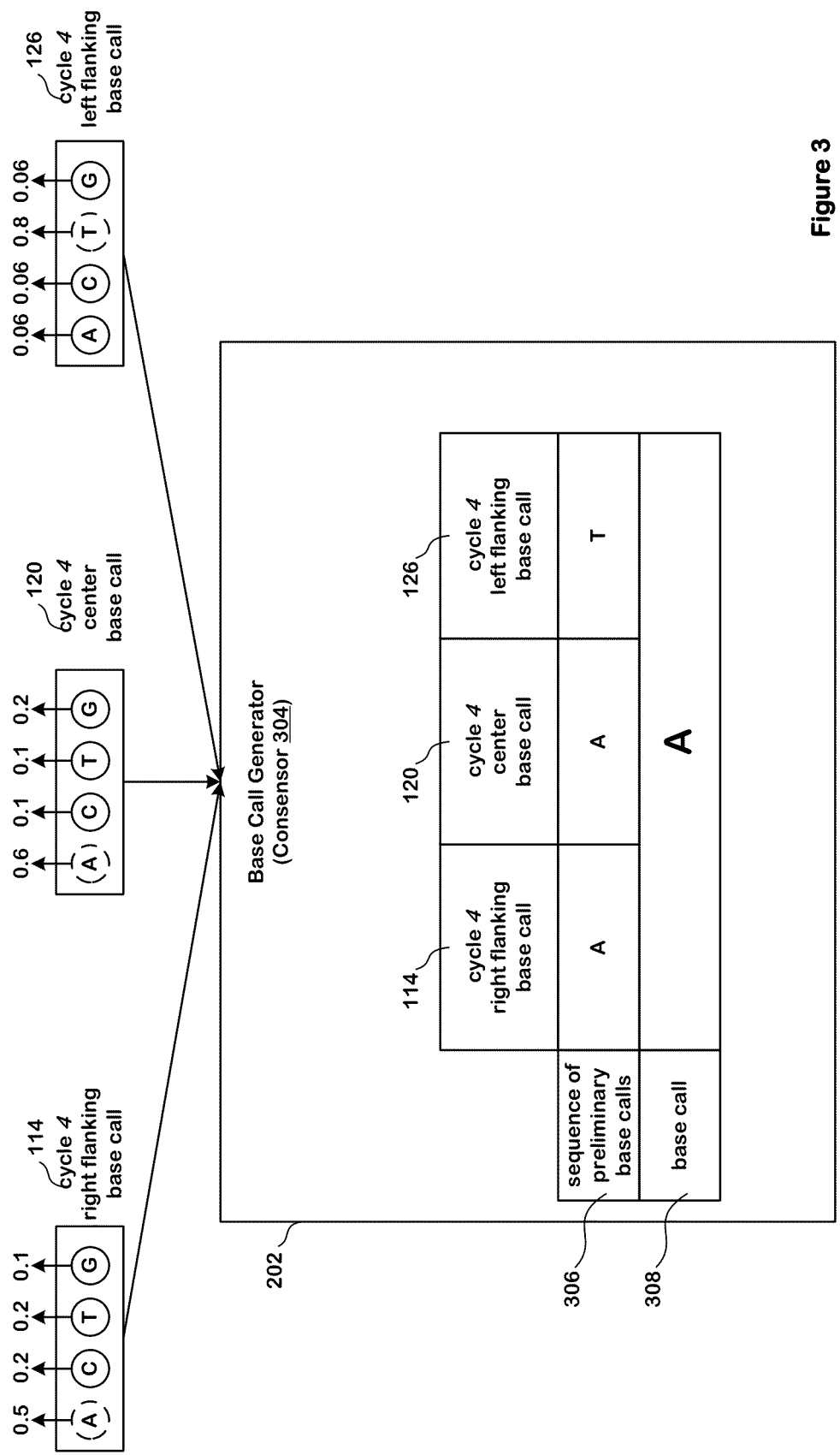
Figure 4:
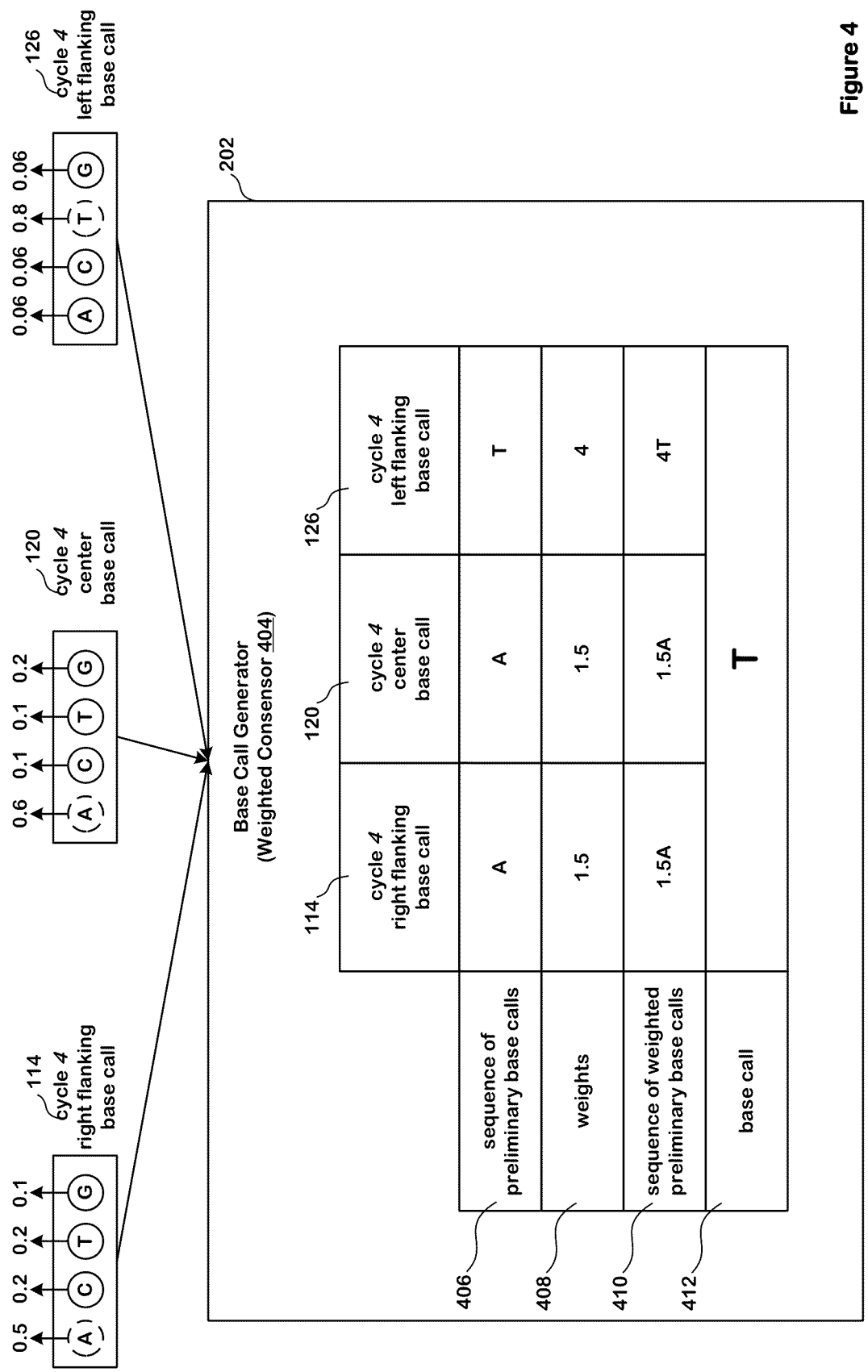

FIGS. 2, 3, and 4 show different implementations of a base call generator. The base call generator 202 (e.g., running on a host processor) is coupled (e.g., via a PCIe bus or Ethernet or InfiniBand (IB)) to the neural network-based base caller 102 (e.g., running on a chip) and is configured to generate a base call for the current sequencing cycle (e.g., cycle 4) based on the right flanking, center, and left flanking base call predictions for the current sequencing cycle.

The current image data for the current sequencing cycle depicts intensity emissions of analytes and their surrounding background captured at the current sequencing cycle. The right flanking 114, center 120, and left 126 flanking base call predictions for the current sequencing cycle (e.g., cycle 4) identify likelihoods of a base incorporated in one or more of the analytes at the current sequencing cycle being A, C, T, and G. In one implementation, the likelihoods are exponentially normalized scores produced by a softmax layer used as an output layer by the base caller 102.

In one implementation, the right flanking base call prediction 114 for the current sequencing cycle accounts for prephasing effect between the current sequencing cycle (e.g., cycle 4) and the previous sequencing cycles. In one implementation, the center base call prediction 120 for the current sequencing cycle (e.g., cycle 4) accounts for the prephasing effect between the current sequencing cycle and the previous sequencing cycles and phasing effect between the current sequencing cycle and the successive sequencing cycles. In one implementation, the left flanking base call prediction 126 for the current sequencing cycle (e.g., cycle 4) accounts for the phasing effect between the current sequencing cycle and the successive sequencing cycles.

As shown in FIG. 2, the base call generator is further configured to comprise an averager 204 that base-wise sums the likelihoods across the right flanking 114, center 120, and left 126 flanking base call predictions for the current sequencing cycle (e.g., cycle 4), determines base-wise averages 212 based on the base-wise sums, and generates the base call 214 for the current sequencing cycle (e.g., cycle 4) based on a highest one of the base-wise averages (e.g., 0.38).

As shown in FIG. 3, the base call generator is further configured to comprise a consensor 304 that determines a preliminary base call for each of the right flanking 114, center 120, and left flanking 126 base call predictions for the current sequencing cycle (e.g., cycle 4) based on a highest one of the likelihoods, thereby producing a sequence 306 of preliminary base calls, and generates the base call for the current sequencing cycle based on a most common base call 308 in the sequence of preliminary base calls.

As shown in FIG. 4, the base call generator is further configured to comprise a weighted consensor 404 that determines a preliminary base call for each of the right flanking, center, and left flanking base call predictions for the current sequencing cycle based on a highest one of the likelihoods, thereby producing a sequence 406 of preliminary base calls, applies base-wise weights 408 to respective ones of the preliminary base calls in the sequence of preliminary base calls and produces a sequence 410 of weighted preliminary base calls, and generates the base call for the current sequencing cycle (e.g., cycle 4) based on a most weighted base call 412 in the sequence of weighted preliminary base calls. In some implementations, the base-wise weights 408 are preset, for example, on a cycle-bycycle basis. In other implementations, the base-wise weights 408 are learned, for example, using a least-square approach.

Figure 6:
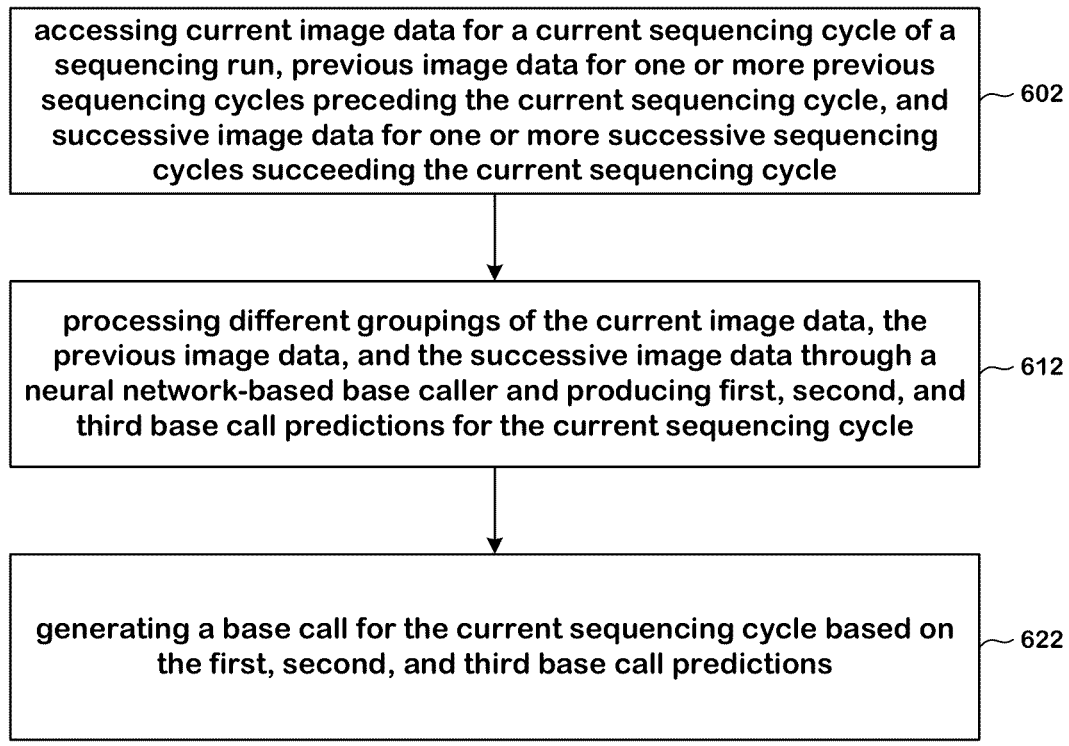
FIG. 6 is a flowchart of one implementation of the technology disclosed.

In one implementation illustrated in FIG. 6, the technology disclosed includes accessing current image data for a current sequencing cycle of a sequencing run (action 602), previous image data for one or more previous sequencing cycles preceding the current sequencing cycle, and successive image data for one or more successive sequencing cycles succeeding the current sequencing cycle, processing different groupings of the current image data, the previous image data, and the successive image data through a neural network-based base caller and producing first, second, and third base call predictions for the current sequencing cycle (action 612), and generating a base call for the current sequencing cycle based on the first, second, and third base call predictions (action 622).

In one implementation, the different groupings include a first grouping comprising the current image data and the previous image data, a second grouping comprising the current image data, the previous image data, and the successive image data, and a third grouping comprising the current image data and the successive image data.

In one implementation, the technology disclosed includes processing the first grouping through the neural network-based base caller to produce the first base call prediction, processing the second grouping through the neural network-based base caller to produce the second base call prediction, and processing the third grouping through the neural network-based base caller to produce the third base call prediction.

In one implementation, the first, second, and third base call predictions for the current sequencing cycle identify likelihoods of a base incorporated in one or more of the analytes at the current sequencing cycle being A, C, T, and G.

In one implementation, the technology disclosed includes generating the base call for the current sequencing cycle by base-wise summing the likelihoods across the first, second, and third base call predictions for the current sequencing cycle, determining base-wise averages based on the base-wise summing, and generating the base call for the current sequencing cycle based on a highest one of the base-wise averages.

In one implementation, the technology disclosed includes generating the base call for the current sequencing cycle by determining a preliminary base call for each of the first, second, and third base call predictions for the current sequencing cycle based on a highest one of the likelihoods, thereby producing a sequence of preliminary base calls, and generating the base call for the current sequencing cycle based on a most common base call in the sequence of preliminary base calls.

In one implementation, the technology disclosed includes generating the base call for the current sequencing cycle by determining a preliminary base call for each of the first, second, and third base call predictions for the current sequencing cycle based on a highest one of the likelihoods, thereby producing a sequence of preliminary base calls, applying base-wise weights to respective ones of the preliminary base calls in the sequence of preliminary base calls and producing a sequence of weighted preliminary base calls, and generating the base call for the current sequencing cycle based on a most weighted base call in the sequence of weighted preliminary base calls.

In one implementation called "multi-cycle training, single-cycle inference," the base caller 102 is trained to produce two or more base call predictions for two or more sequencing cycles during training using the base caller generator, but during inference produces base call prediction only for a single sequencing cycle.

In one implementation called "multi-cycle training, multi-cycle inference," the base caller 102 is trained to produce two or more base call predictions for two or more sequencing cycles during training and do the same during the inference using the base caller generator 202.

Multi-Cycle Gradient Backpropagation

Figure 5:
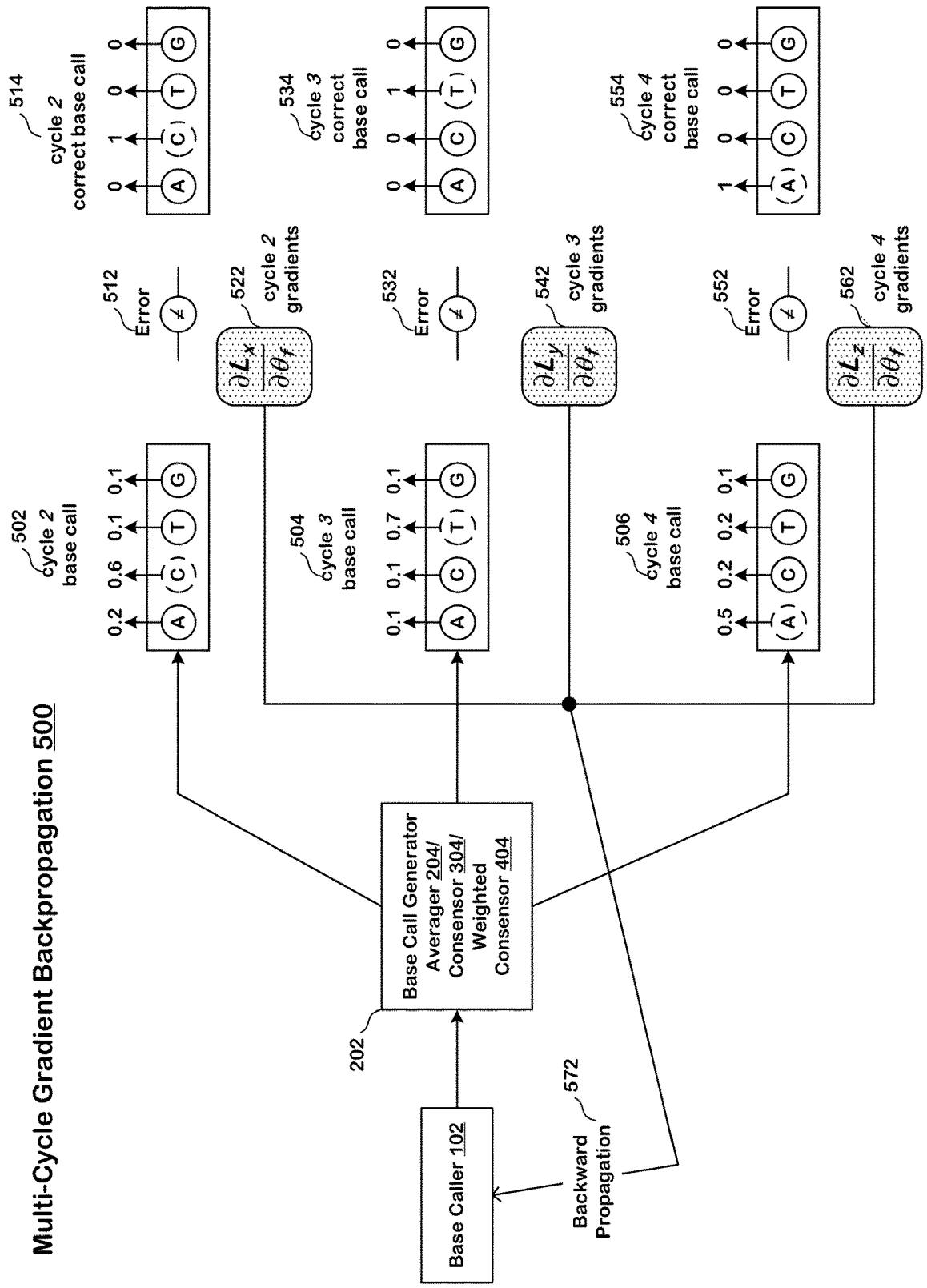
FIG. 5 shows one implementation of the disclosed multi-cycle gradient backpropagation.

FIG. 5 shows one implementation of the disclosed "multi-cycle gradient backpropagation 500." As shown in FIG. 5, the many-to-many base calling 100 is further configured to comprise a trainer that, computes errors 512, 532, and 552 between base calls generated by the base call generator 202 for the current sequencing cycle (e.g., cycle 3), the previous sequencing cycles (e.g., cycle 2), and the successive sequencing cycles (e.g., cycle 4) based on the right flanking 506, center 504, and left flanking 502 outputs of the neural network-based base caller 102 and respective ground truth base calls 554, 534, and 514, determines respective gradients 542, 522, and 562 for the current sequencing cycle, the previous sequencing cycles, and the successive sequencing cycles based on the errors, and updates parameters of the neural network-based base caller by backpropagating the gradients.

Technical Effect/Advantage

Figure 7:
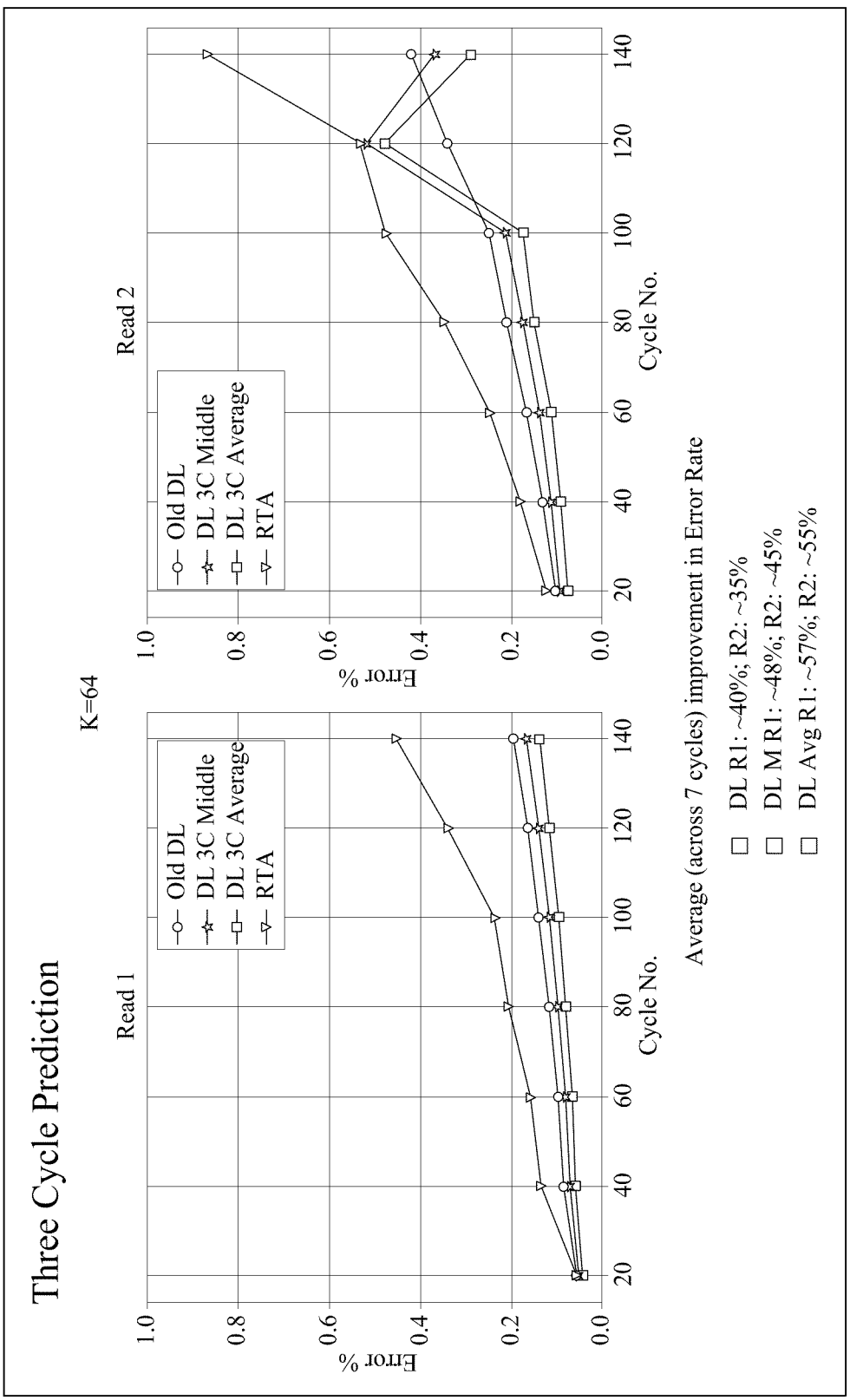
FIG. 7 illustrates technical effect and advantages of the technology disclosed.

FIG. 7 illustrates technical effect and advantages of the technology disclosed.

The "multi-cycle training, single-cycle inference" implementation is called "DL 3C Middle" in FIG. 7 and improves the base calling error rate by 8% over the traditional non-neural network-based real time analysis base calling software.

The "multi-cycle training, multi-cycle inference" implementation is called "DL 3C Average" in FIG. 7 and further improves the base calling error rate by another 8% over the DL 3C Middle implementation.

Base calling sequencing cycles multiple times improves the base calling accuracy and detects and resolves base calling discrepancies and ambiguous base calls.

The multi-cycle gradient backpropagation also improves the gradients of the base caller 102 and its base calling accuracy over the training task of base calling.

Sequencing System

Figure 8A:
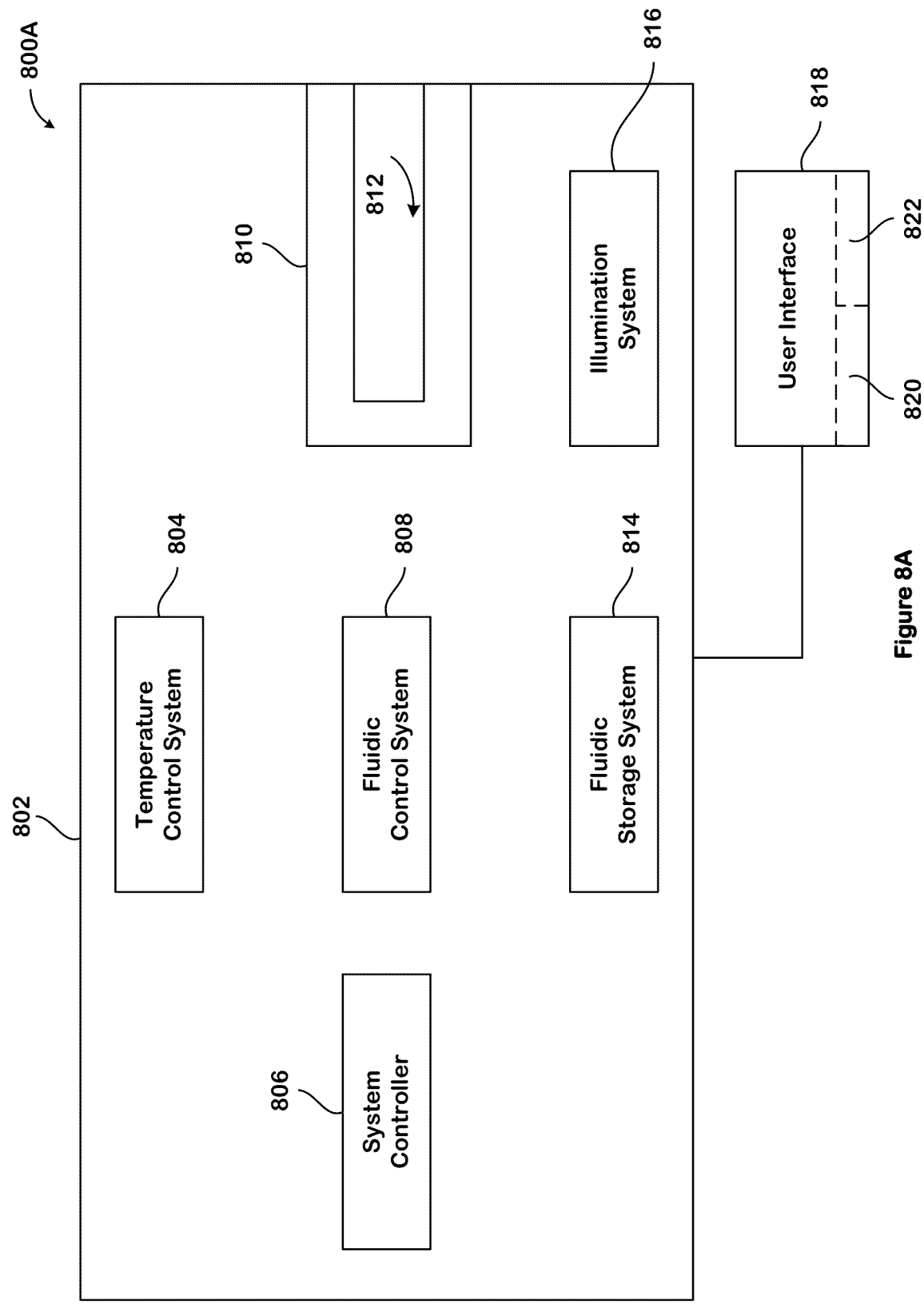
FIGS. 8A and 8B depict one implementation of a sequencing system. The sequencing system comprises a configurable processor.
Figure 8B:
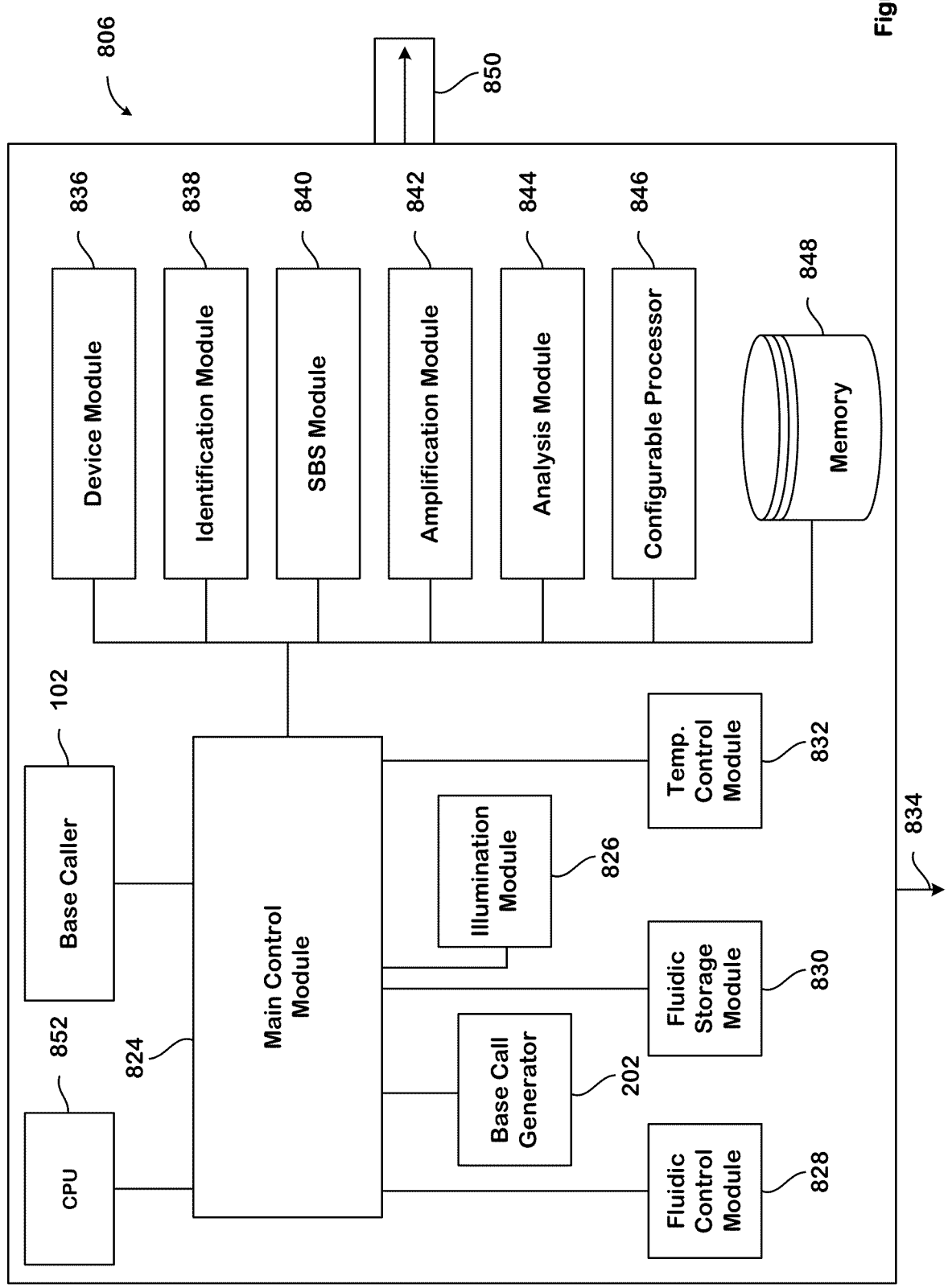

FIGS. 8A and 8B depict one implementation of a sequencing system 800A. The sequencing system 800A comprises a configurable processor 846. The configurable processor 846 implements the base calling techniques disclosed herein. The sequencing system is also referred to as a "sequencer."

The sequencing system 800A can operate to obtain any information or data that relates to at least one of a biological or chemical substance. In some implementations, the sequencing system 800A is a workstation that may be similar to a bench-top device or desktop computer. For example, a majority (or all) of the systems and components for conducting the desired reactions can be within a common housing 802.

In particular implementations, the sequencing system 800A is a nucleic acid sequencing system configured for various applications, including but not limited to de novo sequencing, resequencing of whole genomes or target genomic regions, and metagenomics. The sequencer may also be used for DNA or RNA analysis. In some implementations, the sequencing system 800A may also be configured to generate reaction sites in a biosensor. For example, the sequencing system 800A may be configured to receive a sample and generate surface attached clusters of clonally amplified nucleic acids derived from the sample. Each cluster may constitute or be part of a reaction site in the biosensor.

The exemplary sequencing system 800A may include a system receptacle or interface 810 that is configured to interact with a biosensor 812 to perform desired reactions within the biosensor 812. In the following description with respect to FIG. 8A, the biosensor 812 is loaded into the system receptacle 810. However, it is understood that a cartridge that includes the biosensor 812 may be inserted into the system receptacle 810 and in some states the cartridge can be removed temporarily or permanently. As described above, the cartridge may include, among other things, fluidic control and fluidic storage components.

In particular implementations, the sequencing system 800A is configured to perform a large number of parallel reactions within the biosensor 812. The biosensor 812 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 812 may include a solid-state imaging device (e.g., CCD or CMOS imager) and a flow cell mounted thereto. The flow cell may include one or more flow channels that receive a solution from the sequencing system 800A and direct the solution toward the reaction sites. Optionally, the biosensor 812 can be configured to engage a thermal element for transferring thermal energy into or out of the flow channel.

The sequencing system 800A may include various components, assemblies, and systems (or sub-systems) that interact with each other to perform a predetermined method or assay protocol for biological or chemical analysis. For example, the sequencing system 800A includes a system controller 806 that may communicate with the various components, assemblies, and sub-systems of the sequencing system 800A and also the biosensor 812. For example, in addition to the system receptacle 810, the sequencing system 800A may also include a fluidic control system 808 to control the flow of fluid throughout a fluid network of the sequencing system 800A and the biosensor 812; a fluid storage system 814 that is configured to hold all fluids (e.g., gas or liquids) that may be used by the bioassay system; a temperature control system 804 that may regulate the temperature of the fluid in the fluid network, the fluid storage system 814, and/or the biosensor 812; and an illumination system 816 that is configured to illuminate the biosensor 812. As described above, if a cartridge having the biosensor 812 is loaded into the system receptacle 810, the cartridge may also include fluidic control and fluidic storage components.

Also shown, the sequencing system 800A may include a user interface 818 that interacts with the user. For example, the user interface 818 may include a display 820 to display or request information from a user and a user input device 822 to receive user inputs. In some implementations, the display 820 and the user input device 822 are the same device. For example, the user interface 818 may include a touch-sensitive display configured to detect the presence of an individual's touch and also identify a location of the touch on the display. However, other user input devices 822 may be used, such as a mouse, touchpad, keyboard, keypad, handheld scanner, voice-recognition system, motion-recognition system, and the like. As will be discussed in greater detail below, the sequencing system 800A may communicate with various components, including the biosensor 812 (e.g., in the form of a cartridge), to perform the desired reactions. The sequencing system 800A may also be configured to analyze data obtained from the biosensor to provide a user with desired information.

The system controller 806 may include any processor-based or microprocessor-based system, including systems using microcontrollers, reduced instruction set computers (RISC), application specific integrated circuits (ASICs), field programmable gate array (FPGAs), coarse-grained reconfigurable architectures (CGRAs), logic circuits, and any other circuit or processor capable of executing functions described herein. The above examples are exemplary only, and are thus not intended to limit in any way the definition and/or meaning of the term system controller. In the exemplary implementation, the system controller 806 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the sequencing system 800A.

The set of instructions may include various commands that instruct the sequencing system 800A or biosensor 812 to perform specific operations such as the methods and processes of the various implementations described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the sequencing system 800A, processed in response to user inputs, or processed in response to a request made by another processing machine (e.g., a remote request through a communication link). In the illustrated implementation, the system controller 806 includes an analysis module 844. In other implementations, system controller 806 does not include the analysis module 844 and instead has access to the analysis module 844 (e.g., the analysis module 844 may be separately hosted on cloud).

The system controller 806 may be connected to the biosensor 812 and the other components of the sequencing system 800A via communication links. The system controller 806 may also be communicatively connected to off-site systems or servers. The communication links may be hard-wired, corded, or wireless. The system controller 806 may receive user inputs or commands, from the user interface 818 and the user input device 822.

The fluidic control system 808 includes a fluid network and is configured to direct and regulate the flow of one or more fluids through the fluid network. The fluid network may be in fluid communication with the biosensor 812 and the fluid storage system 814. For example, select fluids may be drawn from the fluid storage system 814 and directed to the biosensor 812 in a controlled manner, or the fluids may be drawn from the biosensor 812 and directed toward, for example, a waste reservoir in the fluid storage system 814. Although not shown, the fluidic control system 808 may include flow sensors that detect a flow rate or pressure of the fluids within the fluid network. The sensors may communicate with the system controller 806.

The temperature control system 804 is configured to regulate the temperature of fluids at different regions of the fluid network, the fluid storage system 814, and/or the biosensor 812. For example, the temperature control system 804 may include a thermocycler that interfaces with the biosensor 812 and controls the temperature of the fluid that flows along the reaction sites in the biosensor 812. The temperature control system 804 may also regulate the temperature of solid elements or components of the sequencing system 800A or the biosensor 812. Although not shown, the temperature control system 804 may include sensors to detect the temperature of the fluid or other components. The sensors may communicate with the system controller 806.

The fluid storage system 814 is in fluid communication with the biosensor 812 and may store various reaction components or reactants that are used to conduct the desired reactions therein. The fluid storage system 814 may also store fluids for washing or cleaning the fluid network and biosensor 812 and for diluting the reactants. For example, the fluid storage system 814 may include various reservoirs to store samples, reagents, enzymes, other biomolecules, buffer solutions, aqueous, and non-polar solutions, and the like. Furthermore, the fluid storage system 814 may also include waste reservoirs for receiving waste products from the biosensor 812. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 816 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 816 may be configured to direct an excitation light to reaction sites. As one example, fluorophores may be excited by green wavelengths of light, as such the wavelength of the excitation light may be approximately 532 nm. In one implementation, the illumination system 816 is configured to produce illumination that is parallel to a surface normal of a surface of the biosensor 812. In another implementation, the illumination system 816 is configured to produce illumination that is off-angle relative to the surface normal of the surface of the biosensor 812. In yet another implementation, the illumination system 816 is configured to produce illumination that has plural angles, including some parallel illumination and some off-angle illumination.

The system receptacle or interface 810 is configured to engage the biosensor 812 in at least one of a mechanical, electrical, and fluidic manner. The system receptacle 810 may hold the biosensor 812 in a desired orientation to facilitate the flow of fluid through the biosensor 812. The system receptacle 810 may also include electrical contacts that are configured to engage the biosensor 812 so that the sequencing system 800A may communicate with the biosensor 812 and/or provide power to the biosensor 812. Furthermore, the system receptacle 810 may include fluidic ports (e.g., nozzles) that are configured to engage the biosensor 812. In some implementations, the biosensor 812 is removably coupled to the system receptacle 810 in a mechanical manner, in an electrical manner, and also in a fluidic manner.

In addition, the sequencing system 800A may communicate remotely with other systems or networks or with other bioassay systems 800A. Detection data obtained by the bioassay system(s) 800A may be stored in a remote database.

FIG. 8B is a block diagram of a system controller 806 that can be used in the system of FIG. 8A. In one implementation, the system controller 806 includes one or more processors or modules that can communicate with one another. Each of the processors or modules may include an algorithm (e.g., instructions stored on a tangible and/or non-transitory computer readable storage medium) or sub-algorithms to perform particular processes. The system controller 806 is illustrated conceptually as a collection of modules, but may be implemented utilizing any combination of dedicated hardware boards, DSPs, processors, etc. Alternatively, the system controller 806 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 850 may transmit information (e.g., commands) to or receive information (e.g., data) from the biosensor 812 (FIG. 8A) and/or the sub-systems 808, 814, 804 (FIG. 8A). In implementations, the communication port 850 may output a plurality of sequences of pixel signals. A communication link 834 may receive user input from the user interface 818 (FIG. 8A) and transmit data or information to the user interface 818. Data from the biosensor 812 or sub-systems 808, 814, 804 may be processed by the system controller 806 in real-time during a bioassay session. Additionally or alternatively, data may be stored temporarily in a system memory during a bioassay session and processed in slower than real-time or off-line operation.

As shown in FIG. 8B, the system controller 806 may include a plurality of modules 824-848 that communicate with a main control module 824, along with a central processing unit (CPU) 852. The main control module 824 may communicate with the user interface 818 (FIG. 8A). Although the modules 824-848 are shown as communicating directly with the main control module 824, the modules 824-848 may also communicate directly with each other, the user interface 818, and the biosensor 812. Also, the modules 824-848 may communicate with the main control module 824 through the other modules.

The plurality of modules 824-848 include system modules 828-832, 826 that communicate with the sub-systems 808, 814, 804, and 816, respectively. The fluidic control module 828 may communicate with the fluidic control system 808 to control the valves and flow sensors of the fluid network for controlling the flow of one or more fluids through the fluid network. The fluid storage module 830 may notify the user when fluids are low or when the waste reservoir is at or near capacity. The fluid storage module 830 may also communicate with the temperature control module 832 so that the fluids may be stored at a desired temperature. The illumination module 826 may communicate with the illumination system 816 to illuminate the reaction sites at designated times during a protocol, such as after the desired reactions (e.g., binding events) have occurred. In some implementations, the illumination module 826 may communicate with the illumination system 816 to illuminate the reaction sites at designated angles.

The plurality of modules 824-848 may also include a device module 836 that communicates with the biosensor 812 and an identification module 838 that determines identification information relating to the biosensor 812. The device module 836 may, for example, communicate with the system receptacle 810 to confirm that the biosensor has established an electrical and fluidic connection with the sequencing system 800A. The identification module 838 may receive signals that identify the biosensor 812. The identification module 838 may use the identity of the biosensor 812 to provide other information to the user. For example, the identification module 838 may determine and then display a lot number, a date of manufacture, or a protocol that is recommended to be run with the biosensor 812.

The plurality of modules 824-848 also includes an analysis module 844 (also called signal processing module or signal processor) that receives and analyzes the signal data (e.g., image data) from the biosensor 812. Analysis module 844 includes memory (e.g., RAM or Flash) to store detection/image data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 818 to display desired information to the user. In some implementations, the signal data may be processed by the solid-state imager (e.g., CMOS image sensor) before the analysis module 844 receives the signal data.

The analysis module 844 is configured to obtain image data from the light detectors at each of a plurality of sequencing cycles. The image data is derived from the emission signals detected by the light detectors and process the image data for each of the plurality of sequencing cycles through the base caller 102 and produce a base call for at least some of the analytes at each of the plurality of sequencing cycle. The light detectors can be part of one or more over-head cameras (e.g., Illumina's GAIIx's CCD camera taking images of the clusters on the biosensor 812 from the top), or can be part of the biosensor 812 itself (e.g., Illumina's iSeq's CMOS image sensors underlying the clusters on the biosensor 812 and taking images of the clusters from the bottom).

The output of the light detectors is the sequencing images, each depicting intensity emissions of the clusters and their surrounding background. The sequencing images depict intensity emissions generated as a result of nucleotide incorporation in the sequences during the sequencing. The intensity emissions are from associated analytes and their surrounding background. The sequencing images are stored in memory 848.

Protocol modules 840 and 842 communicate with the main control module 824 to control the operation of the sub-systems 808, 814, and 804 when conducting predetermined assay protocols. The protocol modules 840 and 842 may include sets of instructions for instructing the sequencing system 800A to perform specific operations pursuant to predetermined protocols. As shown, the protocol module may be a sequencing-by-synthesis (SBS) module 840 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g., as catalyzed by a polymerase enzyme) or ligation (e.g., catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 816 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (2008); WO 04/018497; U.S. Pat. No. 7,057,026; WO 91/06678; WO 07/123744; U.S. Pat. Nos. 7,329,492; 7,211,414; 7,315,019; 7,405,281, and US 2008/014708082, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in U.S. Pat. App. Ser. Nos. 61/538,294 and 61/619,878, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 842 that is configured to issue commands to the fluidic control system 808 and the temperature control system 804 for amplifying a product within the biosensor 812. For example, the biosensor 812 may be engaged to the sequencing system 800A. The amplification module 842 may issue instructions to the fluidic control system 808 to deliver necessary amplification components to reaction chambers within the biosensor 812. In other implementations, the reaction sites may already contain some components for amplification, such as the template DNA and/or primers. After delivering the amplification components to the reaction chambers, the amplification module 842 may instruct the temperature control system 804 to cycle through different temperature stages according to known amplification protocols. In some implementations, the amplification and/or nucleotide incorporation is performed isothermally.

The SBS module 840 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 840 may instruct the fluidic control system 808 to direct a flow of reagent and enzyme solutions through the biosensor 812. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/02814714709 A1, PCT Publication No. WO 05/065814, US Patent Application Publication No. 2005/014700900 A1, PCT Publication No. WO 06/08B199 and PCT Publication No. WO 07/01470251, each of which is incorporated herein by reference in its entirety. Exemplary reagents for reversible terminator-based SBS are described in U.S. Pat. Nos. 7,541,444; 7,057,026; 7,414,14716; 7,427,673; 7,566,537; 7,592,435 and WO 07/14835368, each of which is incorporated herein by reference in its entirety.

In some implementations, the amplification and SBS modules may operate in a single assay protocol where, for example, template nucleic acid is amplified and subsequently sequenced within the same cartridge.

The sequencing system 800A may also allow the user to reconfigure an assay protocol. For example, the sequencing system 800A may offer options to the user through the user interface 818 for modifying the determined protocol. For example, if it is determined that the biosensor 812 is to be used for amplification, the sequencing system 800A may request a temperature for the annealing cycle. Furthermore, the sequencing system 800A may issue warnings to a user if a user has provided user inputs that are generally not acceptable for the selected assay protocol.

In implementations, the biosensor 812 includes millions of sensors (or pixels), each of which generates a plurality of sequences of pixel signals over successive base calling cycles. The analysis module 844 detects the plurality of sequences of pixel signals and attributes them to corresponding sensors (or pixels) in accordance to the row-wise and/or column-wise location of the sensors on an array of sensors.

Figure 9:
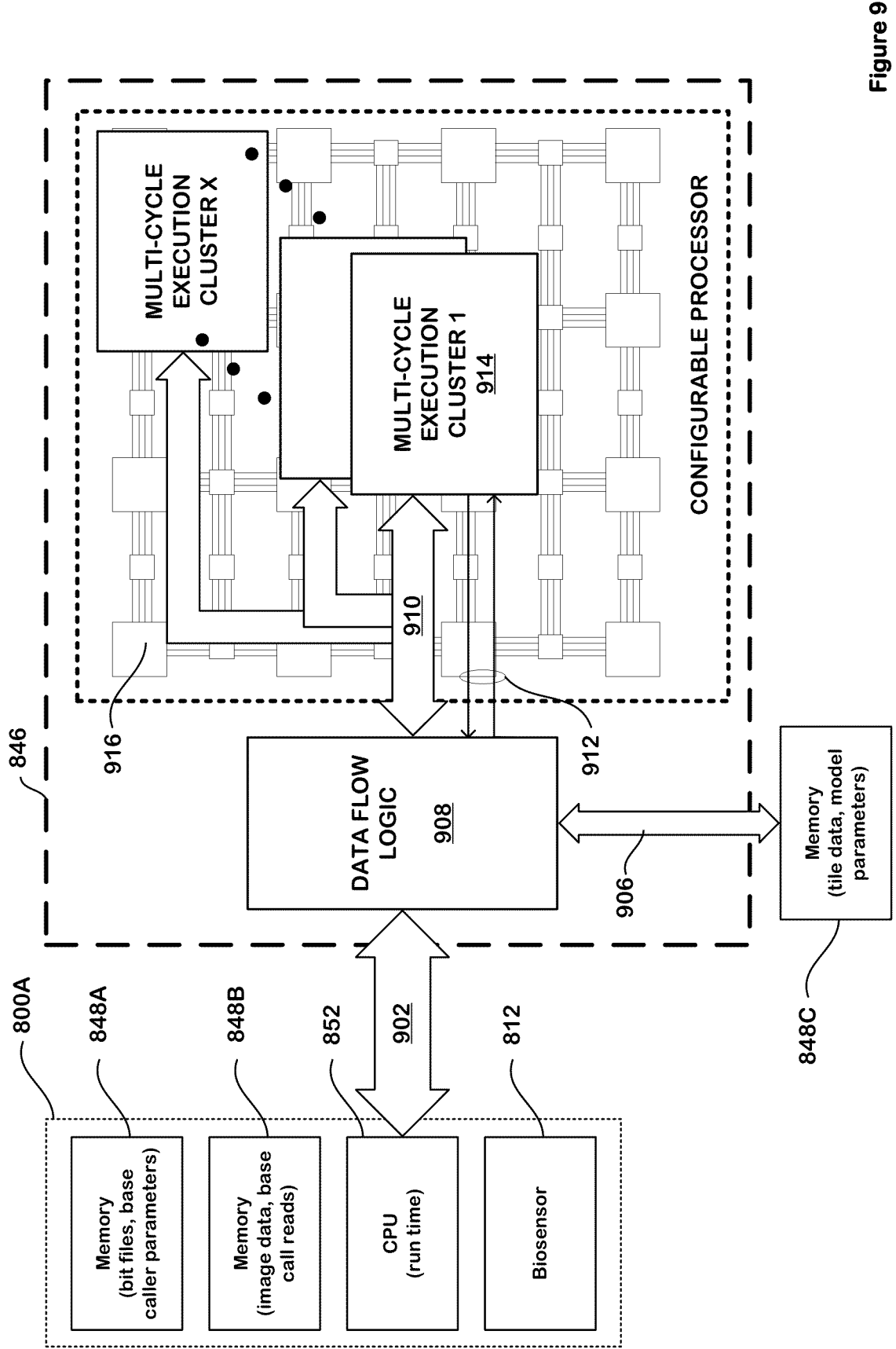
FIG. 9 is a simplified block diagram of a system for analysis of sensor data from the sequencing system, such as base call sensor outputs.

FIG. 9 is a simplified block diagram of a system for analysis of sensor data from the sequencing system 800A, such as base call sensor outputs. In the example of FIG. 9, the system includes the configurable processor 846. The configurable processor 846 can execute a base caller (e.g., the neural network-based base caller 102) in coordination with a runtime program executed by the central processing unit (CPU) 852 (i.e., a host processor). The sequencing system 800A comprises the biosensor 812 and flow cells. The flow cells can comprise one or more tiles in which clusters of genetic material are exposed to a sequence of analyte flows used to cause reactions in the clusters to identify the bases in the genetic material. The sensors sense the reactions for each cycle of the sequence in each tile of the flow cell to provide tile data. Genetic sequencing is a data intensive operation, which translates base call sensor data into sequences of base calls for each cluster of genetic material sensed in during a base call operation.

The system in this example includes the CPU 852, which executes a runtime program to coordinate the base call operations, memory 848B to store sequences of arrays of tile data, base call reads produced by the base calling operation, and other information used in the base call operations. Also, in this illustration the system includes memory 848A to store a configuration file (or files), such as FPGA bit files, and model parameters for the neural networks used to configure and reconfigure the configurable processor 846, and execute the neural networks. The sequencing system 800A can include a program for configuring a configurable processor and in some embodiments a reconfigurable processor to execute the neural networks.

The sequencing system 800A is coupled by a bus 902 to the configurable processor 846. The bus 902 can be implemented using a high throughput technology, such as in one example bus technology compatible with the PCIe standards (Peripheral Component Interconnect Express) currently maintained and developed by the PCI-SIG (PCI Special Interest Group). Also in this example, a memory 848A is coupled to the configurable processor 846 by bus 906. The memory 848A can be on-board memory, disposed on a circuit board with the configurable processor 846. The memory 848A is used for high speed access by the configurable processor 846 of working data used in the base call operation. The bus 906 can also be implemented using a high throughput technology, such as bus technology compatible with the PCIe standards.

Configurable processors, including field programmable gate arrays FPGAs, coarse grained reconfigurable arrays CGRAs, and other configurable and reconfigurable devices, can be configured to implement a variety of functions more efficiently or faster than might be achieved using a general purpose processor executing a computer program. Configuration of configurable processors involves compiling a functional description to produce a configuration file, referred to sometimes as a bitstream or bit file, and distributing the configuration file to the configurable elements on the processor. The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include Google's Tensor Processing Unit (TPU)™, rackmount solutions like GX4 Rackmount Series™, GX9 Rackmount Series™, NVIDIA DGX-1™, Microsoft' Stratix V FPGA™, Graphcore's Intelligent Processor Unit (IPU)™, Qualcomm's Zeroth Platform™0 with Snapdragon Processors™ NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, Xilinx Alveo™ U200, Xilinx Alveo™ U250, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Embodiments described herein implement the neural network-based base caller 102 using the configurable processor 846. The configuration file for the configurable processor 846 can be implemented by specifying the logic functions to be executed using a high level description language HDL or a register transfer level RTL language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor configurable processor 846, in all embodiments described herein, therefore include a configured processor comprising an application specific ASIC or special purpose integrated circuit or set of integrated circuits, or a system-on-a-chip SOC device, or a graphics processing unit (GPU) processor or a coarse-grained reconfigurable architecture (CGRA) processor, configured to execute a neural network based base call operation as described herein.

In general, configurable processors and configured processors described herein, as configured to execute runs of a neural network, are referred to herein as neural network processors.

The configurable processor 846 is configured in this example by a configuration file loaded using a program executed by the CPU 852, or by other sources, which configures the array of configurable elements 916 (e.g., configuration logic blocks (CLB) such as look up tables (LUTs), flip-flops, compute processing units (PMUs), and compute memory units (CMUs), configurable I/O blocks, programmable interconnects), on the configurable processor to execute the base call function. In this example, the configuration includes data flow logic 908 which is coupled to the buses 902 and 906 and executes functions for distributing data and control parameters among the elements used in the base call operation.

Also, the configurable processor 846 is configured with base call execution data flow logic 908 to execute the neural network-based base caller 102. The data flow logic 908 comprises multi-cycle execution clusters (e.g., 914) which, in this example, includes execution cluster 1 through execution cluster X. The number of multi-cycle execution clusters can be selected according to a trade-off involving the desired throughput of the operation, and the available resources on the configurable processor 846.

The multi-cycle execution clusters are coupled to the data flow logic 908 by data flow paths 910 implemented using configurable interconnect and memory resources on the configurable processor 846. Also, the multi-cycle execution clusters are coupled to the data flow logic 908 by control paths 912 implemented using configurable interconnect and memory resources for example on the configurable processor 846, which provide control signals indicating available execution clusters, readiness to provide input units for execution of a run of the neural network-based base caller 102 to the available execution clusters, readiness to provide trained parameters for the neural network-based base caller 102, readiness to provide output patches of base call classification data, and other control data used for execution of the neural network-based base caller 102.

The configurable processor 846 is configured to execute runs of the neural network-based base caller 102 using trained parameters to produce classification data for the sensing cycles of the base calling operation. A run of the neural network-based base caller 102 is executed to produce classification data for a subject sensing cycle of the base calling operation. A run of the neural network-based base caller 102 operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic 908 is configured to move tile data and at least some trained parameters of the model parameters from the memory 848A to the configurable processor 846 for runs of the neural network-based base caller 102, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in embodiments of the base calling operation, the tile data can comprise information about alignment of the images with the clusters such as distance from center information indicating the distance of each pixel in the array of sensor data from the center of a cluster of genetic material on the tile.

During execution of the neural network-based base caller 102 as described below, tile data can also include data produced during execution of the neural network-based base caller 102, referred to as intermediate data, which can be reused rather than recomputed during a run of the neural network-based base caller 102. For example, during execution of the neural network-based base caller 102, the data flow logic 908 can write intermediate data to the memory 848A in place of the sensor data for a given patch of an array of tile data. Embodiments like this are described in more detail below.

As illustrated, a system is described for analysis of base call sensor output, comprising memory (e.g., 848A) accessible by the runtime program storing tile data including sensor data for a tile from sensing cycles of a base calling operation. Also, the system includes a neural network processor, such as configurable processor 846 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 908 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution clusters in the plurality of execution clusters configured to execute a neural network. The data flow logic 908 has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

Figure 10:
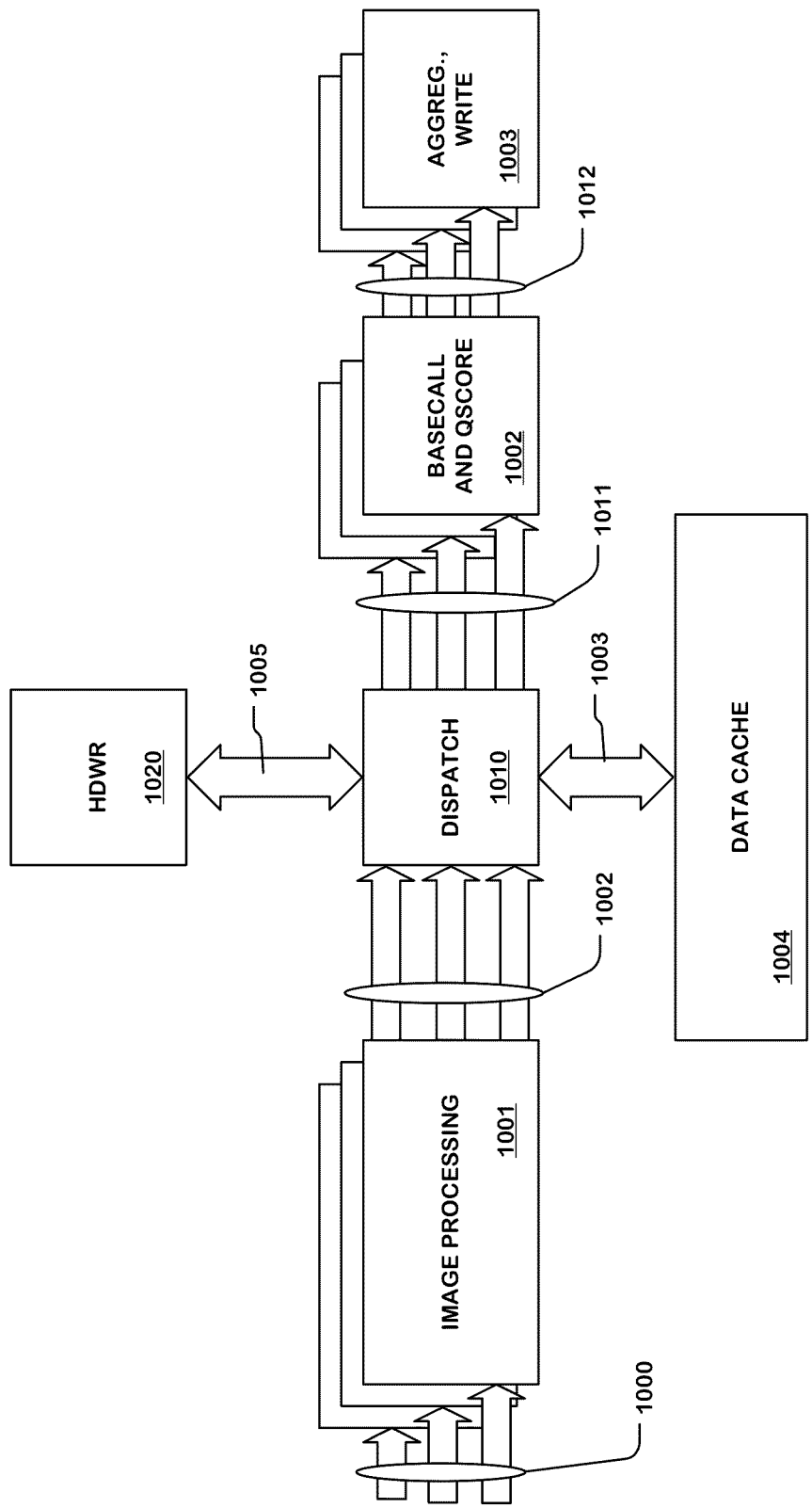
FIG. 10 is a simplified diagram showing aspects of the base calling operation, including functions of a runtime program executed by a host processor.

As shown in FIGS. 9 and 10, in one implementation, the technology disclosed comprises an artificial intelligence-based system for base calling. The system comprises a host processor, memory accessible by the host processor storing image data for sequencing cycles of a sequencing run, wherein current image data for a current sequencing cycle of the sequencing run depicts intensity emissions of analytes and their surrounding background captured at the current sequencing cycle, and a configurable processor having access to the memory, the configurable processor including a plurality of execution clusters, the execution clusters in the plurality of execution clusters configured to execute a neural network, and data flow logic having access to the memory and to the execution clusters in the plurality of execution clusters, configured to provide the current image data, previous image data for one or more previous sequencing cycles preceding the current sequencing cycle, and successive image data for one or more successive sequencing cycles succeeding the current sequencing cycle to available execution clusters in the plurality of execution clusters, cause the execution clusters to apply different groupings of the current image data, the previous image data, and the successive image data to the neural network to produce first, second, and third base call predictions for the current sequencing cycle, and to feedback the first, second, and third base call predictions for the current sequencing cycle to the memory for use in generation of a base call for the current sequencing cycle based on the first, second, and third base call predictions.

In one implementation, the different groupings include a first grouping comprising the current image data and the previous image data, a second grouping comprising the current image data, the previous image data, and the successive image data, and a third grouping comprising the current image data and the successive image data.

In one implementation, the execution clusters apply the first grouping to the neural network to produce the first base call prediction, the second grouping to the neural network to produce the second base call prediction, and the third grouping to the neural network to produce the third base call prediction.

In one implementation, the first, second, and third base call predictions for the current sequencing cycle identify likelihoods of a base incorporated in one or more of the analytes at the current sequencing cycle being A, C, T, and G.

In one implementation, the data flow logic is further configured to generate the base call for the current sequencing cycle by base-wise summing the likelihoods across the first, second, and third base call predictions for the current sequencing cycle, determining base-wise averages based on the base-wise summing, and generating the base call for the current sequencing cycle based on a highest one of the base-wise averages.

In one implementation, the data flow logic is further configured to generate the base call for the current sequencing cycle by determining a preliminary base call for each of the first, second, and third base call predictions for the current sequencing cycle based on a highest one of the likelihoods, thereby producing a sequence of preliminary base calls, and generating the base call for the current sequencing cycle based on a most common base call in the sequence of preliminary base calls.

In one implementation, the data flow logic is further configured to generate the base call for the current sequencing cycle by determining a preliminary base call for each of the first, second, and third base call predictions for the current sequencing cycle based on a highest one of the likelihoods, thereby producing a sequence of preliminary base calls, applying base-wise weights to respective ones of the preliminary base calls in the sequence of preliminary base calls and producing a sequence of weighted preliminary base calls, and generating the base call for the current sequencing cycle based on a most weighted base call in the sequence of weighted preliminary base calls.

FIG. 10 is a simplified diagram showing aspects of the base calling operation, including functions of a runtime program executed by a host processor. In this diagram, the output of image sensors from a flow cell are provided on lines 1000 to image processing threads 1001, which can perform processes on images such as alignment and arrangement in an array of sensor data for the individual tiles and resampling of images, and can be used by processes which calculate a tile cluster mask for each tile in the flow cell, which identifies pixels in the array of sensor data that correspond to clusters of genetic material on the corresponding tile of the flow cell. The outputs of the image processing threads 1001 are provided on lines 1002 to a dispatch logic 1010 in the CPU which routes the arrays of tile data to a data cache 1004 (e.g., SSD storage) on a high-speed bus 1003, or on high-speed bus 1005 to the neural network processor hardware 1020, such as the configurable processor 846 of FIG. 9, according to the state of the base calling operation. The processed and transformed images can be stored on the data cache 1004 for sensing cycles that were previously used. The hardware 1020 returns classification data output by the neural network to the dispatch logic 1010, which passes the information to the data cache 1004, or on lines 1011 to threads 1002 that perform base call and quality score computations using the classification data, and can arrange the data in standard formats for base call reads. The outputs of the threads 1002 that perform base calling and quality score computations are provided on lines 1012 to threads 1003 that aggregate the base call reads, perform other operations such as data compression, and write the resulting base call outputs to specified destinations for utilization by the customers.

In some embodiments, the host can include threads (not shown) that perform final processing of the output of the hardware 1020 in support of the neural network. For example, the hardware 1020 can provide outputs of classification data from a final layer of the multi-cluster neural network. The host processor can execute an output activation function, such as a softmax function, over the classification data to configure the data for use by the base call and quality score threads 1002. Also, the host processor can execute input operations (not shown), such as batch normalization of the tile data prior to input to the hardware 1020.

Figure 11:
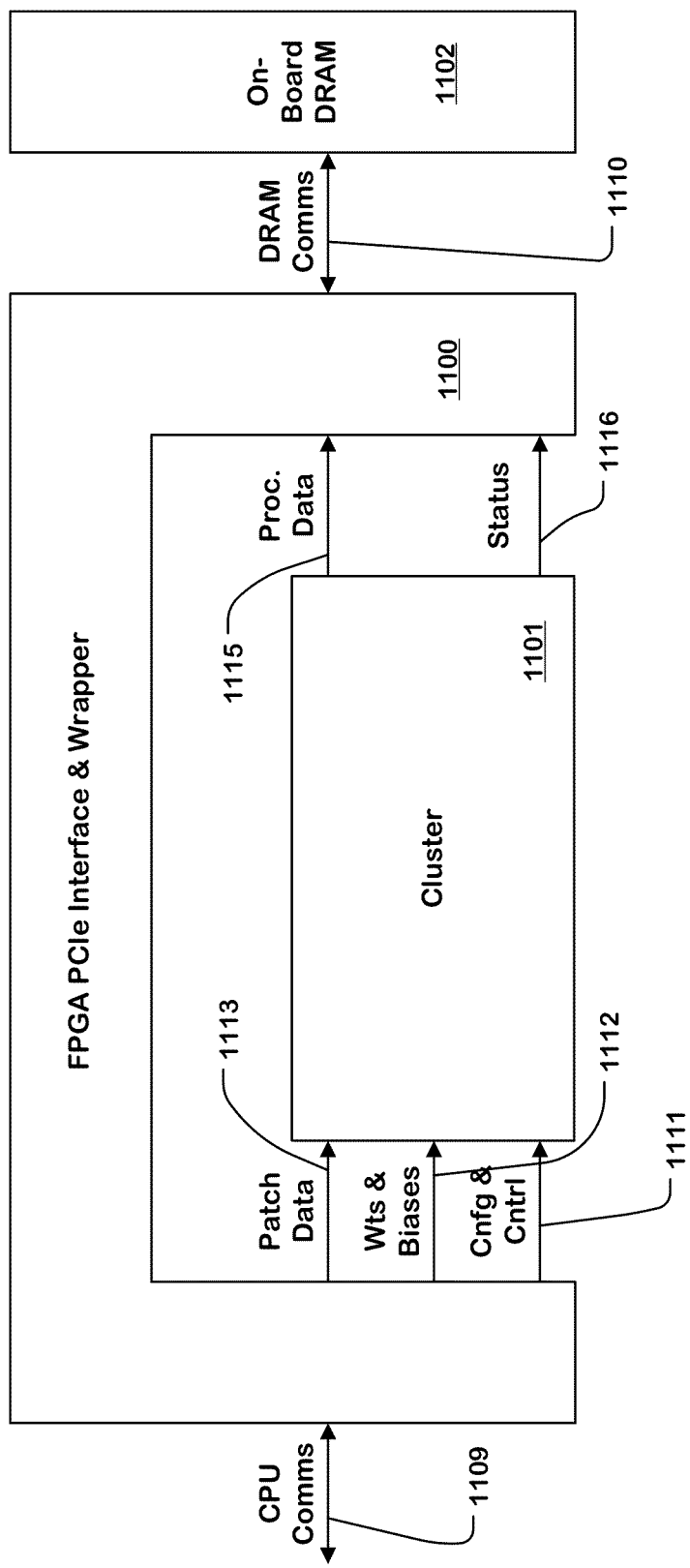
FIG. 11 is a simplified diagram of a configuration of a configurable processor such as that of FIG. 9.

FIG. 11 is a simplified diagram of a configuration of a configurable processor 846 such as that of FIG. 9. In FIG. 11, the configurable processor 846 comprises an FPGA with a plurality of high speed PCIe interfaces. The FPGA is configured with a wrapper 1100 which comprises the data flow logic 908 described with reference to FIG. 9. The wrapper 1100 manages the interface and coordination with a runtime program in the CPU across the CPU communication link 1109 and manages communication with the on-board DRAM 1102 (e.g., memory 848A) via DRAM communication link 1110. The data flow logic 908 in the wrapper 1100 provides patch data retrieved by traversing the arrays of tile data on the on-board DRAM 1102 for the number N cycles to a cluster 1101, and retrieves process data 1115 from the cluster 1101 for delivery back to the on-board DRAM 1102. The wrapper 1100 also manages transfer of data between the on-board DRAM 1102 and host memory, for both the input arrays of tile data, and for the output patches of classification data. The wrapper transfers patch data on line 1113 to the allocated cluster 1101. The wrapper provides trained parameters, such as weights and biases on line 1112 to the cluster 1101 retrieved from the on-board DRAM 1102. The wrapper provides configuration and control data on line 1111 to the cluster 1101 provided from, or generated in response to, the runtime program on the host via the CPU communication link 1109. The cluster can also provide status signals on line 1116 to the wrapper 1100, which are used in cooperation with control signals from the host to manage traversal of the arrays of tile data to provide spatially aligned patch data, and to execute the multi-cycle neural network over the patch data using the resources of the cluster 1101.

As mentioned above, there can be multiple clusters on a single configurable processor managed by the wrapper 1100 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some embodiments. For example, the model trained parameters may be updated once every 20 cycles (or other number of cycles), or according to update patterns implemented for particular systems and neural network models. In some embodiments including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 1100. The wrapper 1100 can optionally do some pre-processing and transformation of the sensing data and write the information to the on-board DRAM 1102. The input tile data for each sensing cycle can include arrays of sensor data including on the order of 4000×3000 pixels per sensing cycle per tile or more, with two features representing colors of two images of the tile, and one or two bytes per feature per pixel. For an embodiment in which the number N is three sensing cycles to be used in each run of the multi-cycle neural network, the array of tile data for each run of the multi-cycle neural network can consume on the order of hundreds of megabytes per tile. In some embodiments of the system, the tile data also includes an array of DFC data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various embodiments.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 1102. When the processing of the entire tile has been completed, and the output patches of data transferred to the DRAM, the wrapper sends the processed output array for the tile back to the host/CPU in a specified format. In some embodiments, the on-board DRAM 1102 is managed by memory management logic in the wrapper 1100. The runtime program can control the sequencing operations to complete analysis of all the arrays of tile data for all the cycles in the run in a continuous flow to provide real time analysis.

Computer System

Figure 12:
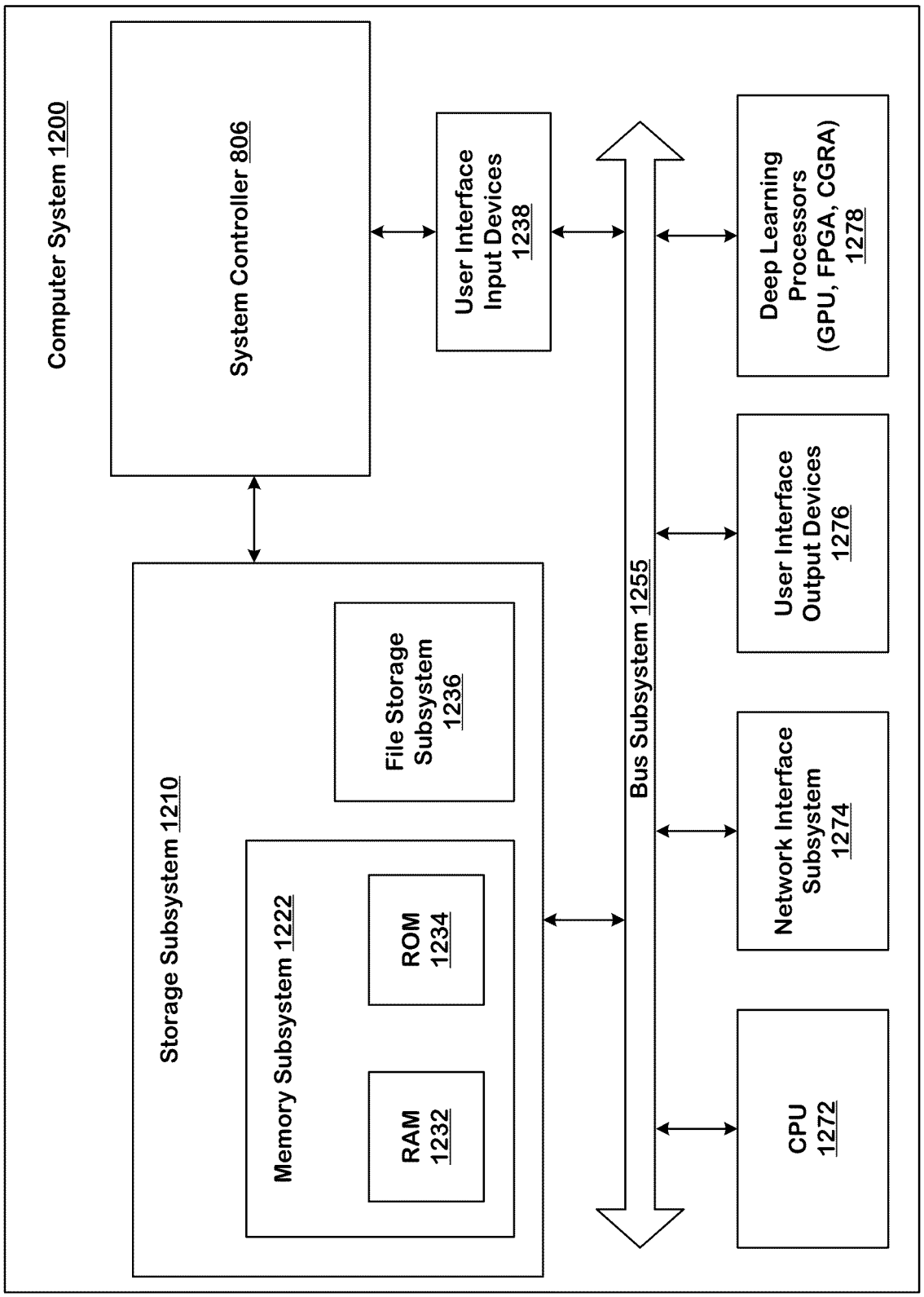
FIG. 12 is a computer system that can be used by the disclosed sequencing system to implement the base calling techniques disclosed herein.

FIG. 12 is a computer system 1200 that can be used by the sequencing system 800A to implement the base calling techniques disclosed herein. Computer system 1200 includes at least one central processing unit (CPU) 1272 that communicates with a number of peripheral devices via bus subsystem 1255. These peripheral devices can include a storage subsystem 1210 including, for example, memory devices and a file storage subsystem 1236, user interface input devices 1238, user interface output devices 1276, and a network interface subsystem 1274. The input and output devices allow user interaction with computer system 1200. Network interface subsystem 1274 provides an interface to outside networks, including an interface to corresponding interface devices in other computer systems.

In one implementation, the system controller 806 is communicably linked to the storage subsystem 1210 and the user interface input devices 1238.

User interface input devices 1238 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1200.

User interface output devices 1276 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1200 to the user or to another machine or computer system.

Storage subsystem 1210 stores programming and data constructs that provide the functionality of some or all of the modules and methods described herein. These software modules are generally executed by deep learning processors 1278.

Deep learning processors 1278 can be graphics processing units (GPUs), field-programmable gate arrays (FPGAs), application-specific integrated circuits (ASICs), and/or coarse-grained reconfigurable architectures (CGRAs). Deep learning processors 1278 can be hosted by a deep learning cloud platform such as Google Cloud Platform™, Xilinx™, and Cirrascale™ Examples of deep learning processors 1278 include Google's Tensor Processing Unit (TPU)™, rackmount solutions like GX4 Rackmount Series™, GX12 Rackmount Series™, NVIDIA DGX-1™ Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 1222 used in the storage subsystem 1210 can include a number of memories including a main random access memory (RAM) 1232 for storage of instructions and data during program execution and a read only memory (ROM) 1234 in which fixed instructions are stored. A file storage subsystem 1236 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1236 in the storage subsystem 1210, or in other machines accessible by the processor.

Bus subsystem 1255 provides a mechanism for letting the various components and subsystems of computer system 1200 communicate with each other as intended. Although bus subsystem 1255 is shown schematically as a single bus, alternative implementations of the bus subsystem can use multiple busses.

Computer system 1200 itself can be of varying types including a personal computer, a portable computer, a workstation, a computer terminal, a network computer, a television, a mainframe, a server farm, a widely-distributed set of loosely networked computers, or any other data processing system or user device. Due to the ever changing nature of computers and networks, the description of computer system 1200 depicted in FIG. 12 is intended only as a specific example for purposes of illustrating the preferred implementations of the present invention. Many other configurations of computer system 1200 are possible having more or less components than the computer system depicted in FIG. 12.

Clauses

We disclose the following clauses:
1. An artificial intelligence-based system for base calling, the system comprising:
a neural network-based base caller that processes at least right flanking, center, and left flanking inputs, and produces at least right flanking, center, and left flanking outputs;

wherein the right flanking input comprises current image data for a current sequencing cycle of a sequencing run, supplemented with previous image data for one or more previous sequencing cycles preceding the current sequencing cycle, and wherein the right flanking output comprises a right flanking base call prediction for the current sequencing cycle and base call predictions for the previous sequencing cycles;

wherein the center input comprises the current image data, supplemented with the previous image data and successive image data for one or more successive sequencing cycles succeeding the current sequencing cycle, and wherein the center output comprises a center base call prediction for the current sequencing cycle and base call predictions for the previous sequencing cycles and the successive sequencing cycles;

wherein the left flanking input comprises the current image data, supplemented with the successive image data, and wherein the left flanking output comprises a left flanking base call prediction for the current sequencing cycle and base call predictions for the successive sequencing cycles; and a base call generator coupled to the neural network-based base caller and configured to generate a base call for the current sequencing cycle based on the right flanking, center, and left flanking base call predictions for the current sequencing cycle.

2. The artificial intelligence-based system of clause 1, wherein the current image data for the current sequencing cycle depicts intensity emissions of analytes and their surrounding background captured at the current sequencing cycle.

3. The artificial intelligence-based system of clause 2, wherein the right flanking, center, and left flanking base call predictions for the current sequencing cycle identify likelihoods of a base incorporated in one or more of the analytes at the current sequencing cycle being A, C, T, and G.

4. The artificial intelligence-based system of clause 3, wherein the base call generator is further configured to comprise an averager that base-wise sums the likelihoods across the right flanking, center, and left flanking base call predictions for the current sequencing cycle;

determines base-wise averages based on the base-wise sums; and generates the base call for the current sequencing cycle based on a highest one of the base-wise averages.

5. The artificial intelligence-based system of clause 3, wherein the base call generator is further configured to comprise a consensor that determines a preliminary base call for each of the right flanking, center, and left flanking base call predictions for the current sequencing cycle based on a highest one of the likelihoods, thereby producing a sequence of preliminary base calls; and generates the base call for the current sequencing cycle based on a most common base call in the sequence of preliminary base calls.

6. The artificial intelligence-based system of clause 3, wherein the base call generator is further configured to comprise a weighted consensor that determines a preliminary base call for each of the right flanking, center, and left flanking base call predictions for the current sequencing cycle based on a highest one of the likelihoods, thereby producing a sequence of preliminary base calls;

applies base-wise weights to respective ones of the preliminary base calls in the sequence of preliminary base calls and produces a sequence of weighted preliminary base calls; and generates the base call for the current sequencing cycle based on a most weighted base call in the sequence of weighted preliminary base calls.

7. The artificial intelligence-based system of clause 3, wherein the likelihoods are exponentially normalized scores produced by a softmax layer.

8. The artificial intelligence-based system of clause 1, further configured to comprise a trainer that, during training, computes errors between base calls generated by the base call generator for the current sequencing cycle, the previous sequencing cycles, and the successive sequencing cycles based on the right flanking, center, and left flanking outputs of the neural network-based base caller and ground truth base calls;

determines gradients for the current sequencing cycle, the previous sequencing cycles, and the successive sequencing cycles based on the errors; and updates parameters of the neural network-based base caller by backpropagating the gradients.

9. The artificial intelligence-based system of clause 1, wherein the right flanking base call prediction for the current sequencing cycle accounts for prephasing effect between the current sequencing cycle and the previous sequencing cycles.

10. The artificial intelligence-based system of clause 9, wherein the center base call prediction for the current sequencing cycle accounts for the prephasing effect between the current sequencing cycle and the previous sequencing cycles and phasing effect between the current sequencing cycle and the successive sequencing cycles.

11. The artificial intelligence-based system of clause 10, wherein the left flanking base call prediction for the current sequencing cycle accounts for the phasing effect between the current sequencing cycle and the successive sequencing cycles.

12. An artificial intelligence-based system for base calling, the system comprising:

a host processor;

memory accessible by the host processor storing image data for sequencing cycles of a sequencing run, wherein current image data for a current sequencing cycle of the sequencing run depicts intensity emissions of analytes and their surrounding background captured at the current sequencing cycle; and a configurable processor having access to the memory, the configurable processor including:

a plurality of execution clusters, the execution clusters in the plurality of execution clusters configured to execute a neural network; and data flow logic having access to the memory and to the execution clusters in the plurality of execution clusters, configured to provide the current image data, previous image data for one or more previous sequencing cycles preceding the current sequencing cycle, and successive image data for one or more successive sequencing cycles succeeding the current sequencing cycle to available execution clusters in the plurality of execution clusters, cause the execution clusters to apply different groupings of the current image data, the previous image data, and the successive image data to the neural network to produce first, second, and third base call predictions for the current sequencing cycle, and to feedback the first, second, and third base call predictions for the current sequencing cycle to the memory for use in generation of a base call for the current sequencing cycle based on the first, second, and third base call predictions.

13. The artificial intelligence-based system of clause 12, wherein the different groupings include a first grouping comprising the current image data and the previous image data, a second grouping comprising the current image data, the previous image data, and the successive image data, and a third grouping comprising the current image data and the successive image data.

14. The artificial intelligence-based system of clause 13, wherein the execution clusters apply the first grouping to the neural network to produce the first base call prediction, the second grouping to the neural network to produce the second base call prediction, and the third grouping to the neural network to produce the third base call prediction.

15. The artificial intelligence-based system of clause 12, wherein the first, second, and third base call predictions for the current sequencing cycle identify likelihoods of a base incorporated in one or more of the analytes at the current sequencing cycle being A, C, T, and G.

16. The artificial intelligence-based system of clause 15, wherein the data flow logic is further configured to generate the base call for the current sequencing cycle by
base-wise summing the likelihoods across the first, second, and third base call predictions for the current sequencing cycle;
determining base-wise averages based on the base-wise summing; and
generating the base call for the current sequencing cycle based on a highest one of the base-wise averages.

17. The artificial intelligence-based system of clause 15, wherein the data flow logic is further configured to generate the base call for the current sequencing cycle by
determining a preliminary base call for each of the first, second, and third base call predictions for the current sequencing cycle based on a highest one of the likelihoods, thereby producing a sequence of preliminary base calls; and
generating the base call for the current sequencing cycle based on a most common base call in the sequence of preliminary base calls.

18. The artificial intelligence-based system of clause 15, wherein the data flow logic is further configured to generate the base call for the current sequencing cycle by
determining a preliminary base call for each of the first, second, and third base call predictions for the current sequencing cycle based on a highest one of the likelihoods, thereby producing a sequence of preliminary base calls;
applying base-wise weights to respective ones of the preliminary base calls in the sequence of preliminary base calls and producing a sequence of weighted preliminary base calls; and
generating the base call for the current sequencing cycle based on a most weighted base call in the sequence of weighted preliminary base calls.

19. An artificial intelligence-based method of base calling, the method including:
accessing current image data for a current sequencing cycle of a sequencing run, previous image data for one or more previous sequencing cycles preceding the current sequencing cycle, and successive image data for one or more successive sequencing cycles succeeding the current sequencing cycle;
processing different groupings of the current image data, the previous image data, and the successive image data through a neural network-based base caller and producing first, second, and third base call predictions for the current sequencing cycle; and
generating a base call for the current sequencing cycle based on the first, second, and third base call predictions.

20. The artificial intelligence-based method of clause 19, wherein the different groupings include
a first grouping comprising the current image data and the previous image data,
a second grouping comprising the current image data, the previous image data, and the successive image data, and
a third grouping comprising the current image data and the successive image data.

21. The artificial intelligence-based method of clause 20, further including:
processing the first grouping through the neural network-based base caller to produce the first base call prediction,
processing the second grouping through the neural network-based base caller to produce the second base call prediction, and
processing the third grouping through the neural network-based base caller to produce the third base call prediction.

22. The artificial intelligence-based method of clause 19, wherein the first, second, and third base call predictions for the current sequencing cycle identify likelihoods of a base incorporated in one or more of the analytes at the current sequencing cycle being A, C, T, and G.

23. The artificial intelligence-based method of clause 22, further including generating the base call for the current sequencing cycle by
base-wise summing the likelihoods across the first, second, and third base call predictions for the current sequencing cycle;
determining base-wise averages based on the base-wise summing; and
generating the base call for the current sequencing cycle based on a highest one of the base-wise averages.

24. The artificial intelligence-based method of clause 22, further including generating the base call for the current sequencing cycle by
determining a preliminary base call for each of the first, second, and third base call predictions for the current sequencing cycle based on a highest one of the likelihoods, thereby producing a sequence of preliminary base calls; and
generating the base call for the current sequencing cycle based on a most common base call in the sequence of preliminary base calls.

25. The artificial intelligence-based method of clause 22, further including generating the base call for the current sequencing cycle by
determining a preliminary base call for each of the first, second, and third base call predictions for the current sequencing cycle based on a highest one of the likelihoods, thereby producing a sequence of preliminary base calls;

applying base-wise weights to respective ones of the preliminary base calls in the sequence of preliminary base calls and producing a sequence of weighted preliminary base calls; and generating the base call for the current sequencing cycle based on a most weighted base call in the sequence of weighted preliminary base calls.

26. An artificial intelligence-based method of base calling, the method including:

processing at least right flanking, center, and left flanking inputs through a neural network-based base caller, and producing at least right flanking, center, and left flanking outputs;

wherein the right flanking input comprises current image data for a current sequencing cycle of a sequencing run, supplemented with previous image data for one or more previous sequencing cycles preceding the current sequencing cycle, and wherein the right flanking output comprises a right flanking base call prediction for the current sequencing cycle and base call predictions for the previous sequencing cycles;

wherein the center input comprises the current image data, supplemented with the previous image data and successive image data for one or more successive sequencing cycles succeeding the current sequencing cycle, and wherein the center output comprises a center base call prediction for the current sequencing cycle and base call predictions for the previous sequencing cycles and the successive sequencing cycles;

wherein the left flanking input comprises the current image data, supplemented with the successive image data, and wherein the left flanking output comprises a left flanking base call prediction for the current sequencing cycle and base call predictions for the successive sequencing cycles; and generating a base call for the current sequencing cycle based on the right flanking, center, and left flanking base call predictions for the current sequencing cycle.

27. The artificial intelligence-based method of clause 26, wherein the current image data for the current sequencing cycle depicts intensity emissions of analytes and their surrounding background captured at the current sequencing cycle.

28. The artificial intelligence-based method of clause 26, wherein the right flanking, center, and left flanking base call predictions for the current sequencing cycle identify likelihoods of a base incorporated in one or more of the analytes at the current sequencing cycle being A, C, T, and G.

29. The artificial intelligence-based method of clause 28, further including generating the base call for the current sequencing cycle by base-wise summing the likelihoods across the right flanking, center, and left flanking base call predictions for the current sequencing cycle;

determining base-wise averages based on the base-wise summing; and generating the base call for the current sequencing cycle based on a highest one of the base-wise averages.

30. The artificial intelligence-based method of clause 28, further including generating the base call for the current sequencing cycle by determining a preliminary base call for each of the right flanking, center, and left flanking base call predictions for the current sequencing cycle based on a highest one of the likelihoods, thereby producing a sequence of preliminary base calls; and generating the base call for the current sequencing cycle based on a most common base call in the sequence of preliminary base calls.

31. The artificial intelligence-based method of clause 28, further including generating the base call for the current sequencing cycle by determining a preliminary base call for each of the right flanking, center, and left flanking base call predictions for the current sequencing cycle based on a highest one of the likelihoods, thereby producing a sequence of preliminary base calls;

applying base-wise weights to respective ones of the preliminary base calls in the sequence of preliminary base calls and producing a sequence of weighted preliminary base calls; and generating the base call for the current sequencing cycle based on a most weighted base call in the sequence of weighted preliminary base calls.

32. The artificial intelligence-based method of clause 28, wherein the likelihoods are exponentially normalized scores produced by a softmax layer.

33. The artificial intelligence-based method of clause 26, further including, during training, computing errors between base calls generated by the base call generator for the current sequencing cycle, the previous sequencing cycles, and the successive sequencing cycles based on the right flanking, center, and left flanking outputs of the neural network-based base caller and ground truth base calls;

determining gradients for the current sequencing cycle, the previous sequencing cycles, and the successive sequencing cycles based on the errors; and updating parameters of the neural network-based base caller by backpropagating the gradients.

34. The artificial intelligence-based method of clause 26, wherein the right flanking base call prediction for the current sequencing cycle accounts for prephasing effect between the current sequencing cycle and the previous sequencing cycles.

35. The artificial intelligence-based method of clause 34, wherein the center base call prediction for the current sequencing cycle accounts for the prephasing effect between the current sequencing cycle and the previous sequencing cycles and phasing effect between the current sequencing cycle and the successive sequencing cycles.

36. The artificial intelligence-based method of clause 35, wherein the left flanking base call prediction for the current sequencing cycle accounts for the phasing effect between the current sequencing cycle and the successive sequencing cycles.

37. An artificial intelligence-based method of base calling, the method including:

processing at least first, second, and third inputs through a neural network-based base caller, and producing at least first, second, and third outputs;

wherein the first input comprises particular image data for a particular sequencing cycle of a sequencing run, supplemented with previous image data for one or more previous sequencing cycles preceding the particular sequencing cycle, and wherein the first output comprises a first base call prediction for the particular sequencing cycle and base call predictions for the previous sequencing cycles;

wherein the second input comprises the particular image data, supplemented with the previous image data and successive image data for one or more successive sequencing cycles succeeding the particular sequencing cycle, and wherein the second output comprises a second base call prediction for the particular sequencing cycle and base call predictions for the previous sequencing cycles and the successive sequencing cycles;

wherein the third input comprises the particular image data, supplemented with the successive image data, and wherein the third output comprises a third base call prediction for the particular sequencing cycle and base call predictions for the successive sequencing cycles; and generating a base call for the particular sequencing cycle based on the first, second, and third base call predictions for the particular sequencing cycle.

38. The artificial intelligence-based method of clause 37, implementing each of the clauses which ultimately depend from clause 1.

39. A non-transitory computer readable storage medium impressed with computer program instructions to perform artificial intelligence-based base calling, the instructions, when executed on a processor, implement a method comprising:

accessing current image data for a current sequencing cycle of a sequencing run, previous image data for one or more previous sequencing cycles preceding the current sequencing cycle, and successive image data for one or more successive sequencing cycles succeeding the current sequencing cycle;

processing different groupings of the current image data, the previous image data, and the successive image data through a neural network-based base caller and producing first, second, and third base call predictions for the current sequencing cycle; and generating a base call for the current sequencing cycle based on the first, second, and third base call predictions.

40. The non-transitory computer readable storage medium of clause 39, implementing each of the clauses which ultimately depend from clause 1.

41. A non-transitory computer readable storage medium impressed with computer program instructions to perform artificial intelligence-based base calling, the instructions, when executed on a processor, implement a method comprising:

processing at least first, second, and left inputs through a neural network-based base caller, and producing at least first, second, and left outputs;

wherein the first input comprises particular image data for a particular sequencing cycle of a sequencing run, supplemented with previous image data for one or more previous sequencing cycles preceding the particular sequencing cycle, and wherein the first output comprises a first base call prediction for the particular sequencing cycle and base call predictions for the previous sequencing cycles;

wherein the second input comprises the particular image data, supplemented with the previous image data and successive image data for one or more successive sequencing cycles succeeding the particular sequencing cycle, and wherein the second output comprises a second base call prediction for the particular sequencing cycle and base call predictions for the previous sequencing cycles and the successive sequencing cycles;

wherein the left input comprises the particular image data, supplemented with the successive image data, and wherein the left output comprises a left base call prediction for the particular sequencing cycle and base call predictions for the successive sequencing cycles; and generating a base call for the particular sequencing cycle based on the first, second, and left base call predictions for the particular sequencing cycle.

44. The non-transitory computer readable storage medium of clause 43, implementing each of the clauses which ultimately depend from clause 1.

45. An artificial intelligence-based method of base calling, the method including:

accessing a progression of per-cycle analyte channel sets generated for sequencing cycles of a sequencing run;

processing, through a neural network-based base caller, windows of per-cycle analyte channel sets in the progression for the windows of sequencing cycles of the sequencing run such that the neural network-based base caller processes a subject window of per-cycle analyte channel sets in the progression for the subject window of sequencing cycles of the sequencing run and generates provisional base call predictions for three or more sequencing cycles in the subject window of sequencing cycles;

from multiple windows in which a particular sequencing cycle appeared at different positions, using the neural network-based base caller to generate provisional base call predictions for the particular sequencing cycle; and determining a base call for the particular sequencing cycle based on the plurality of base call predictions.

46. The artificial intelligence-based method of clause 45, implementing each of the clauses which ultimately depend from clause 1.

47. A system including one or more processors coupled to memory, the memory loaded with computer instructions to perform artificial intelligence-based base calling, the instructions, when executed on the processors, implement actions comprising:

accessing a progression of per-cycle analyte channel sets generated for sequencing cycles of a sequencing run;

processing, through a neural network-based base caller, windows of per-cycle analyte channel sets in the progression for the windows of sequencing cycles of the sequencing run such that the neural network-based base caller processes a subject window of per-cycle analyte channel sets in the progression for the subject window of sequencing cycles of the sequencing run and generates provisional base call predictions for three or more sequencing cycles in the subject window of sequencing cycles;

from multiple windows in which a particular sequencing cycle appeared at different positions, using the neural network-based base caller to generate provisional base call predictions for the particular sequencing cycle; and determining a base call for the particular sequencing cycle based on the plurality of base call predictions.

48. The system of clause 47, implementing each of the clauses which ultimately depend from clause 1.

49. A non-transitory computer readable storage medium impressed with computer program instructions to perform artificial intelligence-based base calling, the instructions, when executed on a processor, implement a method comprising:

accessing a progression of per-cycle analyte channel sets generated for sequencing cycles of a sequencing run;

processing, through a neural network-based base caller, windows of per-cycle analyte channel sets in the progression for the windows of sequencing cycles of the sequencing run such that the neural network-based base caller processes a subject window of per-cycle analyte channel sets in the progression for the subject window of sequencing cycles of the sequencing run and generates provisional base call predictions for three or more sequencing cycles in the subject window of sequencing cycles;

from multiple windows in which a particular sequencing cycle appeared at different positions, using the neural network-based base caller to generate provisional base call predictions for the particular sequencing cycle; and determining a base call for the particular sequencing cycle based on the plurality of base call predictions.

50. The non-transitory computer readable storage medium of clause 49, implementing each of the clauses which ultimately depend from clause 1.

51. An artificial intelligence-based method of base calling, the method including:

accessing a series of per-cycle analyte channel sets generated for sequencing cycles of a sequencing run;

processing, through a neural network-based base caller, windows of per-cycle analyte channel sets in the series for the windows of sequencing cycles of the sequencing run such that the neural network-based base caller processes a subject window of per-cycle analyte channel sets in the series for the subject window of sequencing cycles of the sequencing run and generates base call predictions for two or more sequencing cycles in the subject window of sequencing cycles;

processing, through the neural network-based base caller, a plurality of the windows of per-cycle analyte channel sets in the series for the plurality of the windows of sequencing cycles of the sequencing run and generating an output for each window in the plurality of the windows, wherein each window in the plurality of the windows includes a particular per-cycle analyte channel set for a particular sequencing cycle of the sequencing run, and wherein the output for each window in the plurality of the windows includes (i) a base call prediction for the particular sequencing cycle and (ii) one or more additional base call predictions for one or more additional sequencing cycles of the sequencing run, thereby generating a plurality of base call predictions for the particular sequencing cycle across the plurality of the windows; and determining a base call for the particular sequencing cycle based on the plurality of base call predictions.

52. A system including one or more processors coupled to memory, the memory loaded with computer instructions to perform artificial intelligence-based base calling, the instructions, when executed on the processors, implement actions comprising:

accessing a series of per-cycle analyte channel sets generated for sequencing cycles of a sequencing run;

processing, through a neural network-based base caller, windows of per-cycle analyte channel sets in the series for the windows of sequencing cycles of the sequencing run such that the neural network-based base caller processes a subject window of per-cycle analyte channel sets in the series for the subject window of sequencing cycles of the sequencing run and generates base call predictions for two or more sequencing cycles in the subject window of sequencing cycles;

processing, through the neural network-based base caller, a plurality of the windows of per-cycle analyte channel sets in the series for the plurality of the windows of sequencing cycles of the sequencing run and generating an output for each window in the plurality of the windows, wherein each window in the plurality of the windows includes a particular per-cycle analyte channel set for a particular sequencing cycle of the sequencing run, and wherein the output for each window in the plurality of the windows includes (i) a base call prediction for the particular sequencing cycle and (ii) one or more additional base call predictions for one or more additional sequencing cycles of the sequencing run, thereby generating a plurality of base call predictions for the particular sequencing cycle across the plurality of the windows; and determining a base call for the particular sequencing cycle based on the plurality of base call predictions.

53. The system of clause 52, implementing each of the clauses which ultimately depend from clause 1.

54. A non-transitory computer readable storage medium impressed with computer program instructions to perform artificial intelligence-based base calling, the instructions, when executed on a processor, implement a method comprising:

accessing a series of per-cycle analyte channel sets generated for sequencing cycles of a sequencing run;

processing, through a neural network-based base caller, windows of per-cycle analyte channel sets in the series for the windows of sequencing cycles of the sequencing run such that the neural network-based base caller processes a subject window of per-cycle analyte channel sets in the series for the subject window of sequencing cycles of the sequencing run and generates base call predictions for two or more sequencing cycles in the subject window of sequencing cycles;

processing, through the neural network-based base caller, a plurality of the windows of per-cycle analyte channel sets in the series for the plurality of the windows of sequencing cycles of the sequencing run and generating an output for each window in the plurality of the windows, wherein each window in the plurality of the windows includes a particular per-cycle analyte channel set for a particular sequencing cycle of the sequencing run, and wherein the output for each window in the plurality of the windows includes (i) a base call prediction for the particular sequencing cycle and (ii) one or more additional base call predictions for one or more additional sequencing cycles of the sequencing run, thereby generating a plurality of base call predictions for the particular sequencing cycle across the plurality of the windows; and determining a base call for the particular sequencing cycle based on the plurality of base call predictions.

55. The non-transitory computer readable storage medium of clause 54, implementing each of the clauses which ultimately depend from clause 1.

Other implementations of the method described above can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

What is claimed is:

1. A system comprising:
   at least one processor; and
   a non-transitory computer readable medium comprising instructions that, when executed by the at least one processor, cause the system to:
   access a series of per-cycle analyte data sets generated for sequencing cycles of a sequencing run;
   process, through a base caller and from the series of per-cycle analyte data sets, an initial subject window of per-cycle analyte data sets corresponding to an initial subject window of sequencing cycles of the sequencing run;
   generate, utilizing the base caller, provisional base call predictions for a set of sequencing cycles in the initial subject window of sequencing cycles in which a target sequencing cycle appears at a target position; and
   determine a base call for the target sequencing cycle based on particular provisional base call predictions for the target sequencing cycle from the provisional base call predictions.

2. The system of claim 1, further comprising instructions that, when executed by the at least one processor, cause the system to:
   access the series of per-cycle analyte data sets for one or more image channels at the sequencing cycles of the sequencing run; and
   process, through the base caller, the initial subject window of per-cycle analyte data sets for the one or more image channels.

3. The system of claim 1, further comprising instructions that, when executed by the at least one processor, cause the system to:
   process, through the base caller and from the series of per-cycle analyte data sets, a subsequent subject window of per-cycle analyte data sets corresponding to a subsequent subject window of sequencing cycles of the sequencing run that does not include a sequencing cycle overlapping with the initial subject window of sequencing cycles;
   generate, utilizing the base caller, subsequent provisional base call predictions for a subsequent set of sequencing cycles in the subsequent subject window of sequencing cycles in which a subsequent target sequencing cycle appears at the target position; and
   determine a base call for the subsequent target sequencing cycle based on particular provisional base call predictions for the subsequent target sequencing cycle from the subsequent provisional base call predictions.

4. The system of claim 1, further comprising instructions that, when executed by the at least one processor, cause the system to:
   process, through the base caller and from the series of per-cycle analyte data sets, a previous subject window of per-cycle analyte data sets corresponding to a previous subject window of sequencing cycles of the sequencing run that does not include a sequencing cycle overlapping with the initial subject window of sequencing cycles;
   generate, utilizing the base caller, previous provisional base call predictions for a previous set of sequencing cycles in the previous subject window of sequencing cycles in which a previous target sequencing cycle appears at the target position; and
   determine a base call for the previous target sequencing cycle based on particular provisional base call predictions for the previous target sequencing cycle from the previous provisional base call predictions.

5. The system of claim 1, wherein:
   the target position comprises a center position within the initial subject window of sequencing cycles; and
   the initial subject window of sequencing cycles comprises flanking positioned adjacent to the center position.

6. The system of claim 1, wherein the set of sequencing cycles in the initial subject window of sequencing cycles comprises three or more sequencing cycles.

7. The system of claim 1, further comprising instructions that, when executed by the at least one processor, cause the system to access the series of per-cycle analyte data sets by accessing per-cycle images of intensity emission from clusters of nucleotide sequences.

8. The system of claim 1, wherein the base caller comprises a neural network-based base caller.

9. The system of claim 8, further comprising instructions that, when executed by the at least one processor, cause the system to generate the provisional base call predictions for the set of sequencing cycles in the initial subject window of sequencing cycles by:
   applying spatial convolution layers of the neural network-based base caller to the series of per-cycle analyte data sets to generate a spatially convolved representation of the series of per-cycle analyte data set;
   applying temporal convolution layers of the neural network-based base caller to combine the spatially convolved representation of the series of per-cycle analyte data set; and
   applying an output layer of the neural network-based base caller to the combined and convolved representation of the series of per-cycle analyte data set to generate, for the target sequencing cycle, probabilities of individual nucleotide bases.

10. A non-transitory computer readable storage medium storing instructions that, when executed by at least one processor, cause a computing system to:
    access a series of per-cycle analyte data sets generated for sequencing cycles of a sequencing run;
    process, through a base caller and from the series of per-cycle analyte data sets, an initial subject window of per-cycle analyte data sets corresponding to an initial subject window of sequencing cycles of the sequencing run;
    generate, utilizing the base caller, provisional base call predictions for a set of sequencing cycles in the initial subject window of sequencing cycles in which a target sequencing cycle appears at a target position; and determine a base call for the target sequencing cycle based on particular provisional base call predictions for the target sequencing cycle from the provisional base call predictions.

11. The non-transitory computer readable storage medium of claim 10, further storing instructions that, when executed by the at least one processor, cause the computing system to:
access the series of per-cycle analyte data sets for one or more image channels at the sequencing cycles of the sequencing run; and
process, through the base caller, the initial subject window of per-cycle analyte data sets for the one or more image channels.

12. The non-transitory computer readable storage medium of claim 10, further storing instructions that, when executed by the at least one processor, cause the computing system to:
process, through the base caller and from the series of per-cycle analyte data sets, a subsequent subject window of per-cycle analyte data sets corresponding to a subsequent subject window of sequencing cycles of the sequencing run that does not include a sequencing cycle overlapping with the initial subject window of sequencing cycles;
generate, utilizing the base caller, subsequent provisional base call predictions for a subsequent set of sequencing cycles in the subsequent subject window of sequencing cycles in which a subsequent target sequencing cycle appears at the target position; and
determine a base call for the subsequent target sequencing cycle based on particular provisional base call predictions for the subsequent target sequencing cycle from the subsequent provisional base call predictions.

13. The non-transitory computer readable storage medium of claim 10, further storing instructions that, when executed by the at least one processor, cause the computing system to:
process, through the base caller and from the series of per-cycle analyte data sets, a previous subject window of per-cycle analyte data sets corresponding to a previous subject window of sequencing cycles of the sequencing run that does not include a sequencing cycle overlapping with the initial subject window of sequencing cycles;
generate, utilizing the base caller, previous provisional base call predictions for a previous set of sequencing cycles in the previous subject window of sequencing cycles in which a previous target sequencing cycle appears at the target position; and
determine a base call for the previous target sequencing cycle based on particular provisional base call predictions for the previous target sequencing cycle from the previous provisional base call predictions.

14. The non-transitory computer readable storage medium of claim 10, wherein:
the target position comprises a center position within the initial subject window of sequencing cycles; and
the initial subject window of sequencing cycles comprises flanking positioned adjacent to the center position.

15. The non-transitory computer readable storage medium of claim 10, wherein the set of sequencing cycles in the initial subject window of sequencing cycles comprises three or more sequencing cycles.

16. The non-transitory computer readable storage medium of claim 15, further storing instructions that, when executed by the at least one processor, cause the computing system to access the series of per-cycle analyte data sets by accessing per-cycle images of intensity emission from clusters of nucleotide sequences.

17. A computer-implemented method comprising:
accessing a series of per-cycle analyte data sets generated for sequencing cycles of a sequencing run;
processing, through a base caller and from the series of per-cycle analyte data sets, an initial subject window of per-cycle analyte data sets corresponding to an initial subject window of sequencing cycles of the sequencing run;
generating, utilizing the base caller, provisional base call predictions for a set of sequencing cycles in the initial subject window of sequencing cycles in which a target sequencing cycle appears at a target position; and
determining a base call for the target sequencing cycle based on particular provisional base call predictions for the target sequencing cycle from the provisional base call predictions.

18. The computer-implemented method of claim 17, wherein:
accessing the series of per-cycle analyte data sets comprises access the series of per-cycle analyte data sets for one or more image channels at the sequencing cycles of the sequencing run; and
processing the initial subject window of per-cycle analyte data comprises processing, through the base caller, the initial subject window of per-cycle analyte data sets for the one or more image channels.

19. The computer-implemented method of claim 17, wherein the base caller comprises a neural network-based base caller.

20. The computer-implemented method of claim 19, wherein generating the provisional base call predictions for the set of sequencing cycles in the initial subject window of sequencing cycles comprises:
applying spatial convolution layers of the neural network-based base caller to the series of per-cycle analyte data sets to generate a spatially convolved representation of the series of per-cycle analyte data set;
applying temporal convolution layers of the neural network-based base caller to combine the spatially convolved representation of the series of per-cycle analyte data set; and
applying an output layer of the neural network-based base caller to the combined and convolved representation of the series of per-cycle analyte data set to generate, for the target sequencing cycle, probabilities of individual nucleotide bases.

* * * * *